United States Patent
Collin et al.

(10) Patent No.: US 9,771,580 B2
(45) Date of Patent: Sep. 26, 2017

(54) ANTISENSE OLIGONUCLEOTIDES FOR THE TREATMENT OF LEBER CONGENITAL AMAUROSIS

(75) Inventors: Robert Wilhelmus Johanna Collin, Venlo (NL); Franciscus Peter Maria Cremers, Malden (NL); Antonia Ingrid Den Hollander, Groesbeek (NL)

(73) Assignee: Stichting Katholieke Universiteit, Nijmegen (NL)

( * ) Notice: Subject to any disclaimer, the term of this patent is extended or adjusted under 35 U.S.C. 154(b) by 143 days.

(21) Appl. No.: 14/342,776

(22) PCT Filed: Apr. 25, 2012

(86) PCT No.: PCT/NL2012/050275
§ 371 (c)(1),
(2), (4) Date: Jun. 16, 2014

(87) PCT Pub. No.: WO2013/036105
PCT Pub. Date: Mar. 14, 2013

(65) Prior Publication Data
US 2014/0336238 A1 Nov. 13, 2014

Related U.S. Application Data

(60) Provisional application No. 61/531,137, filed on Sep. 6, 2011.

(30) Foreign Application Priority Data

Sep. 5, 2011 (NL) ..................................... 2007351

(51) Int. Cl.
*C12N 15/113* (2010.01)

(52) U.S. Cl.
CPC ........ *C12N 15/113* (2013.01); *C12N 2310/11* (2013.01); *C12N 2310/15* (2013.01); *C12N 2310/321* (2013.01); *C12N 2310/346* (2013.01); *C12N 2320/33* (2013.01); *C12N 2320/34* (2013.01)

(58) Field of Classification Search
None
See application file for complete search history.

(56) References Cited

U.S. PATENT DOCUMENTS

| | | | | |
|---|---|---|---|---|
| 7,517,644 B1 * | 4/2009 | Smith | .................. | C12Q 1/6886 435/375 |
| 9,487,782 B2 * | 11/2016 | Rozet | .................... | C12N 15/113 |
| 2005/0118625 A1 * | 6/2005 | Mounts | ................ | C12Q 1/6837 435/6.14 |
| 2005/0233455 A1 * | 10/2005 | Damha | .................. | C07H 21/02 435/455 |
| 2009/0269755 A1 * | 10/2009 | Aartsma-Rus | ..... | A61K 48/0016 435/6.11 |
| 2012/0108654 A1 * | 5/2012 | Campochiaro | ...... | A61K 38/446 514/44 R |

FOREIGN PATENT DOCUMENTS

| | | |
|---|---|---|
| WO | WO 2009/121536 A1 | 10/2009 |
| WO | WO-2012/168435 A1 | 12/2012 |

OTHER PUBLICATIONS

Lanfranchi, G., et al. "Identification of 4370 expressed sequence tags from a 3'-end-specific cDNA library of human skeletal muscle by DNA sequencing and filter hybridization." Genome Research 6.1 (1996): 35-42.*
Collin, et al. Antisense oligonucleotide (AON)-based therapy for CEP290-associated LCA. Poster presented at: ARVO Annual Meeting; May 3, 2011; Program No. 3324, Poster No. A572.*
Baye, Lisa M., et al., "The N-terminal region of centrosomal protein 290 (CEP290) restores vision in a zebrafish model of human blindess". Human Molecular Genetics, vol. 20, No. 8, Apr. 15, 2011, pp. 1467-1477, XP055009210.
Cideciyan, Artur V., et al., "Centrosomal-Ciliary Gene CEP290/NPHP6 Mutations Result in Blindenss With Unexpected Sparing of Photoreceptors and Visual Brain: Implications for Therapy of Leber Congenital Amaurosis", Human Mutation, vol. 28, No. 11, Nov. 1, 2007, pp. 1074-1083, XP055009211.
Collin, Rob W., "Antisense Oligonucleotide (AON)-based Therapy for Cep290-associated LCA", Association for Research in Vision and Ophthalmology, Inc., May 3, 2011, Retrieved from the Internet: URL:http://www.abstractsonline.com/plan/ViewAbstract. espx?mID=2684&sKey=9456c86d-1d58-492c-ab4f-bc1dfbebebee&cKey=71c3af2d-9c21-4900-9e44-fd5d22b87025 &mKey={6F224A2D-AF6A-4533-8BBB-6A8D7B26EDB3}, XP002672731.
Den Hollander, Anneke I., et al., "Mutations in the CEP290 (NPHP6) Gene are a Frequent Cause of Leber Congenital Amaurosis", The American Journal of Human Genetics, vol. 79, No. 3, Sep. 1, 2006, pp. 556-561, XP002660978.
Gerard, X., et al., "Antisense Oligonucleotide-Mediated Exon Skipping Restores Primary Cilia Assembly in Fibroblasts Harbouring the Common LCA CEP290 c. 2991+1655G>A Mutation", American Society of Human Genetics, 2011, Retrieved from the Internet: URL:http://www.ichg2011.org/cgi-bin/showdetail. pl?absno=10361, XP002672732.
Gerard, Xavier, et al., "AON-mediated Exon Skipping Restores Ciliation in Fibroblasts Harboring the Common Leber Congenital Amaurosis CEP290 Mutation", Molecular Therapy-Nucleic Acids, American Society of Gene & Cell Therapy, vol. 1, Ed. 29, Jun. 26, 2012, pp. 1-9.
International Search Report dated Aug. 28, 2012, in related International Patent Application No. PCT/NL2012/050275.
Baala, et al. "Pleiotropic effects of CEP290 (NPHP6) mutations extend to Meckel syndrome", Am J Hum Genet (2007) vol. 81, 170-179.
Bainbridge, et al. "Effect of gene therapy on visual function in Leber's congenital amaurosis", N Engl J Med (2008) vol. 358, 2231-2239.

(Continued)

*Primary Examiner* — Jennifer Pitrak McDonald
(74) *Attorney, Agent, or Firm* — Gilberto M. Villacorta; Sunit Talapatra; Foley & Lardner LLP

(57) ABSTRACT

The present invention relates to the fields of medicine and immunology. In particular, it relates to novel antisense oligonucleotides that may be used in the treatment, prevention and/or delay of Leber congenital amaurosis.

6 Claims, 5 Drawing Sheets

(56) References Cited

OTHER PUBLICATIONS

Figure 1:
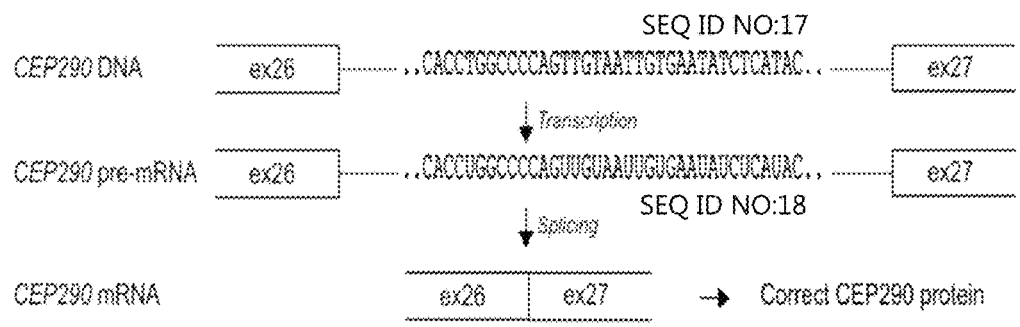
Figure 1:
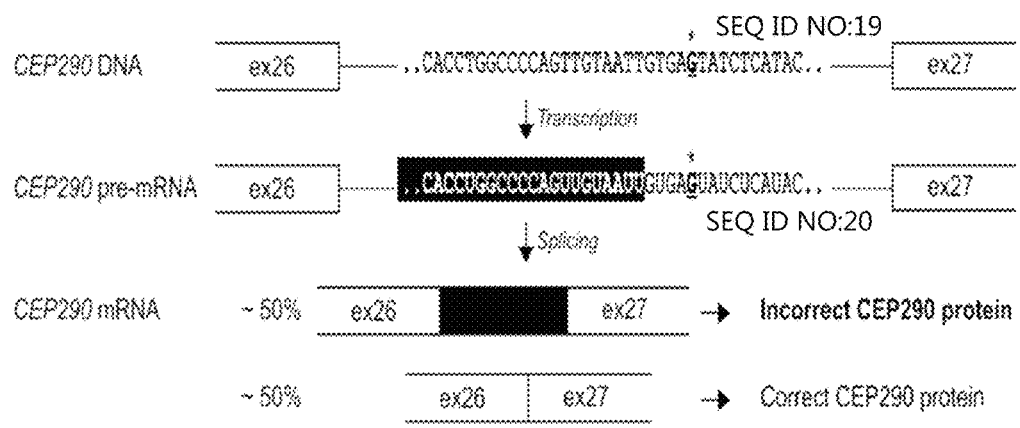
Figure 1:
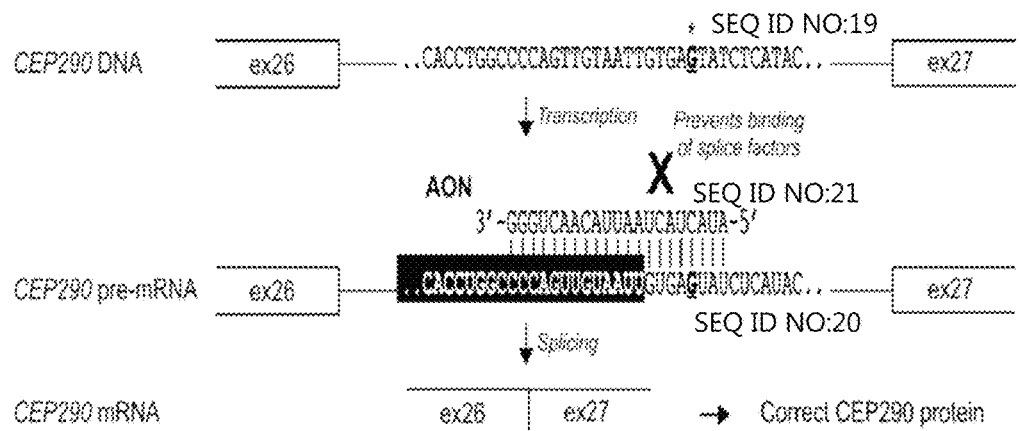

Cideciyan, et al. "Human gene therapy for RPE65 isomerase deficiency activates the retinoid cycle of vision but with slow rod kinetics", Proc Natl Acad Sci (2008) vol. 105, 15112-15117.

Coppieters, et al. "Genetic screening of LCA in Belgium: predominance of CEP290 and identification of potential modifier alleles in AHI1 of CEP290-related phenotypes", Hum Mutat (2010) vol. 31, E1709-E1766.

Den Hollander, et al. "Leber congenital amaurosis: genes, proteins and disease mechanisms", Prog Retin Eye Res (2008) vol. 27, 391-419.

Den Hollander, et al. "Lighting a candle in the dark: advances in genetics and gene therapy of recessive retinal dystrophies", J Clin Invest (2010) vol. 120, 3042-3053.

Estrada-Cuzcano, et al. "IQCB1 mutations in patients with leber congenital amaurosis", Invest Ophthalmol Vis Sci (2011) vol. 52, 834-839.

Helou, et al. "Mutation analysis of NPHP6/CEP290 in patients with Joubert syndrome and Senior-Loken syndrome", J Med Genet (2007) vol. 44, 657-663.

Koenekoop, et al. "Genetic testing for retinal dystrophies and dysfunctions: benefits, dilemmas and solutions", Clin Experiment Ophthalmol (2007) vol. 35, 473-485.

Leber "Uber Retinitis Pigmentosa und angeborene Amaurose", von Graefe's Archives Ophthalmology (1869) vol. 15, pp. 1-25.

Littink, et al. "A novel nonsense mutation in CEP290 induces exon skipping and leads to a relatively mild retinal phenotype", Invest Ophthalmol Vis Sci (2010) Vo. 51, 3646-3652.

Maguire, et al. "Age-dependent effects of RPE65 gene therapy for Leber's congenital amaurosis: a phase 1 dose-escalation trial", Lancet (2009) vol. 374, 1597-1605.

Maguire, et al. "Safety and efficacy of gene transfer for Leber's congenital amaurosis", N Engl J Med (2008) vol. 358, 2240-2248.

Perrault, et al. "Spectrum of NPHP6/CEP290 mutations in Leber congenital amaurosis and delineation of the associated phenotype", Hum Mutat (2007), vol. 28, 416.

Stone "Leber congenital amaurosis—a model for efficient genetic testing of heterogeneous disorders: LXIV Edward Jackson Memorial Lecture", Am J Ophthalmol (2007) vol. 144, 791-811.

Valente, et al. "Mutations in CEP290, which encodes a centrosomal protein, cause pleiotropic forms of Joubert syndrome", Nat Genet (2006) vol. 38, 623-625.

* cited by examiner

A Wild-type *CEP290*

B LCA mutant *CEP290*

C LCA mutant *CEP290* + AON

SEQUENCE LISTING

```
<160> NUMBER OF SEQ ID NOS: 21

<210> SEQ ID NO 1
<211> LENGTH: 93203
<212> TYPE: DNA
<213> ORGANISM: Homo sapiens
<220> FEATURE:
<221> NAME/KEY: 5'UTR
<222> LOCATION: (1)..(909)
<223> OTHER INFORMATION: Intron from 318 to 882
<220> FEATURE:
<221> NAME/KEY: exon
<222> LOCATION: (910)..(1011)
<220> FEATURE:
<221> NAME/KEY: Intron
<222> LOCATION: (1012)..(1183)
<220> FEATURE:
<221> NAME/KEY: exon
<222> LOCATION: (1184)..(1261)
<220> FEATURE:
<221> NAME/KEY: Intron
<222> LOCATION: (1262)..(2652)
<220> FEATURE:
<221> NAME/KEY: exon
<222> LOCATION: (2653)..(2722)
<220> FEATURE:
```

```
<221> NAME/KEY: Intron
<222> LOCATION: (2723)..(3025)
<220> FEATURE:
<221> NAME/KEY: exon
<222> LOCATION: (3026)..(3072)
<220> FEATURE:
<221> NAME/KEY: Intron
<222> LOCATION: (3073)..(5430)
<220> FEATURE:
<221> NAME/KEY: exon
<222> LOCATION: (5431)..(5574)
<220> FEATURE:
<221> NAME/KEY: Intron
<222> LOCATION: (5575)..(10998)
<220> FEATURE:
<221> NAME/KEY: exon
<222> LOCATION: (10999)..(11052)
<220> FEATURE:
<221> NAME/KEY: Intron
<222> LOCATION: (11053)..(11651)
<220> FEATURE:
<221> NAME/KEY: exon
<222> LOCATION: (11652)..(11672)
<220> FEATURE:
<221> NAME/KEY: Intron
<222> LOCATION: (11673)..(11796)
<220> FEATURE:
<221> NAME/KEY: exon
<222> LOCATION: (11797)..(11949)
<220> FEATURE:
<221> NAME/KEY: Intron
<222> LOCATION: (11950)..(12340)
<220> FEATURE:
<221> NAME/KEY: exon
<222> LOCATION: (12341)..(12523)
<220> FEATURE:
<221> NAME/KEY: Intron
<222> LOCATION: (12524)..(13181)
<220> FEATURE:
<221> NAME/KEY: exon
<222> LOCATION: (13182)..(13271)
<220> FEATURE:
<221> NAME/KEY: Intron
<222> LOCATION: (13272)..(15778)
<220> FEATURE:
<221> NAME/KEY: exon
<222> LOCATION: (15779)..(15901)
<220> FEATURE:
<221> NAME/KEY: Intron
<222> LOCATION: (15902)..(16847)
<220> FEATURE:
<221> NAME/KEY: exon
<222> LOCATION: (16848)..(16971)
<220> FEATURE:
<221> NAME/KEY: Intron
<222> LOCATION: (16972)..(21050)
<220> FEATURE:
<221> NAME/KEY: exon
<222> LOCATION: (21051)..(21220)
<220> FEATURE:
<221> NAME/KEY: Intron
<222> LOCATION: (21221)..(21940)
<220> FEATURE:
<221> NAME/KEY: exon
<222> LOCATION: (21941)..(22103)
<220> FEATURE:
<221> NAME/KEY: Intron
<222> LOCATION: (22104)..(23473)
<220> FEATURE:
<221> NAME/KEY: exon
<222> LOCATION: (23474)..(23574)
<220> FEATURE:
<221> NAME/KEY: Intron
<222> LOCATION: (23575)..(23646)
<220> FEATURE:
<221> NAME/KEY: exon
<222> LOCATION: (23647)..(23734)
<220> FEATURE:
<221> NAME/KEY: Intron
```

```
<222> LOCATION: (23735)..(25071)
<220> FEATURE:
<221> NAME/KEY: exon
<222> LOCATION: (25072)..(25184)
<220> FEATURE:
<221> NAME/KEY: Intron
<222> LOCATION: (25185)..(27034)
<220> FEATURE:
<221> NAME/KEY: exon
<222> LOCATION: (27035)..(27119)
<220> FEATURE:
<221> NAME/KEY: Intron
<222> LOCATION: (27120)..(27654)
<220> FEATURE:
<221> NAME/KEY: exon
<222> LOCATION: (27655)..(27797)
<220> FEATURE:
<221> NAME/KEY: Intron
<222> LOCATION: (27798)..(30358)
<220> FEATURE:
<221> NAME/KEY: exon
<222> LOCATION: (30359)..(30523)
<220> FEATURE:
<221> NAME/KEY: Intron
<222> LOCATION: (30524)..(30865)
<220> FEATURE:
<221> NAME/KEY: exon
<222> LOCATION: (30866)..(31015)
<220> FEATURE:
<221> NAME/KEY: Intron
<222> LOCATION: (31016)..(33035)
<220> FEATURE:
<221> NAME/KEY: exon
<222> LOCATION: (33036)..(33151)
<220> FEATURE:
<221> NAME/KEY: Intron
<222> LOCATION: (33152)..(35118)
<220> FEATURE:
<221> NAME/KEY: exon
<222> LOCATION: (35119)..(35221)
<220> FEATURE:
<221> NAME/KEY: Intron
<222> LOCATION: (35222)..(35311)
<220> FEATURE:
<221> NAME/KEY: exon
<222> LOCATION: (35312)..(35542)
<220> FEATURE:
<221> NAME/KEY: Intron
<222> LOCATION: (35543)..(39205)
<220> FEATURE:
<221> NAME/KEY: exon
<222> LOCATION: (39206)..(39379)
<220> FEATURE:
<221> NAME/KEY: Intron
<222> LOCATION: (39380)..(45217)
<223> OTHER INFORMATION: Aberrant exon included in mutant CEP290 mRNA
      position 40902-41209 mutated nucleotide A>G in LCA patients at
      position 41034
<220> FEATURE:
<221> NAME/KEY: exon
<222> LOCATION: (45218)..(45329)
<220> FEATURE:
<221> NAME/KEY: Intron
<222> LOCATION: (45330)..(48241)
<220> FEATURE:
<221> NAME/KEY: exon
<222> LOCATION: (48242)..(48447)
<220> FEATURE:
<221> NAME/KEY: Intron
<222> LOCATION: (48448)..(49384)
<220> FEATURE:
<221> NAME/KEY: exon
<222> LOCATION: (49385)..(49536)
<220> FEATURE:
<221> NAME/KEY: Intron
<222> LOCATION: (49537)..(51377)
<220> FEATURE:
<221> NAME/KEY: exon
<222> LOCATION: (51378)..(51489)
```

```
<220> FEATURE:
<221> NAME/KEY: Intron
<222> LOCATION: (51490)..(52729)
<220> FEATURE:
<221> NAME/KEY: exon
<222> LOCATION: (52730)..(53185)
<220> FEATURE:
<221> NAME/KEY: Intron
<222> LOCATION: (53186)..(54272)
<220> FEATURE:
<221> NAME/KEY: exon
<222> LOCATION: (54273)..(54437)
<220> FEATURE:
<221> NAME/KEY: Intron
<222> LOCATION: (54438)..(55718)
<220> FEATURE:
<221> NAME/KEY: exon
<222> LOCATION: (55719)..(55826)
<220> FEATURE:
<221> NAME/KEY: Intron
<222> LOCATION: (55827)..(56043)
<220> FEATURE:
<221> NAME/KEY: exon
<222> LOCATION: (56044)..(56178)
<220> FEATURE:
<221> NAME/KEY: Intron
<222> LOCATION: (56179)..(57364)
<220> FEATURE:
<221> NAME/KEY: exon
<222> LOCATION: (57365)..(57631)
<220> FEATURE:
<221> NAME/KEY: Intron
<222> LOCATION: (57632)..(58262)
<220> FEATURE:
<221> NAME/KEY: exon
<222> LOCATION: (58263)..(58370)
<220> FEATURE:
<221> NAME/KEY: Intron
<222> LOCATION: (58371)..(58986)
<220> FEATURE:
<221> NAME/KEY: exon
<222> LOCATION: (58987)..(59186)
<220> FEATURE:
<221> NAME/KEY: Intron
<222> LOCATION: (59187)..(61821)
<220> FEATURE:
<221> NAME/KEY: exon
<222> LOCATION: (61822)..(62035)
<220> FEATURE:
<221> NAME/KEY: Intron
<222> LOCATION: (62036)..(62987)
<220> FEATURE:
<221> NAME/KEY: exon
<222> LOCATION: (62988)..(63125)
<220> FEATURE:
<221> NAME/KEY: Intron
<222> LOCATION: (63126)..(64298)
<220> FEATURE:
<221> NAME/KEY: exon
<222> LOCATION: (64299)..(64520)
<220> FEATURE:
<221> NAME/KEY: Intron
<222> LOCATION: (64521)..(64872)
<220> FEATURE:
<221> NAME/KEY: exon
<222> LOCATION: (64873)..(64995)
<220> FEATURE:
<221> NAME/KEY: Intron
<222> LOCATION: (64996)..(70290)
<220> FEATURE:
<221> NAME/KEY: exon
<222> LOCATION: (70291)..(70436)
<220> FEATURE:
<221> NAME/KEY: Intron
<222> LOCATION: (70437)..(70767)
<220> FEATURE:
<221> NAME/KEY: exon
<222> LOCATION: (70768)..(70923)
<220> FEATURE:
```

```
<221> NAME/KEY: Intron
<222> LOCATION: (70924)..(73571)
<220> FEATURE:
<221> NAME/KEY: exon
<222> LOCATION: (73572)..(73695)
<220> FEATURE:
<221> NAME/KEY: Intron
<222> LOCATION: (73696)..(78101)
<220> FEATURE:
<221> NAME/KEY: exon
<222> LOCATION: (78102)..(78236)
<220> FEATURE:
<221> NAME/KEY: Intron
<222> LOCATION: (78237)..(79438)
<220> FEATURE:
<221> NAME/KEY: exon
<222> LOCATION: (79439)..(79525)
<220> FEATURE:
<221> NAME/KEY: Intron
<222> LOCATION: (79526)..(81222)
<220> FEATURE:
<221> NAME/KEY: exon
<222> LOCATION: (81223)..(81387)
<220> FEATURE:
<221> NAME/KEY: Intron
<222> LOCATION: (81388)..(82196)
<220> FEATURE:
<221> NAME/KEY: exon
<222> LOCATION: (82197)..(82319)
<220> FEATURE:
<221> NAME/KEY: Intron
<222> LOCATION: (82320)..(83196)
<220> FEATURE:
<221> NAME/KEY: exon
<222> LOCATION: (83197)..(83369)
<220> FEATURE:
<221> NAME/KEY: Intron
<222> LOCATION: (83370)..(86499)
<220> FEATURE:
<221> NAME/KEY: exon
<222> LOCATION: (86500)..(86641)
<220> FEATURE:
<221> NAME/KEY: Intron
<222> LOCATION: (86642)..(87803)
<220> FEATURE:
<221> NAME/KEY: exon
<222> LOCATION: (87804)..(87877)
<220> FEATURE:
<221> NAME/KEY: Intron
<222> LOCATION: (87878)..(88470)
<220> FEATURE:
<221> NAME/KEY: exon
<222> LOCATION: (88471)..(88565)
<220> FEATURE:
<221> NAME/KEY: Intron
<222> LOCATION: (88566)..(91783)
<220> FEATURE:
<221> NAME/KEY: exon
<222> LOCATION: (91784)..(91863)
<220> FEATURE:
<221> NAME/KEY: Intron
<222> LOCATION: (91864)..(92802)
<220> FEATURE:
<221> NAME/KEY: exon
<222> LOCATION: (92803)..(93033)
<220> FEATURE:
<221> NAME/KEY: 3'UTR
<222> LOCATION: (93034)..(93203)

<400> SEQUENCE: 1
atttgaagtc ctcgttccac gccttctcat catcctgaac accgagctct gggactccgg      60
cggagaatct aaacgtaaag catcacccac ggtcgtgaac tgtaggctct cctggcatcc     120
gggatcttat tctggccttg gcggagttgg ggatggtgtc gcctagcagc cgctgccgct     180
ttggcttgct cgggaccatt tggctggacc cagagtccgc gtggaaccgc gatagggatc     240
```

| | |
|---|---|
| tgtcagggcc cgcggccggg tccagcttgg tggttgcggt agtgagaggc ctccgctggt | 300 |
| tgccaggctt ggtctaggtg ggtggatcct tgtaagcagg attagcgagt cactccacgc | 360 |
| tcaggttctt tagcctgagg gcccgtgtgc cacagcatag ctaccccgcc cttccagcct | 420 |
| cgggtcccta atactgcctt gcttcggttc cagtttccgc cgcacaactt cactcattcc | 480 |
| aaatgttaat ttctgcgttt tttttcagcc ccaattctgt ttctccaaat cagggatgat | 540 |
| tgtcggcctc ccacagaccc tcgcgcttgc caggattagg gtgttcgcgc gcattgtggg | 600 |
| tagggggtgtg gaggaaggga tccagaaatc ttaagtatta acttagatta gtgttagcaa | 660 |
| ggaagccgtc acattttatt tagccgggac actctgacag tttgtgccga ctgctatttt | 720 |
| tgatcaaggc tattttgccc acttgtctat tttgtggccc aattgtctgt tttgctaaca | 780 |
| tcagaaagtt ataatgaaat aatctgcaaa aaatgtaagg tgctagaaaa ccaataatac | 840 |
| tgtgtacctt gaaatgctaa atatacacct gttttgttac agaggtggag cacagtgaaa | 900 |

| | | |
|---|---|---|
| gaattcaag atg cca cct aat ata aac tgg aaa gaa ata atg aaa gtt gac<br>           Met Pro Pro Asn Ile Asn Trp Lys Glu Ile Met Lys Val Asp<br>            1              5                 10 | | 951 |
| cca gat gac ctg ccc cgt caa gaa gaa ctg gca gat aat tta ttg att<br>Pro Asp Asp Leu Pro Arg Gln Glu Glu Leu Ala Asp Asn Leu Leu Ile<br>15              20               25                 30 | | 999 |
| tcc tta tcc aag gtgcttaatt ggtcaataat aatagatata tacattaact<br>Ser Leu Ser Lys | | 1051 |
| tatgattaat ttattaataa aatatgaatt tatttttttc agggacaact ataattgtca | | 1111 |
| caatctggaa gtgttcttat attttgcttg aaggttataa aatataaaac agttgctttt | | 1171 |
| ctgtttactt ag gtg gaa gta aat gag cta aaa agt gaa aag caa gaa aat<br>            Val Glu Val Asn Glu Leu Lys Ser Glu Lys Gln Glu Asn<br>               35               40               45 | | 1222 |
| gtg ata cac ctt ttc aga att act cag tca cta atg aag gtttgtatgt<br>Val Ile His Leu Phe Arg Ile Thr Gln Ser Leu Met Lys<br>       50              55              60 | | 1271 |

| | |
|---|---|
| agtaggtttt aactataggt ttggctatta gtggaactat aaaaatctgt tcttatataa | 1331 |
| ggtaatcttt gtgaaaatac ctggtaatat ctacatcacc actaaaaaat gcaatatatt | 1391 |
| taaatgtgaa ttaagtattt tagtgtataa aacattgcta gtttctactt aaagtttcta | 1451 |
| aaagggtgtg taggggaaat agaatgagta tgttgaaaag taacataagg aaatatatct | 1511 |
| tgaggtccaa atgacaaatg cagacaatga ctgctatagg gatttgttaa gaggggaaat | 1571 |
| gatttaagag atgtcagaag acttcacaaa ggatcaatac tgaggagtag tgttagataa | 1631 |
| gtggaaggca atgcagtggt aagatagtaa gggaattcta gagctgttgg ttaccataaa | 1691 |
| taaatactga gaacaggaaa tatgtttatt ctttatattt gaggaaacaa ggtgcagcaa | 1751 |
| gtttgtagca gactgtagag aaaacaaatc ttgggtaagt actttgagat aggttgttga | 1811 |
| gggccttaaa ggtgtatttt atgctatcag caattgagaa ggcagtaaag gttttcgaaa | 1871 |
| cacaattgat aggtacaaaa atacaccta agaaggcaaa actgagtata ttatgtagga | 1931 |
| caaactgaag gaaattggag ctttgtagac atcacattat agcggagttt aaacctgaaa | 1991 |
| ttatggatta gaataatagc aattggaaca gaaaaaagt agtggaaaga cattacaaag | 2051 |
| ggagatgttg cattactgga tataagactt gaggacttga ggtaaaaagg agaatcaaaa | 2111 |
| atgtttcatg ctattaaaaa tctagaaatt gtagtcttaa gtaagaaaat tgcctggcat | 2171 |
| ggtggctcac gtctgtaatc ccagcacttt ggaggccaa gcaggagga ttgcttgagc | 2231 |
| ctgggagttc aagactagcc tggataatat agtgagtcct tgcctgtacg aaaaaatttg | 2291 |

```
ccgagcatga tggcacacca agcatgatgg cacgccaagc atgatggcat gcacctgtag    2351
tcccagctac tcaggagact gagatgggaa gattgcttga gcccaggagg caggaggttg    2411
cagtgagctg agattgtgcc actgcactcc agcctgggtg acaaagtgag gccctatctc    2471
aaaagcaaaa aaaacaaaaa caaaaaccaa aaactattta ttcagcaaat atttactgaa    2531
cgtctccatg tgccagccat tgctggcact aaggatcata acaaataaaa cagaattttt    2591
attttcagtg cttacattcc agtataaagg catattgaaa taaccttttt ttaatgttta    2651 g atg aaa gct caa gaa gtg gag ctg gct ttg gaa gaa gta gaa aaa gct    2700
  Met Lys Ala Gln Glu Val Glu Leu Ala Leu Glu Glu Val Glu Lys Ala
               65                  70                  75 gga gaa gaa caa gca aaa ttt g gtaagcacct tggaaaaagt ttattatggt        2752
Gly Glu Glu Gln Ala Lys Phe
                80 attaaataat gaattccatt tgttcattaa actgtagaaa attaaattat attctataaa    2812 atatatatat tcagtttatt tttaatatat aacatttaat aataaatatt tctagactcc    2872 tattttatgg atctgccata taatactttt tgttacctta taatcatgat ggactctttt    2932 aaaagaatta attttgttat tgaaattat  ttaaaagttt gttttgtggt aactaatcaa    2992 ttaaaacgtt tttcttttt  tttaaaaaaa tag aa  aat caa tta aaa act aaa    3045
                                        Glu Asn Gln Leu Lys Thr Lys
                                                 85                90 gta atg aaa ctg gaa aat gaa ctg gag gtatgtcttt ttgtattccc             3092
Val Met Lys Leu Glu Asn Glu Leu Glu
                        95 taggatgtaa ttgtcattaa ttttattttg aattgttttc aaattttaaa attattgttg    3152 gctggaaaaa ttataaggat gattgtaatc atggttattt gtttattctg tatatgttct    3212 acatgcctat tatgtgcctt atatagtact aaggactgag catatggttg tgaacaaaat    3272 aagaagttaa ctgctggatg gagcttatag tcttgggaaa tatacagaaa gattactagt    3332 aactgaggtg gagggtgggt ggggatttga ggaatagtga cgaaagggtg ttatagaagt    3392 aattttttgac aaagctgaag gctaaaatat gaatgtattg ttgaagaaca aaatacattg    3452 agattcctga gaaggtagga atgtgataca aatggatcag cctttgaaag gaggaatacc    3512 cttttccttt gtgttaggag aggaggatga gtggatgagc gtgggaagag tggatgtgta    3572 tagaggcttt tatgtttgta ggcataatgc ttggaagttg aggggttggt gatgacatct    3632 tctgttaaaa agagtgggaa atggtgtggt cacatttaa  ggaaattagg taaaatttga    3692 aatatattgg agacaggact ggagagttgg ggatctggag tcagacagat ttgagttcta    3752 gtcctgattc ttctactcgt taactctctg aacttggatg acctattgtt tttgattgta    3812 tatccagctc ctgggaaaat gccaagcact tcaataaaat actaaatgaa ttatggagtt    3872 ggatcagttc tgtgttagtg tttagctagg tagctgctgt agaatagaag ggtagcacag    3932 ttgaagatat tggtaggaaa gtggttgaag tgatgattat gaagtcttaa ctgaatagat    3992 aaaatcaaga ttggggttgg gtgggcagaa gggtagggat atgagggag  aagatgaggg    4052 gttagagtgt cctgtgaggt cgaaggacag gcatagtggg aataattgaa agaatgttct    4112 ggttggacaa ggatctgatg tgggtgtggg agtgagagac tatagtgaat tcaagaaaaa    4172 aatagactag aacaaaagtt atgtggagat tgcttagtgg gcatttgata gacatctgtg    4232 ggccacatgc ttaaattccc agtgcatttt gcggagttac tggaaggttg gtggcttgtt    4292 tctaccatga gtaggtaaag atggagagca ggatattttg tgagaaagca gctgaagttt    4352 ctataggatg atggaggaat gataggaatg atcacctgaa gttgcagggt ggggtaaacc    4412
```

```
tagaagcacc aacaccttct tctgaccctc atgtatttgg aatctgaaag aatgagcacc    4472
ttccaattga aagagttcca agggcattag tatactaaag gatccaaatt gcagctaagc    4532
caaggagatg gaaaggagga ttcagtaaag aatctgagga tgtgaaatat taatttatct    4592
tggaagagaa ttttagagag cacaatggaa tgcttttggg aggagagaaa gagtaagaac    4652
aatttggtta aggtagagga ataacagaac tataaggtga agaaatgaat gtgagacaca    4712
ttagatgacc aaatgatttg atgttcttgg ccatgacctg aattaacaag actgtgaggt    4772
aaaatggatt taatcggcta caaatcttaa gataaccaaa acctgagctg tttaatatgg    4832
tagcactagc actaaccact tgtagctatt tatatttaca ttggttaaaa ttaaaatgaa    4892
aaatttagtt cttcagttgc actagccaca cttcaaatgc ccgaacatag ctacatgtag    4952
cgagtggcta ttgaactgga cagcactgac agcatgtcca ttatgctaga aagtcctatg    5012
ggacagcact ggtctaaaca gtgcatggta tgagagaaag ggcaggttaa ggcactcagc    5072
ttcactgact ggggtggaga ttctgatggt ttgtactcag gttccagatc cctgaggctc    5132
aggaaccttt gcagtttagt ctggttacct gtggcccagt ggttacaaca gaatgattaa    5192
cagtcaattc tttgcatctc tgggtggctc aggaaaaatt taaggagtta ttagctgtga    5252
actaaccta agtaagttaa attaaaaaaa aaaagttct taagctaata tgattttaaa    5312
tatctgcact gaagtataat gcaaatttaa attcagcata attatttgct tgttgttgac    5372
tcatttgaac ctcaaaatat aatgggatta atttatactt tgggtttatt actttaag     5430
atg gct cag cag tct gca ggt gga cga gat act cgg ttt tta cgt aat     5478
Met Ala Gln Gln Ser Ala Gly Gly Arg Asp Thr Arg Phe Leu Arg Asn
100             105                 110                 115
gaa att tgc caa ctt gaa aaa caa tta gaa caa aaa gat aga gaa ttg     5526
Glu Ile Cys Gln Leu Glu Lys Gln Leu Glu Gln Lys Asp Arg Glu Leu
                120                 125                 130
gag gac atg gaa aag gag ttg gag aaa gag aag aaa gtt aat gag caa     5574
Glu Asp Met Glu Lys Glu Leu Glu Lys Glu Lys Lys Val Asn Glu Gln
            135                 140                 145
gtaaagcact ttttttttcc atgaatcttc actgttcaag ttacctggct ttttattatt    5634
attggtaaca atatcaattt ttatattgta tgttatattt gaaaaatgat gtacacttat    5694
ctctaaggtt ttatatcact gttcattttg tcatcaccaa ttttaaaata taatggtact    5754
tctagtgaat atgacttgaa gattaattct ttatatttgg aagtacattt ttctcaggac    5814
atcaaacttg ttacctaaaa ttaatgcttt tgtctggaag attggtatca agtaactaat    5874
agattttcat aaagaagtga tctttctagt gccatagttt attttgggta aaagttatat    5934
ttgttcattt caatgtattt atatgattag tagattcgca aatgaatctt tcgatatatt    5994
caataatggt taattaaata tcttgttttt ggttgtacct tattttatgt gagatatata    6054
tatatatgta tagttttttga aaagttgtgt tcatgtcagc agtttataaa tcacatatt     6114
aaaataacat ttttaatgca tagtttttat tacctcgtta ttccttgtta taaactaata    6174
attcttgcag tgttcacttg aatttagttt taggaaaaaa gttttttgca gatcaacttg    6234
tatttcctgg aagaaaattt cctatttttac ctcagcttcc tatttaatgt attatttatt    6294
tatttactta acatttattt gttttttatt tcacctgaac tgttagtaaa cttagtaaaa    6354
tttggtgcct acatgtggta actgtcctgt cccttatact cagaaacgtt ttccaccttt    6414
gtgtcccttta ggtcattgtt gtgttatatt ccatttattt tattttgtcc attgttctct    6474
cagaaattga gggtcataca ttttaagaaa acaatgatat gctatttaag agaatgtatc    6534
```

```
ataaattgat ttgtaaggaa aagtatcccc attcttcatg tatgtatttt actctaaaat    6594
gttgaagaat catatagaag ttagctatga aaacaatgtg gtagagaaag tatggatcga    6654
tgccacttaa atgttaggaa gaagctctta gagcattatc tgtttagcta actgcaaaac    6714
atagcagaca tgtggatttt ttaatagtca tcaaggatct aacttataat atacactggt    6774
agaattgctt aggggggatgt ctgtggtttt ctggactttt gttcttctat atagacctgt    6834
atcagttgac ttatcattca taccacacac ccttagctaa tcagaactac cttgtccatt    6894
tatatcttag actattgtct ttttttcatag tcacacacag agaaaacttg aatatatggc    6954
ctgtgttcct ttttggctgc tcaattcctt gagatgaaat atgggtatgg gttgctttgg    7014
caattacttc tttgccgtta accagtcatt cagttttatt gagtctttac agcataccag    7074
aggctgctag ttactagtga tatagtgggc aactatgttc tggttctcaa gaatattcat    7134
agtcaataat aagcataaca tagtgataat atgatactta gggagataca taaggtcata    7194
ttctggcata ctctggagag agataccgta atcagccttg aggtgcagga tgtgatctgt    7254
aaactgagac ctgaagtata gttagactgg taagaggaat gaggatatat atggtggtta    7314 ataaagaac  attctgggta gaagatatag catttgctaa gacctagagg taagagatgt    7374
tatggagtat ttaggaaact acagttattc attttgactg aaatataagt gaaaatagct    7434
ttcatagagt ccttactatg tgccaggcac ttcatatgca ttaattcatt attgcttatt    7494
tgatacttgt catatgagat agttgtcatt tctgccatga tacagatgaa gaaatggaga    7554
cacagaaaga gtaattgccc atggttgcac agcttataaa tggtaaaggt aggatttgaa    7614
aacagtctta ctcaagagtc tgtgctatct tgccttccca gttttatttt ttatgatcct    7674
ctggagagat aagcaagggc cagttcctaa tgaatttggt tcttttcctg aaaggagcca    7734
gtgaagagtt tgagcacag  gatatcatga tcagatctat actttaaaag tttactgtac    7794
tttgtagaga gtggattgaa aagggccaag actagtaagg aaacatttgt gttaattcag    7854
ggaagtgcta atgatggcat ttgcctgaga aagacaagtg tgagagaagt agatgtaatt    7914
ggatgtggtg aatgtaattg gttgttggag gagagggagg atggagagtc tgcctaattt    7974
tgtgggttgg gccactaaat aggtagatag tgccattcat taaggaggaa cacaagagga    8034
atttggaaag cttgagatta tttcagttt t gtagatgttg agtttgaggt tcttctgggc    8094
atattcaaaa agggtatctg tggatatgga attcacaaga gaccctgtac agatgatgag    8154
gatttatgaa tcatcaatgt agacattatt gaagccagag aagtgattgt aaggcacgtc    8214
tctgagaaat gtctaataaa gcaatgaaat aggaagagtg cttcaaggaa aagctcaaga    8274
aaggagaaac agagtgtgat gtttgagaag acaagggaaa aaacattaa  tagcattaaa    8334 tgctttagca ttaagttctt ggcttctctt cttgtaaaaa tttcccaatt cagaacacag    8394
tgggattatt aactttcaat tgataataat aatgataggc aaacttctaa aatttgtatt    8454
gtagtttgca ttttattata aacttttctt aaattttta t tttgaaaaat gtcatatctt    8514
cataaagatt gtaagaaaca cactgttggt gttaatgtaa attagttcaa ccattgtggg    8574
agacagtgtg gcaattcctc gaagatctag aagcagaaat accacttgac ccagcaatcc    8634
cattactggg tatatatccca aaagaatata atcattttc  ttataaagat acttgcacac    8694
atatgttcat tgcagcacta ttcacaatag caaagacatg gaatcaaccc aaatgctcat    8754
caatgataga ctggataatg aaaatgtgga acatatacat catagaatac tatgcagcca    8814
tcaaaagaga atgagaggtc aagcgtggtg actcatgcct acagtcccag cactttggga    8874
ggccgaggca ggcagatcac ttgaggtcag gagttcaaga ccagcctggc cagtatggtg    8934
```

```
aaacccatc tctacaaaaa caaaacaaaa caaacaaaaa ttaactggtc atggtactgt    8994
atgcctgcag tcccagctac ttgggaggct gaggcaggag aatgacttga acccagaagg    9054
cagaggttgc agtgagctga gatcgcacca ctggactcta gccttagcaa caaaactaga    9114
gtttgtctca aaaaaaaaaa aaaaaaaaaa ccggaacaag atcatgtcct ttgcagggac    9174
atgggatgga ggtggaagcc attatcctca gcaaactcac acaggaacag aaaaccaaac    9234
actgcatgtt ctcacttata agtgggagct gaacaatgag aacacatgga cacatggtgg    9294
ggaacaacac acactgggac ccgtcaaggg gtcggggtgg gagaacatca ggaagaatag    9354
ctaatggatg ctgggcttaa tatctaggtt atgggttgat ctgtgcagca agccaccatt    9414
gtacacattt acctaagtaa caaacctgca catcttacac atgtacccca gaacttaaaa    9474
gttgatggga aaaagaaaaa caataaccac ccacataccc ttcatataga ttcaccagtt    9534
cttaatgttg tgccaacttt gctttatctt tttgtcagta tttttacaca cacatgtatt    9594
tctctgtctc ttgtttgttc aatcacattt tttgctgagt catttaagag ctaattgcag    9654
atatgatact ttgcacttaa atatttcagc ttgtctgttt gaaaagaaa gatgttctcc     9714
tacaatgaac acaatataat tgtcatgctc aggaattta atattgattc aacaccatta     9774
tctagtccat aatgagattt cttctaatgg cccaataata tccttcagtc tccccacctc    9834
caatatccaa agttctgtca aggatcacat actacatttg gttctttatt atagactttt    9894
taaatatcgt tgtataccat tgtgattcta tcgtctcctt taataaagag gagaaccaga    9954
aaaatgaaag gtcataagag gaatgaggtt tggagaatag gtgaaaaaag gcatcataat    10014
gtttataata atgtttgcct gttcagagaa acaagaatca cagataaagt cacttatatg    10074
tagataagag aatgctgtat tacttttttgc tattctattc actgatcatt tttctaagaa    10134
ctctgtatgc ttcttgttta actcttatgt cagcatgtat gagaaaactg agttaaagag    10194
atgttaagta actcattcat gctttactag aaattggttg atgagggaca taaacctagg    10254
ccggtgtgat tttagattgc ttcttttaac cattgtgttg tattgcctta tatttctaag    10314
taatttatgt tcactgagag caaataatag tctagctatg acttagaaaa gtaaaataaa    10374
gatgttgggc agaaaaccat tttattaggg gttttttttgg aggagcagat taatttgttt    10434
ctgtattctt tggttagttt gtgtgtgtgt tctttttaat tctttaaaat gaaactgttt    10494
aatccttaaa tccttaagtt ttgaaaattt tggcctatta tttatgtgtt aggttgatat    10554
taaatcctta atagctttaa cattttctac tttgttagag aggatttaaa atttaagtag    10614
ataagctgaa tatctggctt tatattaaat tactgctgat ggccaggcac agtggctcat    10674
gtctgaaatc ctagcacttt gggaggttga ggcagatgga tcacttgagg ccaggagttc    10734
aagaccagcc tggctaacac agtgaaaccc cgtctctact aaaaatacaa aaattagcca    10794
gttatggtaa tgcatgccag taattccagc tactcggtag gctgaggtgg gagaattgct    10854
tgaaccggga ggcagaggtt gcagtgagcc gagatcgcac cactgtactc cagcctaggc    10914
gacaaagact ttgtctcaaa aaaaaaaaaa attactgctg aatttttatct tcttcttatt    10974
tatttttttt ttttactatt ttag ttg gct ctt cga aat gag gag gca gaa       11025
                            Leu Ala Leu Arg Asn Glu Glu Ala Glu
                                        150             155
aat gaa aac agc aaa tta aga aga gag gtaaaaaatt ttagtagttg             11072
Asn Glu Asn Ser Lys Leu Arg Arg Glu
        160             165
tggtggttca acaaaggtac ttattaaaat aagtacctaa gtttacataa atttatattt    11132
```

```
taaccaggac tggagtcttc taagtaactg atgttttcag actgatttta tggtatgact    11192
ttgtctcagg gaaatagaaa acaaagcaaa atgtgaggcc attaagtatt acattcatct    11252
caggtctatg cgggtaaatc ttttttgtt gttttataag ccattctttg ctagttttct    11312
aattgaatag atgactggat ttctattctt atttctctta cccagaatcc tttaaaattt    11372
tttgttactt gtggaatctt ataaattctg attatcattt ggttctactg agccaaataa    11432
tgtttgtaca ttgtttattc tgatagaagt tcttaagttt ctaacataat tgaaatatta    11492
tttgttttgg tagataatta gtattctttc tttggttatt caagataata tgcatcattt    11552
tcccaaaatt tttttgtttt ctttagtttc tgattattat ttttaattat gtattacctt    11612
tctcatttct aattaccgtt ttcctgtcct tttctgtag aac aaa cgt cta aag      11666
                                            Asn Lys Arg Leu Lys
                                                            170 aaa aag gtgaggcttt aagtgtggtg aaatcttggg aatttaaaat atgttgtgag       11722
Lys Lys agcactattt agaggatatg attttgttat tctgaatagt tttgtaattg aatgttgtgt    11782
ttggttacct tcag aat gaa caa ctt tgt cag gat att att gac tac cag     11832
              Asn Glu Gln Leu Cys Gln Asp Ile Ile Asp Tyr Gln
                  175                 180 aaa caa ata gat tca cag aaa gaa aca ctt tta tca aga aga ggg gaa    11880
Lys Gln Ile Asp Ser Gln Lys Glu Thr Leu Leu Ser Arg Arg Gly Glu
185             190                 195                 200 gac agt gac tac cga tca cag ttg tct aaa aaa aac tat gag ctt atc    11928
Asp Ser Asp Tyr Arg Ser Gln Leu Ser Lys Lys Asn Tyr Glu Leu Ile
                205                 210                 215 caa tat ctt gat gaa att cag gtaaaatggc tagaagtcaa ttcagagcaa       11979
Gln Tyr Leu Asp Glu Ile Gln
                220 tggttcctaa aaactttaat ttcattacaa tgtaaatata atatttagcc ctacatgtaa   12039 attccctggt ataaatctgt cactatgtac ttgtaaaatg tgaaataaat tacatctttg   12099 aagttgcaac tttttagcca tttttatatt tgcctgtctt ggtcattaag aacaattgag   12159 gtccttatgt actatttct tgattcaatt tgatttaatt ggtcaatgcc aattagtaaa    12219 ggtctataaa gaattctctt ttttttctaga ggacacttat ggctgcgttt aattttaatt  12279 tggtttaaat ttcagttttt ttaaaattac ttttttaatta tagtgtcttt aacttttta   12339 g act tta aca gaa gct aat gag aaa att gaa gtt cag aat caa gaa atg  12388
  Thr Leu Thr Glu Ala Asn Glu Lys Ile Glu Val Gln Asn Gln Glu Met
  225                 230                 235 aga aaa aat tta gaa gag tct gta cag gaa atg gag aag atg act gat    12436
Arg Lys Asn Leu Glu Glu Ser Val Gln Glu Met Glu Lys Met Thr Asp
240                 245                 250                 255 gaa tat aat aga atg aaa gct att gtg cat cag aca gat aat gta ata    12484
Glu Tyr Asn Arg Met Lys Ala Ile Val His Gln Thr Asp Asn Val Ile
                260                 265                 270 gat cag tta aaa aaa gaa aac gat cat tat caa ctt caa gtaagaatta    12533
Asp Gln Leu Lys Lys Glu Asn Asp His Tyr Gln Leu Gln
                275                 280 cttttagaat aacttattta ttcagacttc atattatctc attactattt atttgacact   12593
agaaagtact ttttctagga tgtgaatttt tgtctgtctt tttaatagtg taatatcttg   12653
tcatgttggt atatttgtcc atatgtgttt ctccaatcac ctcacaaaca ctaattttg   12713 caatttagga tatataaatg atacttgaat gaatgtgtag atagcagtca ttatgggtt   12773 ttctataaaa gactactgaa aatcctgtgg atcataacat ttcatttat cttaaaataa   12833
```

-continued

| | |
|---|---|
| atacattata aatgtattag aaaccaatac attgttcagt atttatgtgg attaaatttg | 12893 |
| tttaaaaggt agaataatgt ttaaaaataa aattttctag taatgaaaga taattatgca | 12953 |
| attataagat gcagaaacta ttaaatgtca cctataattc caggatgact tcaatgataa | 13013 |
| atacacatat gtaatgtaat gtatccgtat gtatgtgtat ataagtatga atacgtatgt | 13073 |
| gtgtgtatgt agatatattt atatatataa tgtatatgta aatatgcaca ggtgtaaata | 13133 |
| tatgttacat cagtttgcaa caactcttga aataactttg tcttttag gtg cag gag | 13190 |
|                                                                                                         Val Gln Glu<br>                                                                                                             285 | |
| ctt aca gat ctt ctg aaa tca aaa aat gaa gaa gat gat cca att atg<br>Leu Thr Asp Leu Leu Lys Ser Lys Asn Glu Glu Asp Asp Pro Ile Met<br>     290                       295                           300 | 13238 |
| gta gct gtc aat gca aaa gta gaa gaa tgg aag gtattttttt tcaattgaca<br>Val Ala Val Asn Ala Lys Val Glu Glu Trp Lys<br>   305                       310 | 13291 |
| taataacttt ttcttttgt attttagatt taaattttag tcttatttt ctttaaatgt | 13351 |
| cttatactgg tttataacac gtttattagg gttttttaaac ataagtttat tttatttatt | 13411 |
| ggttagaaaa gctctagaac tgtccttttt gatctctagc taatttgtta ttgaatgacc | 13471 |
| tctttcacat caatgagttt aactttaaac ttttgatag aagtctaact ccaaaatata | 13531 |
| tttggcatct aaaatatata attcgaaata taatttaaat tttttactt aactcatagt | 13591 |
| taccttatat acattagtta aatagttgca ggtttaattt tagttttct aactaaatgt | 13651 |
| caggttcatc agtgggaatg ggaataagca aagggatcag aataacttgg gaagcctttt | 13711 |
| caaaatacac ttttcttcct caccaccact ctccaacctt aaccaaattg tcaggcctta | 13771 |
| ccatattaga agctgggatt atgatggttg tatacttgaa aaacatcaga gattattctg | 13831 |
| aatgaataat tctaattta aaaactatca cttctagagt cattgctttc tagtatggtt | 13891 |
| cacataaatc ttgtgggcag tttggaactg gttagcatct agggagctca gataacctat | 13951 |
| attttaaaca aaagcattag caatggaaat aaggcctata gaatcagtca tgtctccata | 14011 |
| aactttatat aaagggccag acagtgaata ttttagacca cctggtctct gctataacta | 14071 |
| aactctgctt atagcatgaa agcagccatt gacaatacgt aaatgagtga gcaaggtggt | 14131 |
| tttccggtaa aattttattt acaaaagcag atgggaggcc agatttgacc tttgggccat | 14191 |
| agtctaccaa cccctggaaa aaacagttgt ctttaccaga ttgaatgttg gcagggtaaa | 14251 |
| tggtgacatg ttatatgtat tctgtacttt gttttgactt aataccattt cataattatt | 14311 |
| ttatatcagt acgtatagta ttgctgttct tttttaaggc tatgtaattt ttctttttat | 14371 |
| acaggtgtta atttgataat ttgtgaagtt tatgaagttt ccaattttgg ggttgtaaac | 14431 |
| tgttttaatg aatatcctta tatatgttat tttgcaaatg tacaagtata tctgtggaat | 14491 |
| aaattgctgc aagtgttgta attgtcatgt atgttgcaaa tacattctaa cagtttgtca | 14551 |
| cttttttgc tttatggcat ttttttgctgt gaaatatttc tttttatgct tagttaaatt | 14611 |
| tattatttt taatgacttt tgacattgt tataatgaga aaggcttctg agtataaact | 14671 |
| tgttttctca tcttttctcc taatatcttg ttttgttttt gttttgttt tgttttga | 14731 |
| gacagagtct cactcagttg cttaggctgg agtgcaatgg tacaatctca gctcactgca | 14791 |
| aatgccacct cctgggttca ggtggttctt gtgcctcagc ctcctgagta gctgggatta | 14851 |
| caggcatgtg ccgccatgcg cagctaattt ttgtagtttt agtagacatg gggtcacact | 14911 |
| gtgttggcca ggctggtctt gaaccctgg cctcaagtga tcctcctgcc tgggcctccc | 14971 |
| aaagtgctgg aattacaggt gtgactctgc ctggcctttt tttacattta aatcttcgaa | 15031 |

```
acatataatt cattttgatg taaggagtat catgtggatt caacagagct actctgttgt    15091
ccaaacatct tttattgatt atttcatctt ttattgaatt gattgatcta ttttctagca    15151
gtgtatactt gttttaattt gtgtatgttt taatatctaa aaacgttatt attttctgc     15211 ttttagactt ctttatgaat attttaatg tgaattatag aactggcttg tccagttctt    15271
aaaaaatatc ttgtggattt ttattgggta tgtgttaaag ttataaattg ttttatagat    15331
tgatttagga taaaccttt tatgttattt ggtccttcta gctaaagaac aaagatacc      15391 ttttctttca ttcattcaag atattttatg cctcttggtt gcattttaat gcatacttca    15451
taaagatcaa ttgtataaaa cttttcacag ttgtatggaa gtacttcttg tttataaatg    15511
agttttgaaa ggttgaaata ttttaaaga ttgaattata aaaaagaaa attcggtata      15571 tattttaaaa tcattttcta tttgaatttc aggttgtata tacaaaagga acagagatta    15631
tgccagtagt tgctcatact ttctcatttc aaataatttt tattttctgt atcataaatc    15691
tactaacggt gttattatt tatgataatg aagaatgttt tattaacttt ccttttgcat     15751
aacagattct attgtgttta tttctag cta att ttg tct tct aaa gat gat gaa    15805
                              Leu Ile Leu Ser Ser Lys Asp Asp Glu
                                  315             320 att att gag tat cag caa atg tta cat aac cta agg gag aaa ctt aag     15853
Ile Ile Glu Tyr Gln Gln Met Leu His Asn Leu Arg Glu Lys Leu Lys
    325                 330                 335 aat gct cag ctt gat gct gat aaa agt aat gtt atg gct cta cag cag    15901
Asn Ala Gln Leu Asp Ala Asp Lys Ser Asn Val Met Ala Leu Gln Gln
340                 345                 350                 355 gtaaaatctt aacagaattt tgtttatcaa ccagtttat tacagttgga actctgaacg     15961
atgtctttta tttattatat catcagtgcc tagtgtagcg gctggtacta ccaagtgtat    16021
aataatgtct tttgaaattt cttctaccac ctggtcccaa taaaaaatta gaattaagtt    16081
tagatcacgg attagactta gaactagagt tactgtgttt attttctat gtttatgtgg    16141 atagtacaca cattgttttg gttagaaatt atttaacaag aaatgattaa aaactttag    16201 aaatttaaaa taatttata ctctttaag gtttattta ctgtatctta gtcctaacat      16261
accctataca atgtgaaata agctaaaagc atggttataa tttgactgtg ctacctattt    16321 tattttagt gaaataacc caaataaaag gaagtaatac ttttattatt tgtgctgtag     16381
ttatagtcca caagtaagaa gatgatttga aaagtgtatg ctgaataaga acaattacag   16441
gggacaacat tttaataa agtacgaaag ggaaaaagc taagttgaat aaaagagaaa      16501
gcacagagca aaacagaaac atacaaaatg gtaaaaggt ggaattgaat ggaggatgag    16561
gaaagtaaca tataaggaag tatagaagcc ataaacatta gggagttctg gaaatcctat    16621
tttccagagt gttagccatt atatccatct ttcagtattg gagtaacagc agtgtaccta    16681
tcattgtgta ttacagttga agtgtacaaa atggtaaaag gcatacttgt acccacaaga    16741
aaatatgttc tacagtcttg ttgaaaaaaa tcagacgtac ttttttcctt acctttttag    16801
gttaatattc atgaagggat atatattgtt ttaaaatatt ttatag ggt ata cag     16856
                                                  Gly Ile Gln gaa cga gac agt caa att aag atg ctc acc gaa caa gta gaa caa tat    16904
Glu Arg Asp Ser Gln Ile Lys Met Leu Thr Glu Gln Val Glu Gln Tyr
            360                 365                 370 aca aaa gaa atg gaa aag aat act tgt att att gaa gat ttg aaa aat    16952
Thr Lys Glu Met Glu Lys Asn Thr Cys Ile Ile Glu Asp Leu Lys Asn
375                 380                 385                 390 gag ctc caa aga aac aaa g gtattttat aaatatatag ttattttata          17001
Glu Leu Gln Arg Asn Lys
```

```
Glu Leu Gln Arg Asn Lys
            395 tacaattatg tttttaacga ctttattttt attaaaataa aatgtcaagt caatattgag   17061 ttttctccat ttgaatttta tattttcaaa aaattgtaca agatatttat tattatactt   17121 atattactag tgcttacatt tgtaaatgat ggatgcattt tctattattt ttctcctctg   17181 gtgaaaatta cattaacgtt tattaccagg tcactggtat gaaagaaatg aaaaattgtg   17241 atacaattat ttttatttaa cttttttataa ttaacaaaga atggaagata ataaaatttt   17301 gaccagtgta acagcattgc agatagtttt cagaggtaat ttcacattaa tcttacccaa   17361 attaatgttt catcatattc tccttaccct gagccatatt accttttta acacatcaaa   17421 ttctatgaat ataagttctt acaatatctg tgttgttata tttccatagc actacatact   17481 atagttatgc cagggcacac tagtgcgaac tgttcatggg aaattcatgg acatgtttat   17541 tataattggt gactatgtat atatgtatac actacattta tacacacgcg catggaatca   17601 ctatttcttc ttcatgtcat atatatatac atatatacac atatatatac atgtcatatg   17661 tgtgtgtgta tatatatata tttgtatata tgacatgaag aagaaatagt gattccgtgc   17721 acatatgtgt gtgtaagtgt agtgatgtgt ttgcaggtac ggttgtaatt tcaaaaatga   17781 agcaaaagcc ttgctcagga gataattgaa ccaatactta aaggaagtaa aggagtgaaa   17841 catgcagatg gctctaagca gtgggaataa gttcaaaggc agtaaagcag gagtgtacca   17901 atcatgtctg agaacaacaa agaagtcttt ttggctggag tagagtcagc aagtgaggca   17961 gtgataagac cagagaggta aacagaggcc atatcatatg gggcccttata gttcattgtg   18021 cagacttggc ttttaagtga aagggacac cggggaaagt ttctgaagat agaaatgata   18081 taatttgact taggctgtgt ttgcagtaga ctgtaggagt ggtaaataag aatcaggag   18141 acctgttaga agactattgc aataatctgg agaaaagtga tggtggtttg gggcatggtg   18201 gtagcagtgg agttactgga tgcagcagtt ctggatgtat tttgaaagtg ataaaaatgg   18261 aatttgctaa cagatcagat gtaggatgtg agagagagag aactcttggt ctgaaccaaa   18321 agttttggtc atggtggggt tgtgggaaga gcaggttgag agataatcag gtacttaatt   18381 ttagacatgt taggtttgag atgcttatta gacattcaag tgaaggtgtt aagtaggcac   18441 ttgtatataa aagtttaagg tttaggacaa caatctaggc taaagatatg tttggtaact   18501 gtctctgtaa aagtaattga aataatgagg ctggctaaga tcaccaaggg agtaaatgta   18561 ggttaagaag aaaaatctaa agagcttcta ctttagcagc tggggagata aaaaggagct   18621 accaaaggag actgaaaagg aaagcccaga gagctaggag gaaaagcagg agtatggaga   18681 gccctgaaaa ccacatgagg aatgtaacca aggaagaaga aacaactgct ttcagagctg   18741 tgttcattgc tgctgatagg tcaagatgat cactaaaagt tgactattgg acttagcaat   18801 ggtcattttt ggttcaagag aaaatgggta gagaggaaat gtaataaaga aatataggaa   18861 ccctttccca ggactgtttc tataaagaga aggagaaaac aaggtggtag cttgagggga   18921 aagagggatt aagaaaacat ttttctcttt aagatggaag aaataactca tgattttagg   18981 ttaataggag agctccatta aagaagaaac attaatgaat caatgaagtg gagagagaga   19041 acttctggaa caataatatt tttaagaatg caatgggatg ggatcctagt gtgccagtga   19101 agaggttggc cttaactagg aacacagagt tcatccataa ttgtagaaaa gaaggtagag   19161 tgtatagata tcgatgtagg tggcttggta gacatcctgg taatgggaat ttgtggaagt   19221 tctaaactgg ttgctgcttt tttctcagtg aacaagggag caaggttctt agctgaaggt   19281
```

```
gaggatagga gaagatgttt cataagtttg aggagaaaga agagaagtga aagtataaaa   19341
tggtcatctg aaagattgaa gacgtggaga atgtggtatg actgttgagt aacttcaaga   19401
gcccacgata tatatatgta tttctattta tgtgtttatt atatttgtat cagaacactt   19461
tgaaagtagt ttaaactgct ttaaaaggat gactaatagt atggattgtg cgtattctaa   19521
ttactaggag aaaaagtggc aattgatctc tgctgtcaaa taaggaaaag gacttatctg   19581
ataacacttt agtcagtccg tagttatata atccctaaag ctcacagaag gtgtgtgtac   19641
tagactgtac tctacatctt gaacttaact tgtaaaacgt aatggctaat ggtattcttc   19701
cttcataaga ttaggattag gtttagttat caggaacaga gagctgaaga ataatggcaa   19761
aatcaagata gacatttatt tctcatctat gtaatggcct agaattaagc attccagggt   19821
gttgccttca tctgccccat ccaaaatgga tggaatgcag ctttatctca tgtctgtgtc   19881
ccaaacagca agacagagga agaggggcaa gagttaaaag catgtgctga aggataggca   19941
ggtaaatata gtgtttattg tgtagggcca tgtggaagaa tgataggaga atagatatgt   20001
ggatggaagg gagaatagat actggggac  aactcagcct gtgtcatgtt ccacagctta   20061
gatgttagct ccagacagct gtgctcattt cttaaaaact tttgtgatct caaacgtact   20121
agttttatgc ctaagtccaa tattaaatat ataacctata tattagtaaa tgcttataat   20181
gaatgagtgt gagaatgatc tgtcaatcaa ttttggaatg atagcaatat tatgttttgg   20241
tcttttaaca atttagtaag atattacaag taggcattta ggaagttttt agcttagttt   20301
ggattaaatt tagctgcaag tgacagaaaa atcaagcata atacaataat ttaaacaaga   20361
tagaaattta tttctctata atatagacaa agttgaagca actagggcag gatttgtgtg   20421
acagatgctc aaatatcccc tatcaggaac cctgtctctt gttgctgtgc ctatctcaac   20481
atgtggtttc taactcatgt gaagttgcca ccctcatatc catgtggatt tcagctagca   20541
ggaaggagga aagagaagag agattactcc tttattttaa aaacattttt ttttttttt    20601 ttgaaattca catatgaact ttgcgtttat attccattac tgacatgacc acacatagct   20661
gcttgtgtgt aagtggaaat ttagttcttt atttcaaatg gccacgtgtc aagctaaaaa   20721
tccatagttt tagtacagtg gacaaaaggg aggttaaata ttaggaacag ctagcagtct   20781
gtatcacaat gatcattttt tgtaaagcag tatttttgcaa ccttttaaaa tccatacccc   20841
ttcagctaag aaggttttac tgaacttcag tttttttagta aattgtatta gtaaaaccaa   20901
aacaaaactt tcatcttaca aatataaaat gacaacttta aaggattttt ttttaatggc   20961 ataccactt tcttgccacc atgttgggat cactgatttg aaggaataag tagtcaattc    21021
aattcatgat ttttgttttt actctgtag  gt  gct tca acc ctt tct caa cag    21073
                                    Gly Ala Ser Thr Leu Ser Gln Gln
                                                400 act cat atg aaa att cag tca acg tta gac att tta aaa gag aaa act      21121
Thr His Met Lys Ile Gln Ser Thr Leu Asp Ile Leu Lys Glu Lys Thr
405                 410                 415                 420 aaa gag gct gag aga aca gct gaa ctg gct gag gct gat gct agg gaa      21169
Lys Glu Ala Glu Arg Thr Ala Glu Leu Ala Glu Ala Asp Ala Arg Glu
                425                 430                 435 aag gat aaa gaa tta gtt gag gct ctg aag agg tta aaa gat tat gaa      21217
Lys Asp Lys Glu Leu Val Glu Ala Leu Lys Arg Leu Lys Asp Tyr Glu
            440                 445                 450 tcg gtatgtattt ttatcttgtc attcaaggag cttagaatta ttcttgccat           21270
Ser tcacagacta ttctgtgcta tttactgcat accatttaaa aaacattcca taagtatctt   21330
```

```
ttgataaaga ttatcctcat taatttatac taaactattg aaacctttga gcatttactt    21390
tttgccagaa ttgttttcaa acttttgatc acagtgattt gtccaaataa tcagttttgg    21450
tgaagcagca ggattacttt ttttattat ctgtgttcat tgggccacca tgtagatgtg     21510
acaccactgg ccaatttgac agaatttatg acaggaacat actgtgtcaa tacaacctgc    21570
tctccacttt ttatactttt tcattggtta caactaattc aagcaactaa tgacttactt    21630
attctactgg tattgctgat ttgcttttac taattctttt agtattttgg taagtgtttt    21690
ttatatgtaa tgcatattca gagtcacttt gcctttagga tattatactg gaaagttta    21750 actgttgcat attacatcat tattattact ggatttggtt tataaaagca caataaaaaa    21810
ccagtgtaat gatataaatt ataggcatat gtacattttc ctttagactt agtaaaaaaa    21870
aaatcatgaa cttgataaat ttattcaagt aaaccatgtt atattttaaa ttaaattgga    21930
tatttttcag gga gta tat ggt tta gaa gat gct gtc gtt gaa ata aag      21979
        Gly Val Tyr Gly Leu Glu Asp Ala Val Val Glu Ile Lys
            455             460             465 aat tgt aaa aac caa att aaa ata aga gat cga gag att gaa ata tta     22027
Asn Cys Lys Asn Gln Ile Lys Ile Arg Asp Arg Glu Ile Glu Ile Leu
        470             475             480 aca aag gaa atc aat aaa ctt gaa ttg aag atc agt gat ttc ctt gat     22075
Thr Lys Glu Ile Asn Lys Leu Glu Leu Lys Ile Ser Asp Phe Leu Asp
        485             490             495 gaa aat gag gca ctt aga gag cgt gtg g gtaagccatg ttttaagtta          22123
Glu Asn Glu Ala Leu Arg Glu Arg Val
        500             505 catagtttgc gcaacctgat ttacaagtct ttttttttaa tttaaatttt gtttattatt    22183
atttattaag tagtttaatg cttttttcaa atgcttttat aaaacattta atacaaataa    22243
aagtggagct aacctgattg aagtggaatc agatttatg gggttggagt ggtgggtggg     22303
cagggctgga acattgcttt atttggtcta gcatctcctc agtaatagct gcttgtttaa    22363
aaagatgaaa gttattaat accacatatc agagattaac ctttttttt cccaacaaaa      22423 gtagggtctg tattacccat gtttgtttgc aaaatgctct tgtaacagat gagatattta    22483
aacttcttgc tctgtgttgt gattctcctg cctctgcctc ctgagtagct gggattacag    22543
gtgtgcacca ctatgcccgg ctaattttg tattttggt agagatggga tttcaccatg      22603
ttggctaggc tggtctccaa ctcctgacct aagtgatcc acccgccttg gcctcccaaa     22663
gtgctgggat aataggcatg agccaccgcg cctggcctgt aaaatctttt aaagatttt     22723 taagtacttg attttataa tttagactac ttacgtttta ctttgttcga gtattttaag     22783
gagtaattag taatatagct tgagagttta tatttatt ttaataaata gcctattagt      22843
taatattact aatttgagtg ttatgatagt gcagactaag ttgctgcttt aaaatgaaaa    22903
taaatatcta aatatcaatt tcattattgc taaatttcat ttaatgcttt cttagttaaa    22963
aatgatcatt tgtaaaaact attatctaaa gaaaagacaa atagacaaat aagtatttta    23023
tacagatata tatgtgtgaa aagtatctaa cttggatccg tagttgtgct aggaccccaa    23083
attagacttc tgatcaactt ggactatcag atcacagcct tctgatcaac ttggactatc    23143
agatcacagc caagaatctg gaagttccta aagatgactt ctggcccgtc taggtagctg    23203
tcatagacat catatttct gtgcttaaaa agctccaaat cttggtttat aatttcattt     23263 aggttttgt taggatttcc attaataatt gtgataaaat tttaacttgg gttacagttt     23323
aaatatctgg aaaattcttt cacagaaagt tacctcattc ttcagtgata ctggctaagt    23383
gaattataac cagttgcttg atggtatatg acattttgc agcttatttg aatgttttta     23443
```

```
                                                              -continued agtttttaat tatattgctt tctattgtag gc  ctt gaa cca aag aca atg att    23496
                                    Gly Leu Glu Pro Lys Thr Met Ile
                                        510                 515 gat tta act gaa ttt aga aat agc aaa cac tta aaa cag cag cag tac    23544
Asp Leu Thr Glu Phe Arg Asn Ser Lys His Leu Lys Gln Gln Gln Tyr
            520                 525                 530 aga gct gaa aac cag att ctt ttg aaa gag gcaagtgtgg tagtcagttg      23594
Arg Ala Glu Asn Gln Ile Leu Leu Lys Glu
            535                 540 attattttct tggctgaact atagagaaat actaataatt tatactttgc ag att gaa  23652
                                                         Ile Glu agt cta gag gaa gaa cga ctt gat ctg aaa aaa aaa att cgt caa atg    23700
Ser Leu Glu Glu Glu Arg Leu Asp Leu Lys Lys Lys Ile Arg Gln Met
        545                 550                 555 gct caa gaa aga gga aaa aga agt gca act tca g gtatactcag            23744
Ala Gln Glu Arg Gly Lys Arg Ser Ala Thr Ser
560                 565                 570 ttattctaaa cctttaaaaa gaattattga taagtgagtt gtctggatat gaaattattt  23804
gtgtcttagc tgttttttgct gttctattgt ggatctgcta caaatttaat aaatgacaat 23864 aataacctga aggagataag tgagtgtcag tgggttcagt cctgaatctg aaatagacaa  23924
aaacaaaaca aaacaaaata acaaaaacca agcaaacaaa aagaaaaaa accttagaat   23984 tatggaattt ttgaaaagtt ttatagtata gtattttaat ttctagacag caccaatatg  24044
ttgttattaa taataataaa acttagtagt ttttatgtta atatatgtta ctcaacattt  24104
tccctttcct taaggactat gcattgaaaa gcttttcttg taagttatta ttattattat  24164
tattattaat atttgagatg gagtctgtct tgttctattg cccaggctgg agtgcactgg  24224
tgcgatcttg ctcattgcaa cctccgcctc ccgggttcta gtgattcttg tcttcagcc   24284 tcctgagtag ttgagactac aggcgtgagc caccacgcct gacttatttt tgtatttta   24344 gtagaaacag gtttcacca tgttggccca ggctggtctt gaactcctga cctcaagtga  24404
tccatccact ttggctcccc aaagtgctgg aattataggc gtgagccacc atgcctggcc  24464
ttaaattatt ctttttctaag tgaaagtaat gttttattga atataaatta acatcttttct 24524 tgggtttatt ttacttgagc taaagagaac agttggttaa gtttataat agccattgca  24584 gtgcttttt gtaagaagac cacacagaag gactgtcttt ttcacttgcc ccaaatcccc  24644
aagcacgtat atgagtaata gcagagtggt tctttttagc attatgattt ctataataca  24704
tccaaaactt tctcaagaaa aaacttcatg atttattagt acaataatca gtttactcat  24764
tactcatcat ttatatttac tttatatgtc ttttaactgg tgcttattaa gtagcacttt  24824
aatatagaat aggcaaagaa tggtagagaa gatgaaattc aaaaattagg ttctcacatt  24884
attaatagtt cattaaaagt gagctaaatg agaagcttgt attggctatg tagaattttg  24944
gagggatttt ggaaacaatt attctacctt tgcattaaaa cttgattgta ggttttaaga  25004
attaaagtgt tggaatagta ggagggttat tttaatgttt ttagtttgtt aattctctta  25064 tatatag ga  tta acc act gag gac ctg aac cta act gaa aac att tct    25112
            Gly Leu Thr Thr Glu Asp Leu Asn Leu Thr Glu Asn Ile Ser
                    575                 580 caa gga gat aga ata agt gaa aga aaa ttg gat tta ttg agc ctc aaa    25160
Gln Gly Asp Arg Ile Ser Glu Arg Lys Leu Asp Leu Leu Ser Leu Lys
585                 590                 595                 600 aat atg agt gaa gca caa tca aag gtaatagtaa agtattgcaa agagagtaaa   25214
Asn Met Ser Glu Ala Gln Ser Lys
            605
```

```
ggaaaatatt ttttttttt ttttttttg agacggagtc tcgctctgtc tcccaggctg   25274
gagtgcagtg gcgcgatctc ggctcactgc aagctccgcc tcccgggttc atgccattct   25334
cctgcctcag cctcccaagt agctgggact acaggcgccc gccaccacgc ccggctaatt   25394
ttttgtattt ttagtagaga cggggtttca ccgttttagc cgggatggtc tcgatcttct   25454
gacctcgtga tccgcccgcc tcggcctccc aaagtgctgg gattacaggc gtgagccacc   25514
gcgcccggcc aggaaaatat ttttattgtg ttttcatttc ttcccccttt atctcattct   25574
tgaacatcta atcttattat tgttgttaaa aagtagagg gaaatatttg cttatttaac   25634
ctgttgattc aaagattgat taatgagaca ttatttactc tgaatacaga ttaggagttc   25694
agataaagca gagctgctgc ataggagatc atcattcaat accccacagt cagatcagaa   25754
tgagacagaa gagaatatga ccataggatc attatcaaga atgttatctg aaattcacca   25814
tagtgtagaa agtggaatgc atccttttgt ccctttaact agactttctt catccatgca   25874
agttaaagag aattcaactc cagaaactat tacaataaga gagattttta aagcaccatg   25934
tctgcagtct tcaagaaatc tagaatcgtt agtcagcacc tttagtaggg aaagccatga   25994
agaaataaat gacatatgcc ttttttctga tgactgtatg aagaaggtgt caagaagcca   26054
tcaagcacta gagaagacta gttttgtaca aaaaagcaat tcatcttttc atggcttatc   26114
aacagcttca gacataatgc agaagttatc acttaggcaa aaatctgcaa tattttgtca   26174
acaaattcat gaaaatagag ctgacatgga taaatcacaa gtagcaacat tagaagaaga   26234
acaggttcat tcccaagtaa agtatgctga tatcaatttg aaagaagata taataaaaag   26294
tgaagtaccc ttacagacag agatattgaa aaataagctt aaggttaatc ttccagaccc   26354
tgtgtctatt actgcacaat caaaattatc tcagataaat tctcttgaaa atcttataga   26414
acagttacgg agagagctag tatttcttag atctcaggtg agttttttctc caaattatat   26474
ttctgtggtt gttcttttat gacgtctcta acaaagttct gtaacaatta tagttagaat   26534
atttttgttt gcactttaac atcagttata cacattgtac ttttttaaaat ctaaaatgca   26594
gtacattgat atgaactcat tgacttgtct aatttattaa attttttcttt agaatgaaat   26654
catagcacag gaattcttga tcaaagaagc agagtgtaga aatgcagata tagagcttga   26714
acatcacaga agccaggcag aacaggtagt gtaaaggcag aacattaaaa gagatgattg   26774
tggtactaaa gacaaaaacc gttatatctt tttgcctctt accatggatg ttgggagagg   26834
gagaaagtgg gattaagatc accatctgct ttactgttta gattttagtt tattttatg   26894
attgctgcta tgtcttcata gctcgttttt tttgttttgt tttgttatac ttaattgatc   26954
aaacttttct taacttgaaa attatagact tgtgatattt tgttgaaaaa aatcaatttt   27014
attctctctg ctttttcag aat gaa ttt ctt tca aga gaa cta att gaa aaa   27067
                       Asn Glu Phe Leu Ser Arg Glu Leu Ile Glu Lys
                                   610                 615
gaa aga gat tta gaa agg agt agg aca gtg ata gcc aaa ttt cag aat   27115
Glu Arg Asp Leu Glu Arg Ser Arg Thr Val Ile Ala Lys Phe Gln Asn
620             625                 630                 635
aaa t gtaagttaca attatctttt acttttctgt tcttattttt cctatactta   27169
Lys
aaatcatggg cctaaaaggg cgttaacaca ttctctgttt tctaatctgc tttactccta   27229
attacctctg tactgtatat acttcagtct gtcactatcc agttgatttg ccttgctgtt   27289
ttcattgtga gagaatgtta ctaatatgaa ttttttgtga aatatataa ctccttttc   27349
ttgtgtgttc ttcaatcaaa atgaagttag aacaccaaat ttaaaatact taatataaa   27409
```

```
gcatagttta agttaaggca gaagtatgcc ttatatacgt gtgtatatgc acgtgatata    27469
aataggtctg tcatttaact caactattca cgttggattt atagttgaat tttttttgtat   27529 gtttatttac atttggattt ttccaatgat gtctttggta tatgtgaaat atttgtcatc    27589
tgtatagcat agtgtaaatt gtgaaaaaga tctgatcatc aatgagaaa actgtgtaat     27649 tacag ta  aaa gaa tta gtt gaa gaa aat aag caa ctt gaa gaa ggt atg    27698
          Leu Lys Glu Leu Val Glu Glu Asn Lys Gln Leu Glu Glu Gly Met
                640                 645                 650 aaa gaa ata ttg caa gca att aag gaa atg cag aaa gat cct gat gtt      27746
Lys Glu Ile Leu Gln Ala Ile Lys Glu Met Gln Lys Asp Pro Asp Val
            655                 660                 665 aaa gga gga gaa aca tct cta att atc cct agc ctt gaa aga cta gtt      27794
Lys Gly Gly Glu Thr Ser Leu Ile Ile Pro Ser Leu Glu Arg Leu Val
    670                 675                 680 aat gtaagttatt tttttcatgt taatgttttt cccctatcac tttagagaga           27847
Asn ttttctgctg tgtacagatc tccatagttt ctgatgagat attttttagtc atttgaatca   27907 ttgtttccct gtatgtaaag tgtagttttt cttgagctgc tttcaatact tttcttctac    27967
caattggata attgttatta atctgtcttc aagttcactg acattttcct ctttatctgt    28027
gttcttttgg ttcaagggtc agcttgagac cttgaggagt ttttacacc gactttggag     28087 ctcgttttg ctgactcttt tcttattggg attttccttt cacttatccc atggctttgg     28147
gctgtatcct gtggttttct agatgagaaa gatgatagat ctctgcaatt gcaccctgcc    28207
ctatgactaa atctttaaaa atggcaaagt caatctttgc tggtcctgtc ttccgtattt    28267
gaggggtttt ttcccaaaat ctgcttgctt ttgttcattt tctagaacat ctaggtagtt    28327 tttttttcatt catttttttat ttatgggagt gtagatctct taggaactta tgccatcaga   28387
agtattatga aatggcttta ttctaaatgt ttaaagattt actcattgct acaagaaaga    28447
tttagccatc actaatattc tatatatatt taccatatag ggacttgaga atttcacagg    28507
attcagtatc tgtatataaa cttgaataat atacacattt tagattgtta atatttaagt    28567
atatgtcatt tatgttatct gaacatattt agcgtacatt gtcatattat ttcccaaatt    28627
tgtgcttgat ttcaaatggg aaaaaaattc ttattattta ttgaattgtt tttttaaaaa    28687
aatcatgatt aatcagtaat tggatacttt ttaaaataac actataattg ttaacagaga    28747
atgagagtga tactggtatg ttaaaaactt cctgaggcaa gaaaataatt tgattcccat    28807
tatatctttc tcatactgac tttccttctc tgattggtga ttttgttttg cctctgccac    28867
tttgaatgtc taaaatgatt ctttatgctt ttttttatgtg aacatctttt gtccgtgatg   28927
atgcccacta ctgatactgt gtcccagatc aaacttaatt ttccaagggc agctctactt    28987
agtgaccaaa tgaaaacaca gtgaatagcc caagaaatcc taacttctat ttatgttgac    29047
aatctctgga ccttcctgaa gccactgttt gcatagactt catttacttt tatccgggat    29107
tgtcattgtt ttttcagatt cataggccct atctgaaatt cacaaatcac ctagcaatac    29167
ttctctaaga aatcttcaga atccatgaca atttagacca gacaatgctg gattatgcac    29227
ttcagttcac ttttttgttac tacaaggtat ttttcagtgc ccccaacagc tatcttaact    29287
cattctcatt ttaccaaagt ccatgtagac acggcactat tcctcaatga gacaactaac    29347
tagaccacct tgttgtcagt cagagtacct tcctctacct actttatct tccttatatc     29407 ctctttgagt tagtataagt tattactctg catgacctgc tctaatctcc ttcagggaa     29467 ggcttttaca aatctactac ctagagttaa accccagatc accttcctga gtaggagatt    29527
```

```
gcatttggtt ctattcattt taccttattt ggcttctacc ttcacttttt aagacttact   29587
ttgcctttaa cagttttttc catacagttc atctaaagtc caaatatatt tattagatgt   29647
gtgcattgtg tgtatatact tagatatgcc actgttggag atttcgggcc agtgatgcca   29707
ctctgataat attttaatat ttgacatatt attttttgctt actcattatt cttagataat   29767
atcatgttat gataccttgc ctttattttt atttatgctt caactatgtg gagaggaagc   29827
actgaaaaat tcacttaatt gaatgttgta ttgatcaatt gttcaatatt gtattccatt   29887
cctttgcgca tgctttgaat gcaggtgcta taatttca gagaaaaata cctcattttg   29947
actgtacaaa aacccatgt agggagcaga gctcacattg ttttcccctt ttagagacaa   30007
gaaaactaag atacagagaa tttaagtcac ttgcccagct gttaagtgac tgattaaaat   30067
ttgaaccctg gtcatcttat tcccgtctgg ttgttttttct agtctaccag tctattaaga   30127
ttagctaggt gttttttaat tgttttaatg aagtaattac tatgcttggt aatgtaaatg   30187
aaagttttat agattcataa ataagaattt gaattggcat actttattat catgcttggc   30247
aatgaaaata ggaaaatgct taaatgtcca ttttatttaa agacagactg ttttttacta   30307 tgatttact gttttttctcc acatttctaa tatataatat aaatttgcta g gct ata     30364
                                                          Ala Ile
                                                              685 gaa tca aag aat gca gaa gga atc ttt gat gcg agt ctg cat ttg aaa       30412
Glu Ser Lys Asn Ala Glu Gly Ile Phe Asp Ala Ser Leu His Leu Lys
        690                 695                 700 gcc caa gtt gat cag ctt acc gga aga aat gaa gaa tta aga cag gag       30460
Ala Gln Val Asp Gln Leu Thr Gly Arg Asn Glu Glu Leu Arg Gln Glu
    705                 710                 715 ctc agg gaa tct cgg aaa gag gct ata aat tat tca cag cag ttg gca       30508
Leu Arg Glu Ser Arg Lys Glu Ala Ile Asn Tyr Ser Gln Gln Leu Ala
720                 725                 730 aaa gct aat tta aag gtgagaattt tattaaataa agaaaatgc taaacataag        30563
Lys Ala Asn Leu Lys
735 aatgtagatt taataggaaa ttttaatt ttttaaaaga atgctttatg agaaaatgcc       30623 ccttgaatta attctttcaa tattaagaaa ctggatttct cttataaaat tataagtgga     30683 aaataagtgc cttataagat tgaaaagaat acaaaaattc taaatctcat acctaggcat    30743 ttctaagcag aaactgaagt atggttgagg taaaattcct ggcagggcat tcacatatct    30803 gtcaatttgt ctttctttgg gtgtaagagt tgtgattctc attgctggat ttttttttcc    30863 ag ata gac cat ctt gaa aaa gaa act agt ctt tta cga caa tca gaa        30910
   Ile Asp His Leu Glu Lys Glu Thr Ser Leu Leu Arg Gln Ser Glu
       740                 745                 750 gga tca aat gtt gtt ttt aaa gga att gac tta cct gat ggg ata gca      30958
Gly Ser Asn Val Val Phe Lys Gly Ile Asp Leu Pro Asp Gly Ile Ala
755                 760                 765                 770 cca tct agt gcc agt atc att aat tct cag aat gaa tat tta ata cat      31006
Pro Ser Ser Ala Ser Ile Ile Asn Ser Gln Asn Glu Tyr Leu Ile His
            775                 780                 785 ttg tta cag gtattgaaaa ttttgttaca ggtattgaaa attttacatg              31055
Leu Leu Gln tgaataacaa aaatcattgg tagtatgttt ctttatgttt ttatttttat tttactttat     31115
tttaattttt ccatcaccaa agcatgcaga tagtactttt ctcaatattt agtcttcatg    31175
tattcctgag ttctcaaaat agtaacagtg aaatatattt tttatggatt ttgatgttag    31235
atggattata aataaaagca atttatacca ttcattccat tcatctgcat gagcagcatg    31295
```

```
ttcatacatc ttgttcgcac acctgtcatt catgtgaaat atatggttca caagcagaac    31355
aacaagcagc tattataaag cagtgttaag taaatgagca cttttatttc ttgctgggtg    31415
gaaaacaaaa gaataaagtc tgtcaaggct ttttagtgtc atgatagaat tgttcccctt    31475
tttgcattca caagtaaaaa ctactttttt tttgagacag agcctcactc tgtcactcag    31535
gctggagtgc agttgcgcta tcttggctca ctgcaacttc cacctcctga gtttaagtga    31595
ttctcatgcc tcagcctcct gagtagctgg gactacaggc atgcatccct ggctaatttt    31655
tgtatttttt tttagtagag atggtgtgtc gtcatattgg ccaggctggt ctcaaactcc    31715
tggtctcaag tgattcgcct gccttggcct cccaaggtgc tagggttaca gacgtgagcc    31775
actgcacaca gccataagca aaaacttcta aaccaaatta ttcttcatct ttgtcttccc    31835
tttacgcaat aaaatgttaa tctaccacca aagaggaaag ggtactctac tatactacct    31895
gccctgggtt tctcagtttt gctgtctata taatggtcgt tatgaatgtc ctaatgacag    31955
atccttttca ttattttatt tgaaatttga ctatctataa catcacatac attataaata    32015
taattacaaa tatatgttca gaatcaatga aaatatattt ttgattatat gggccactat    32075
ttctctctgc taggtgatcc atttgtgagt atacttgagt tataattatt aagtactcat    32135
ttttattttg gaaattacag taattcatct ttttctcaat attgggattt ttattattat    32195
tttatgttgt ctaaggacag ccttaactac ttattagaat attgctttgt atgtgatatt    32255 attatttta aatgtataat tttaacatta ttatttctct tatttacctg aggtatagga    32315
acactatcag caaatattgg tagtatggca ttgtcgtatt ttttgagata aaattcatga    32375
tttttaatct ttgtataaga aatatatcag aagtttgtag tagattagag agtaccaact    32435
gggagtctga aaagctgtcc aaagtggcaa acaggtact tagactctca atcctaaggc     32495
tgtatagagc tataaacgtg gcaagacctt tggagtcaga cagacccaaa ctcaaatgtt    32555
ggatccatgt atatggaaag cacctgacaa caagcctagc atatgtactt ggtaaaaatg    32615
attgccaagt gtagtgttaa tgagtttttg gatattgagt aagttattta aatttcaatt    32675 tcatcttta aatgaaataa ttggaaagga taatttgagt gagggtatga aattatgtgt     32735
tcataagaga gggtatgtgg ccgagtgact agaggcgagt ttataactat tctatctaat    32795
aaaactttgt aatctggtaa tttgtgtgct aaaaataact ttacctgttg tatagtactc    32855 ttttttatg ccttaaacta aagtgttcaa atatcatgg aaaaatgatc tgtgttgctt      32915
acagatttgg tgactttaa ctttcctata atgttgtcag aatatgaatt tatactttca     32975
aattcagcat ttattctatt gtgttttttt ttgcattctt atttctaaac cacttttcag    33035 gaa cta gaa aat aaa gaa aaa aag tta aag aat tta gaa gat tct ctt     33083
Glu Leu Glu Asn Lys Glu Lys Lys Leu Lys Asn Leu Glu Asp Ser Leu
790             795             800             805 gaa gat tac aac aga aaa ttt gct gta att cgt cat caa caa agt ttg     33131
Glu Asp Tyr Asn Arg Lys Phe Ala Val Ile Arg His Gln Gln Ser Leu
        810             815             820 ttg tat aaa gaa tac cta ag  gtataggtat tagcaaaact ataaatataa         33181
Leu Tyr Lys Glu Tyr Leu Ser
            825 ttgcagtata ttcttgttaa ttgtgaaagt aacgtaagaa taatttatgt tttgttcttc    33241 ccttcttctt cttcctttgc aattgtattt ttttttactc tggtaactac tgttaggaac   33301 ttatttatgg agacagtgta gcttaatgat tacattaagc ctgggattat cctgcctggg    33361 tttgagtcat ttaacgtttg cttttttgtaa gagcttgagc aagtcatctt acctatctgt   33421
```

```
gtctcagttt ccttatctgt aagttacttt gtaagtaata ccctttttcat aggattattg    33481 taaaacgtaa atgaattatt agatgaaaat gctcggacta gtgtgtggca catatgaaca    33541
gtttgtaaat gttagctgtt gttagcatca ttcatcatca tcacaatcat cattgttcat    33601
atatgtttat agggaactaa catatttctc cttatttctg tcatctcatc taaatcaata    33661
gaatgatttc cttaatagga attagaatac ctaatcaaag gtgatttaaa cactaagaat    33721
aattattatc tgacctaacc agaaccacaa agctagttgt agggcaggtc atatttgaag    33781
gttgttgtta tcgcctatga tggttgtaaa atagctgcat gaattcaaga aagatgatgt    33841
gcccattgaa gaagaggagc attttttctc acatagcttt tattttaaaa taaacatttt    33901
tttctggtga tacctggcag acattgactc cgatctcatt tgctagaatt ggatcacatg    33961
tccaagtctg aaccattcag ttgcaaagag aatgataccg ctatactggg tttatgccaa    34021
gaacattaca catgtttgtg gaatgctcat gtgtagacaa cagtgtctta cacaacttca    34081
aaaaaataat ttatatataa atatgtttta aattacttt taaattcaca gaatttatg    34141 gtatacaaca tggtgttcta tatatgtata tactatgcta tacaacatgg tgttctatat    34201
atgtatatac tatgctatac aacatggtgt tctatatatg tatatactgt ggaatggcta    34261
aatcaagcta cttaacatat gtattacctc gcatactttt ttttttttt ccttgagaca    34321 gagtcttgct ctgtcaccca ggctggagtg cagtggcgct atcttggctc actgcaacct    34381
ctgcctcctg ggtccaagtt attttcttgc ctcagcctcc caagtagctg agattacagg    34441
catgtgccac cacgcctggc taattttgt attttggta aagacggagt tttgccatat    34501
tgtccacgct agtctcaaaa ttcctagcct caagcaatct gcccaccttg gcctcccaaa    34561
gtgctgggat tacagcatac ttcttcttat tttttttttt ttttgcacta agaacactta    34621
aaatttactc tcttagcaat tttaaagtat ataatatact gttattaact ttggtcacta    34681
ttttaattag acttaagatg tgtttgtatt caaattattt tgtaagcatt taacacccaa    34741
atttgagagt ggggtcagaa tgttggaatt tgatttctag aattagtata gggtattatt    34801
ttcctacttt ttttctgtgt tcaataaaat gtttataaga ttcagcttca attatattat    34861
aacccattta gtggtgaatc agggaagaat gaaataatt tgataacttt gttgccttgc    34921
atttatttaa aaaattttta attctaggct aaacccttt taaatgaaag tttaacttct    34981
tgtgttttca gatactgaat agctatgata cctcttgtgt tgagaaaact ttaaatttgc    35041
ataatctgaa gttatctttt cttataaaca ttttattagg tttacagtat tgtcttttg    35101 ttttgttttg ttttttag t gaa aag gag acc tgg aaa aca gaa tct aaa aca    35152
              Glu Lys Glu Thr Trp Lys Thr Glu Ser Lys Thr
                   830              835 ata aaa gag gaa aag aga aaa ctt gag gat caa gtc caa caa gat gct    35200
Ile Lys Glu Glu Lys Arg Lys Leu Glu Asp Gln Val Gln Gln Asp Ala
840              845              850              855 ata aaa gta aaa gaa tat aat gtaagtaaaa cattttaac attagtatgc          35251
Ile Lys Val Lys Glu Tyr Asn
            860 aatattgtac aaagtaggat agctagattc aacaagtaat atggatgtgt ctttgtgcag    35311 aat ttg ctc aat gct ctt cag atg gat tcg gat gaa atg aaa aaa ata    35359
Asn Leu Leu Asn Ala Leu Gln Met Asp Ser Asp Glu Met Lys Lys Ile
        865              870              875 ctt gca gaa aat agt agg aaa att act gtt ttg caa gtg aat gaa aaa    35407
Leu Ala Glu Asn Ser Arg Lys Ile Thr Val Leu Gln Val Asn Glu Lys
880              885              890 tca ctt ata agg caa tat aca acc tta gta gaa ttg gag cga caa ctt    35455
```

```
Ser Leu Ile Arg Gln Tyr Thr Thr Leu Val Glu Leu Glu Arg Gln Leu
895                 900                 905                 910 aga aaa gaa aat gag aag caa aag aat gaa ttg ttg tca atg gag gct    35503
Arg Lys Glu Asn Glu Lys Gln Lys Asn Glu Leu Leu Ser Met Glu Ala
                    915                 920                 925 gaa gtt tgt gaa aaa att ggg tgt ttg caa aga ttt aag gtacatctga     35552
Glu Val Cys Glu Lys Ile Gly Cys Leu Gln Arg Phe Lys
                930                 935 ttcttatttt gcttttctg  actatgaaaa atttcaaata tgcagaagat aggatggtat   35612
caataatgct catcacctga attaatagtt aacatttatt aacattttgt cataattgct   35672
tcttctgatt tttgtgggat gtttgaattg cagacattcc tcccctaaat atttaatgta   35732
cccttttgaa aaaggctttt ttctttaact aaccatagta actttattat acctaacaaa   35792
atgacagtaa ttttctaata tcgcctaata ccctgattat agtcacattt tttacatttt   35852
ttgatcaaag aataagcatt tggatgttac atctcataaa tcttttttaat atagaatccc  35912 cttggttttc tttttctcca aaaaatgttt gaagatgtat ctaactttg tgtgtgtgtc    35972 attttacttg ttcctgtgtc ccttgtatta ctaaaagtta ggtcagaacc ctaagttaca   36032
ttcaggttta aacattttg  gcaagaatac ttcataagta gtgttctata ctttatattg   36092
catcacttca agagtatctg gttgttccat gttttgtaat tgattactct gttaaggaaa   36152
agacaagcag accaagtatg gtggctcatg cctataattc caacattttg gaaggcccag   36212
gcaggaaaat ttcctgagcc cagaccagcc taggcaatat agtgagactc cgtctctaca   36272
aaaaatgttt ttttttttgt ttgtttgttt ttaattagct tggtgtagtg gcacatgctt   36332
gtaatcccag ctacctggga cattgaggtg ggaggatcgc ttgagcccag gaagttgggg   36392
gctgcagtga gctgtgatca tgtgccactg atctccagcc tatgtgcctg tataacagag   36452
cgagtctctc tcttaaaaga aaaaagaag  aagaagaaga agaaaagata accatatacc   36512
tccattatta agcaatttag ctaactggtg atattttggt accatacaaa taacaaatta   36572
tttgtcagtc ctaatgattt tagcatctgc tgatgattgt tgcctaaccc aattattaaa   36632
agttgcaaac atcataattt tctagttata ttatgcactt acattattta acagacatgc   36692
ttttgtaaaa taaatagcgt ttcctcatta gcccaggcta tttgtttatc ttgaagttta   36752
gctcctacta caaaggcaag ataaatgctt ttctctttaa ttaccagttt tcagaataca   36812
cacttggtgt actctgcact acctgctttt tttgtccccct ccgctttctc ttttttaagt  36872
atcagattag actcacagat ttttaaatat tccatgtgtt ttagttggag tcatattctt   36932
ttgtctcaac tttagccaaa gagagtcctt taaagttgac tcttatattg tcttgacaaa   36992
aattcattag tcttttgaac gaagcctcaa agcttgactt gttttctagc ataagatgtc   37052
ttagacttac ctacatactt catgcccata cttggaataa accatttctt taaagagccc   37112
aggttccttt tagtggggaa ggcatttaga taccaaaaac tggccactgg gcatcattgc   37172
tctcagagta tcattgccac tagtctctca gtagacaagt tagaaaaata tgtatatatt   37232
taaaccatga gttcatattg ttatttccag tttaattata acattatggg gtaagtaaat   37292
agtatcggat ttttactaag cttctttgat tttgcacttg tatttttttc ttacatagaa   37352
aacctttatt attaacatta aaatatttgt tttatcctac aatatacata caataatttg   37412
aaaaataata cttgaattga tattaatagt aacaacaaca gcactgctgc caaacatagt   37472
ttaaagtttt atttcaggtc ttattttctt cagaatatat cttgctgaga atgtataggc   37532
aaagtattct acacttactt gaaataattg tcttcatgcg gttatgttat acatttgata   37592
```

```
tatagttagg ctcatttgtt tttcattttt tttattttag ggattttttt cctttattga    37652
attttaatat atacaatatt tatatatgca aaatatttaa tcagagaaat cttaattctg    37712
gtcttacgcc tttcatatta ttctgctcca ccctctgtag gtaacttatt atctttctca    37772
tgtttccttt ttggaaacat aaacaaagac aagacaggtt acatgacatg tataccctc     37832
tgcacctagt tttataccnt accttgtagt ttatttttaa gcatgtaaat gttcaatgtt    37892
catgactaaa tttggacagg atcataggaa cacagaattc aaagtgaaat taaaatgggc    37952
ttgggttctt tactttccac tttaaaggtt gtaatgggtg atgtcaggct aataaaccta    38012
ttttcagctt gatctaaagc ttaatactga gcatcaagaa attctttaat aaatataagt    38072
gatatttatt cagacatgta ataaggaaat gttcatgtct tattttttgtg ttagattttt    38132
ttagaatcta cttttgttag agttttataa atacagttag tgtttgagat agaaagagaa    38192
aagaattagt tttcttcctc ttctacctgc tcatgaactt gatttttttc tcccaacaat    38252
tgaagagcca agaaaagggg agattcttaa gagatgggaa atagaatctc atctacccct    38312
gtttccccca gaacagtgaa actgaatctt aagggtaaga tagaatagtg tgtacttaac    38372
ttagatggag aagaaaggct gccaaaatga gatctgaagc gctattacaa atatttccat    38432
cgttactgta cttcagaatg aattacaacc gtaagttttt ttacttcctc attcataaat    38492
ttgattattc cttataccac ttctcagctt tcatcattct ttattgtact tttctatgta    38552
atgtttgcct attatacagc aacttaagag aactgtaagt ttggacattt cattttggtg    38612
ttgataatag aatatctttg aatagttcta tagttgatga gtagaaccat gaaccaagta    38672
acttaaagtc cttgatgtta tttattacag agaactataa tagaagctct cccgctaatg    38732
tttccatcat gtgtacaaaa agttttcttg ttattaaagc tagtccgttt aacttacaat    38792
aagcataaat agctaagctg tgaaagttac ctgtgataat gctaattttc ccatttatta    38852
aaaggcaagt tgttttccga tcataagaaa tttagaaaag ccatccaaag ataaaattccg   38912
agtgatatat tcctgctgtt tgttatgttt tctcaaatta attgagtttt attttacaat    38972
gacaggagtt attaaagtat tttatttta ttatgattaa gattttcaaa gtaacatttc    39032
ttatatgaaa gaaattatgt taatgcatgt ttttcttaca tgggaaatca tatatttaa    39092
aaatgatttt aaaattcgtt ttactttaag ttgtattatc tttctcaaaa gtggctagtg    39152
cttgaccaga aaaaagaca ccagcataac tcagtgtatc tttatttaca tag gaa       39208
                                                               Glu
                                                               940 atg gcc att ttc aag att gca gct ctc caa aaa gtt gta gat aat agt     39256
Met Ala Ile Phe Lys Ile Ala Ala Leu Gln Lys Val Val Asp Asn Ser
             945                 950                 955 gtt tct ttg tct gaa cta gaa ctg gct aat aaa cag tac aat gaa ctg     39304
Val Ser Leu Ser Glu Leu Glu Leu Ala Asn Lys Gln Tyr Asn Glu Leu
         960                 965                 970 act gct aag tac agg gac atc ttg caa aaa gat aat atg ctt gtt caa     39352
Thr Ala Lys Tyr Arg Asp Ile Leu Gln Lys Asp Asn Met Leu Val Gln
     975                 980                 985 aga aca agt aac ttg gaa cac ctg gag gtaagtttgt gtgattcttg            39399
Arg Thr Ser Asn Leu Glu His Leu Glu
   990                 995 aaccttgtga aattagccat ttttcttcaa tattttgtg tttgggggga tttggcagat     39459
tttaattaaa gtttgcctgc atttatataa atttaacaga gatataatta tccatattat    39519
tcattcagtt tagttataaa tattttgttc ccacataaca cacacacaca cacaatat      39579
attatctatt tatagtggct gaatgacttc tgaatgatta tctagatcat tctccttagg    39639
```

```
tcacttgcat gatttagctg aatcaaacct cttttaacca gacatctaag agaaaaagga    39699
gcatgaaaca ggtagaatat tgtaatcaaa ggagggaagc actcattaag tgcccatccc    39759
tttctcttac ccctgtaccc agaacaaact attctcccat ggtccctggc ttttgttcct    39819
tggaatggat gtagccaaca gtagctgaaa tattaagggc tcttcctgga ccatggatgc    39879
actctgtaaa ttctcatcat tttttattgt agaataaatg tagaatttta atgtagaata    39939
aatttattta atgtagaata aaaaataaaa aaactgagat agaatatcat aagttacaat    39999
ctgtgaatat ggaccagacc ctttgtagtt atcttacagc cacttgaact ctatacctt    40059 tactgaggac agaacaagct cctgatttgt tcatcttcct catcagaaat agaggcttat    40119
ggattttgga ttattcttat ctaagatcct ttcacaggag tagaataaga tctaattcta    40179
ttagctcaaa agcttttgct ggctcataga gacacattca gtaaatgaaa acgttgttct    40239
gagtagcttt caggattcct actaaattat gagtcatgtt tatcaatatt atttagaagt    40299
aatcataatc agtttgcttt ctgctgcttt tgccaaagag aggtgattat gttacttttt    40359
atagaaaatt atgcctattt agtgtggtga taatttatt ttttccattc tccatgtcct    40419
ctgtcctatc ctctccagca ttagaaagtc ctaggcaaga gacatcttgt ggataatgta    40479
tcaatgagtg atgtttaacg ttatcatttt cccaaagagt attttcatc tttcctaaag    40539 atttttttt ttttttttg agatggagtt tcattctgtc acccaggctg agtgcagtgg    40599
cacgatctcg gcttaacgct tactgcatcc tctgcctccc agattcaagc agttctcctg    40659
cctcagcctc tgagtagctg ggattacagg tgtgcaccac cacaccagct aattttttt    40719 tttttttttt ttttttgag gcagagtctc gctctgtcac ccaggctgga gtgcagtggc    40779
gccatcttgg ctcactgcaa gctccacctc ccgggttcag gccgttctcc tgcctcagcc    40839
tcctgagtag ctggtaccac aggcacccac catcatgccc ggctaatttt tgtattttt    40899 agtagagatg gggtttcacc ttgttagcca ggatggtgtc gatctcctga actcgtgatc    40959
cacccgcctc ggcctcctaa agtgctggga ttacagatgt gagccaccgc acctggcccc    41019
agttgtaatt gtgaatatct cataccctatc cctattggca gtgtcttagt tttatttttt    41079
attatcttta ttgtggcagc cattattcct gtctctatcc ccagtcttac atcctcctta    41139
ctgccacaag aatgatcatt ctaaacatga atcctaccct gtgactccca tgtgactccc    41199
cgccttaaaa actgtcaaaa gctaccggtt acctgaaggg taaaagtcaa gtcccctact    41259
tacctcatgt catctagagc aagagatgaa ctagctgagt tttctgacca cagtgttctt    41319
tcttatgtat gttcttttgt acgtgctctt ttctatatat agggaaccat ttctctcttc    41379
cagttgtttt gctcagtgaa tttctattcc tgtttcaaaa cttgttcagg cattaccttt    41439
tttttcttaa gcatactttt tttaatgaaa caaagtcact cctgtctaca ctagttctgc    41499
atcttataca taggttttgt acatagtaca tatttatatc acatcaaatt atatgtgttt    41559
acatatctgt cttccttaat ggaatataag tcttttgata taaggaacta tttaatttgt    41619
ttctgtgtgt tgagtatctc ctgtttggca cagagttcaa gctaatacat gagagtgatt    41679
agtggtggag agccacagtg catgtggtgt caaatatggt gcttaggaaa ttattgttgc    41739
tttttgagag gtaaaggttc atgagactag aggtcacgaa aatcagattt catgtgtgaa    41799
gaatggaata gataataagg aaatacaaaa actggatggg taataaagca aagaaaaac    41859 ttgaaatttg atagtagaag aaaaaagaaa tagatgtaga ttgaggtaga atcaagaaga    41919
ggattctttt tttgttgttt tttttttga aacagagtct cactgtgttg cccaggctgg    41979
```

-continued

```
agtgcagtgg agtgatcttg gcttactgca acctctgcct cccaggttca agcgattctt    42039
ctgcttcagt ctcccgagta gctggaatta caggtgccca ccagcacggc cggctaattt    42099
agtagagaca gggttttgcc atgttggccg ggctggtctc aaactttgga tctcaggtaa    42159
tccgccagcc tcaacttccc aaagtgctgg gattacaggc atgagccact gtgcccagcc    42219
tgtttttttt tttttaaagg agaccagtga agtttcagga ggagggaaag aaaatttaga    42279
gttactaggg agagagtgat gaagataaga gatgaaagtg gtaataaggg aaatagcaaa    42339
atatcagggt aggtgggaga aaaagagatt tgtaacaaac aataggatta tcctgtgaaa    42399
aaggatgaaa ggaagaaaaa aatggataga aagatattta aaacaccctc agcctcctgt    42459
tttccctcct gtgtattcat agtatataaa actataatta tgtactttac ttaaaaaata    42519
tattattatt accttatcgt gcttatttaa tcatagcatg tcctctttt agtctcatta    42579
ccctgtttgt attattcttc ataacactta atacctgaca ttgtattata tattggctta    42639
ttttccaggt actccactca aatataagtt ctaggatata atttatttat cactgaaatc    42699
cattgcttag agtacctggc atgtagtaaa taggcattct gttttttcaa ataaaaaata    42759
aaggaactta agatatatat ttatgttata tcgccagcct ttttcctcac agctctattc    42819
tgttgtacag aattacctac tttacaattc ctgtgtttca aggggatctc aaatttaacg    42879
tgtccacaat gaactcctga tttctgtttc tctcctagtc attcttattt caatatatgt    42939
tcagttacct aaccagctag tcaaggcaga tactttagag ttattctgta gtcattcttt    42999
ttccctacca tttttgtttt ccaaatgtaa tttatgtgtg tcttcttcat cctcgcagct    43059
ctaacccttg tccaaaccag catcatcact catctggagt tccacaatgt ctttctggct    43119
agtttccctg atttctctat tgaccccttt attctccaca gtgcagccag aatgattgtt    43179
taaaacttcc tccttaaaat ctttaaattg ttttctttta tacgttaagt taaattccag    43239
ttccttgtct tggcatgcca tgccctgcct ggtgtggccc ctgatggtct ctccaacttc    43299
atgttttact actattgact cttatttttg cttactctgc ttgggtgctc cagtcctcca    43359
aatcatttcc tgctccaatc atttcaatca ttttttcctc tcagatctta tagtattcca    43419
aatgcttct tcctttggag catctgggtt tactaataaa tacttcgtac ctcacagttc    43479
agcttaaata tcaattattt ggtggttaag acatccttca accgctctat ctaaatgttc    43539
cttttctatta ttcactggct cagtactctg ttttttatttt cttctaaat gtcaacttt    43599
ttttttttga gtcagggtct cactgttgcc caggctcgag tgcagttgca caatcatagc    43659
tcattgcagc cttgccctcc tgggatcaag taattctccc acctcagcct ccaaaatagc    43719
tgggattaca ggtatgcatc accatgctca gctaattttt tgtgtttttt tgtagagatg    43779
aggtctcact ttgttgccca ggctggtctc aaactcctgg actcaagtga ttctcccacc    43839
tcagcctccc aaagtgctgg ggttacaggt gtgagccact gcacctggtc gatactgact    43899
tttttttttt tttgagatgg agttttgctc tgttgcccag gctagagcgc agtggtgtga    43959
tctcagctca ctgcaacctc cacctcccag gttaaaggga ttcttctgcc tcagtctcct    44019
gagtagctgg gattacaggc aagtgccatc atgactggct aattttttgta ttttttagcac   44079
tatgtttagt actgtgttgg ccaggcttgt ctcgaactcc tgacctcaag tgatccaccc    44139
acctcagcct cccaaagtgc tgggattaca ggtgtgagcc accgtaatcg gccaacattg    44199
acatttttag tagacttttt gtttgtttac ttgcttatta tctgctgcct tccacactct    44259
ggcgaaatcc tgccacccac ccacacacac ataggcactg aatgggcaga actctgaagg    44319
ccagaatttt atatttcttt tcactgtaaa catcatcatc tgtcactgat ggcacactag    44379
```

```
gatgctcagc aactgtgtgc atgaaggaag taagcactag tttgtgaagg ctgcaaaact    44439
cttgagtatt ctaagagttt tggccaaaat gaatgtacag ctttagtggc agaagctaat    44499
actcagaaat tgaggccgta tattggataa cacaggattt ggatgattat tttaaaataa    44559
tattttacat tgtatatatg tgtgtgtgtg tgtgtgtgtg tgtgtgtatg tgtgtgtgtg    44619
tgtatatata tatgtatgta tgtgtattag tccgttctca tgctgctatg aagaaatacc    44679
tgagactggg taatttataa aggaaagagg tttaattgac tcacagttcc acagagctgg    44739
ggaggcctca gaaaacttaa cagttatggc agaagggaa gcaaacacat ttttcttcac     44799
atggtggccg gaattagaag aatgtgagcc gagcaaaggg gaaagcccct tataaaacca    44859
tcagacatcg tgagaactta ctattatgag aatagcgtgg gggaaaccac ccccacgatt    44919
caattacctc ccaccaaatc cctcccatga catatgagga ttatgggaac tatgattcaa    44979
gatgagattt gggtagggac acagccaaac catatcagta tgtatatgta tacaagtatt    45039
atatatatat gtatgtgttt gtatgcatac atgtattata tatggaggaa attctaattt    45099
tgtaaaaaac tggattgtga gttttaagga gatgttatat aaagttaaga caatgtcatt    45159
ttgtggtatt ggtctgaatt acaatgtagt ttcttagtga tattttcct  ttattcag     45217 tgt gaa aac atc tcc tta aaa gaa  caa gtg gag tct ata aat aaa         45262
Cys Glu Asn Ile Ser Leu Lys Glu  Gln Val Glu Ser Ile Asn Lys
        1000                1005                1010 gaa ctg gag att acc aag gaa aaa  ctt cac act att gaa  caa gcc        45307
Glu Leu Glu Ile Thr Lys Glu Lys  Leu His Thr Ile Glu  Gln Ala
    1015                1020                    1025 tgg gaa cag gaa act aaa tta g gtaagtttta tgactctgat aatataaaat       45359
Trp Glu Gln Glu Thr Lys Leu
            1030 gattaacatc taataatgaa tatttcttat ttaaagttcc ttttttatgc tagattaaaa    45419 ggaagtattt tgactaaaaa aagaaagaac tttctgccta ataatttaac ttaggcagat    45479 gaataatcct gtacttaacc ccaccaaagt ttagttttca gtccttaagt tagatttgtt    45539 tctaatgaaa tcatatatgt taaaaattta tgactaagta ttagctactt tgaaccgttt    45599 aacaattaaa actgatgata ttttattaat ggtattatga gttctttcac tgagtgcaag    45659 ttatattagt tatatatcac ttgatatttt taaattaaaa gataccagga aacagcaaag    45719 aaaatgtgaa aagaagttgt atttctcata gttttactac tatattactg tatattttg    45779 ctcctatatg cttacatatt ttatatattt taaattatta taaacatggt tttatactgt    45839 atttagatag taatatcaaa aatattttta tggccggcgc agtggctcac acctgtaatt    45899 ccagcacttg ggaggctgag gagagcagat ccctggggt  caggagttcg agaccagcct    45959 ggccaacatg gcaaaacccc atctctacta aaagtacaaa aattagccag gcgtggtggc    46019 agttgcctgt aattccatct actcaggagg ctgaggcagg agaattgctt gaacctagga    46079 gtcagaggtt gcagtgagcc aagatcatac cacagcactc cagcctaggc gataagagtc    46139 agactccgtc tcaaaaaaaa aaaaaattt  gttttattca tcatacttat aaatacttat    46199 acaatagcct aatgtgtttg agtgattaaa tcactagctt tttatatttt tgctattgct    46259 tatagtgcca cagtgaacat tttcatgtat atctaacaga gatattactg tctcagaagg    46319 tattgaaatc tttgttgctc tcattagagt tttccatatt aatttttcaa acagttatat    46379 agtttataag atttttcataa ttttatctca tatattgtgc ttcataattt tcaaataaat   46439 ttgctgcttt cgataatgta ttttcatgta tttgtttcct agacgttaga gctattcaag    46499
```

```
gtttttatta ctaaatagag ctgttctctt aaattggtaa tgagatactt ggtttagaga   46559
agcctaacac tgggaaatct tacataagct acttttagaa atgtaatttt tagctcaata   46619
agagattaaa tatgaattga cttttgtgta gtatttgcat ggaagaaggt accatttaaa   46679
tgaagacatg agagtattac gtacaatttt agtaggttct ttttatttta tcatctttat   46739
ttttaataaa tgctgaattc cctacagaaa ttctttaatt tttacatatc ttgatctctt   46799
tcatatatgg atttatatca ccgaagtttt aagagtgttt ccctattccc tgttgccctt   46859
atatctttgt ttaaaaatgt cacatcatta gctttttttc atctaggaat ttgttagtgt   46919
tgggctgttg tgctctaccc tctctttaag aaaactccaa acccaaaaac atacaagatg   46979
gctagtctgc ttcagccttt tgtgatgtgct tttctcttct aatcagagtt tagcacaata   47039
cagaatggag aaggactcct ttatatattg gtatttattg cagtattttt ctacatggtg   47099
cctaaggtta cttgaatgag tctttattcc ataatgaact gatttactaa tgcttttagc   47159
acctgttagt gatccattat tgttagttac ttgattactg cttgccacag ctattctaaa   47219
ataatacatt ttaaagataa atacagaaca taatgaagta cttttttaaaa ctgagataga   47279 gaccaatttt ttttttcagga aatgtatatt actttgagaa aactcagtta taaaacttga   47339
acttatgaag ctgaaaaac aggagggggc attattggta ttgtaaaagg ctgtttacaa    47399
agtgagttgc tgcttagttc ctttaagtaa ttggctaccc taaacacatc agttttaagt   47459
tgctgaaaag caaaacactc taccaaattt tgttttttt ctagaccatg tttacaaagc    47519
aaaagtatgt tttcttcccc cccctcaaa aaatgactaa tgacactcct atgcgatgcc    47579 ttttatggt aaattgaggc ttttagttct ctttccatt agccacagac ttttgtgtcc     47639
aaagacaagc tgcgtaactg catatataag gttaaggcat aactactaat aaaagaatgt   47699
aaaatatttg atattaggtc tgtacaaaga ccaaataata ctcatgatta gacaagatta   47759
tatttggtag aatctatcca tcatatggct tcagatttta cttttcagct tggctttgtg   47819
agactttaaa aatcaagtca ttgcacttat attcacaaag tcacattgct ttactgcatt   47879
gcttctcata cagtttatct cctttcagta aaatgtttac ttgccatttt taaaatttct   47939
tatatgtgac acttctacac taagtccttt atgttgttag ttccacaatt ctgtgaggaa   47999
taggtttttt tttttaatca tttgattgat gaagaacatt aagttccaca gagattaaat   48059
ggtacaggca tcacacaggc aggaagtaac agagctaaga ttagagtcca ggtctgatgg   48119
aattcagaaa gctaatgtgc tttccatgga actataatgc tttctaatat acagcatcta   48179
aaatatctga ggtaattta atataaacag catgagattg acttaaatat tattgcatgt   48239
``` ag gt   aat gaa tct agc atg  gat aag gca aag aaa  tca ata acc aac   48285
   Gly Asn Glu Ser Ser Met  Asp Lys Ala Lys Lys  Ser Ile Thr Asn
       1035             1040                 1045 agt gac att gtt tcc att  tca aaa aaa ata act  atg ctg gaa atg       48330
Ser Asp Ile Val Ser Ile  Ser Lys Lys Ile Thr  Met Leu Glu Met
1050             1055                 1060 aag gaa tta aat gaa agg  cag cgg gct gaa cat  tgt caa aaa atg       48375
Lys Glu Leu Asn Glu Arg  Gln Arg Ala Glu His  Cys Gln Lys Met
1065             1070                 1075 tat gaa cac tta cgg act  tcg tta aag caa atg  gag gaa cgt aat       48420
Tyr Glu His Leu Arg Thr  Ser Leu Lys Gln Met  Glu Glu Arg Asn
1080             1085                 1090 ttt gaa ttg gaa acc aaa  ttt gct gag gtttgatatt ataagttta           48467
Phe Glu Leu Glu Thr Lys  Phe Ala Glu
1095                 1100 tcatacaatt atagaataaa gaattagttt tggtagacat tgtattattg ttaagtggtt   48527

```
tgtctggatc tctgaaatat cttattaata tagtgcctat gttttgtgta ataaataaat   48587
aaaagattta aatctgaatt gtttaaaagg aaagcagata tttctgtaag tttttctcac   48647
caatgttata ttattagatt taatttatga aatgttattt actaaacaat ggaattgcct   48707
ttcaccacca tcccttcatt taacaaatat ttattcattg cctattacat gtcagaccct   48767
gtgttgggac tggcagtata gcaagaaaca aaatagacaa taatctctac tttcagggac   48827
tttacattct aattggtggt tttatatatt tttgatgtgg tcagaatcat taaactgtgt   48887
ggcagtaaat atagtttgca agtatttaac aatttatgat taaacacaac tcttacagtg   48947
tttgcttacc ttgagattta atatatttc aaagcattta tatcattttt gttttaacta   49007
tgtcactaaa tctatatgag taagatttta ttaactcatt tggatttatt tatagatgat   49067
acaattgaag taaatataa tgagcagatt gcattctaag caaagtaaga atattgcaag   49127
ttcagatatt attagataat gagttgccta ataaaaatga cttttggtgg attggaatat   49187
aaccagagtt tccatagttt gtttctgatt ctttcatatt ttttaccctc cttcagtctg   49247
ttcttaacac ttcacactta atataatatg tgaactaagg ccaagtaaag aggattgcag   49307
tactttaaaa gctaaattac aaagaaaacc tcaccaaaaa ttgatgtatc tgaacatttt   49367
ttgttacatt tccttag ctt acc  aaa atc aat ttg gat  gca cag aag gtg   49417
                   Leu Thr Lys Ile Asn Leu Asp  Ala Gln Lys Val
                          1105             1110 gaa cag atg tta aga gat gaa tta gct gat agt  gtg agc aag gca          49462
Glu Gln Met Leu Arg Asp Glu Leu Ala Asp Ser  Val Ser Lys Ala
1115             1120             1125 gta agt gat gct gat agg caa cgg att cta gaa  tta gag aag aat          49507
Val Ser Asp Ala Asp Arg Gln Arg Ile Leu Glu  Leu Glu Lys Asn
1130             1135             1140 gaa atg gaa cta aaa gtt gaa gtg tca aa gtaagtgcat ataagcattt          49556
Glu Met Glu Leu Lys Val Glu Val Ser Lys
1145             1150 tagccatttg actagatgta tcttctttaa tttgtcttta agaaacccaa ttacaggtat   49616
acaattctta gtagtaattg atactgattc cttttataa gaacaggatt aagtaatatt   49676
aagatcggtt ttaacagggt taaataataa tattgacgag aataatattg ttaaagagga   49736
agtgacctct caagatttgc atttttaga gttcaggaat attattgcag aaaggtccag   49796
ttcctccaca tattgatttt tggggaagg ggtgatggag gaggaatggt tgtttattgt   49856
atttaaactt aagtttcttc attttaataa gggagtaata gtacctcttc tacctgtttc   49916
ataaggttgc tgtaagaata taataaaaaa ttcagatttt gatttagttt acatttatcg   49976
ggcatctact atgtactagt cacggtgcaa ggtattaaac atatattgac ttgtacaatt   50036
atacttaacc ttgaggttat attttgttt tcattttaca tgaagaaata tgcccagcta   50096
gtttagaaca caaatatat ataaggagta aatactgcgt gctggctggg cgtggtgaca   50156
tgtgcctgta gccccagcta ctcgggaggc agaggcagga gaatcgcttg atcccggag   50216 gtggaggttg cagtgagccg agatcgcgcc actgcactcc tgcctggtga cagagcgaga   50276
ctctgtcaaa caaacaaaca aacaaagaaa aacaaaacaa aaaaccgtg tgccagctat   50336 atgctgtatt tcattctct tttgtaatta ggtgatattt cagtagaaaa gtataaggag   50396
cacttagtta atctgtcaag cataaatagt aaaatatttt tatggcctac tcataaaaat   50456
ataaccattc ctttggagcc ttgatagttc tcttgggaat atcagttttt gacatctttt   50516
tcactatgaa agacccttt ttttaaaaaa attgatcctt tcttctcatg gacctcttt    50576
```

```
gatataaact aacttataat agttcatttt aatcatattt tgttaatcat gcaactggca    50636
atgagagcct ctcatcagta tgaggaaacc tgccttatct ataatactga actaaaatta    50696
ttctaaccca aagcaaagaa actttacatt ttgctttgcc tgtattagct tatcacagta    50756
ttcatgaggg aatttgaagg acttattacc attaggctat ctcttttttt tttttttttgt    50816 aattttatta aatgcatgtt ttgtttcttt tcacattact gataacttgt agattaaaac    50876
aaatcaaaac atgcattaat ccatctaagg atcctagaaa ttttacattt ctgtgttctt    50936
aactgtgtga tggtcttaga taaatgtact aaatacctta tcctagcata ttccaaatta    50996
tgacaataaa tgttttatgg aaaaagtat gggaacagaa gttctttggc tatatacatt     51056
tggaaaatac tatatagtaa gtatgatttg agataattat atatgataga acctctggga    51116
gcactgaata tatgttagga atattcaaga gggaggaggg atgttgagaa tgaagttttt    51176
tttatatagc aaacatgata acctctgatg gaattatgtt tcatgaaaca gtttaggaaa    51236
tcctgtttta atatttcata caagaagag atagatgctg aaaacgaatg gcttttgaa      51296 aaagggtcta gaaattttga attttggcat ttacttagaa agtgtactta attgttcctg    51356
aaatacctta tcatttccta g a ctg  aga gag att tct gat  att gcc aga      51405
                        Leu Arg Glu Ile Ser Asp  Ile Ala Arg
                                                    1160
                                  1155 aga caa  gtt gaa att ttg aat  gca caa caa caa tct   agg gac aag       51450
Arg Gln  Val Glu Ile Leu Asn  Ala Gln Gln Gln Ser   Arg Asp Lys
    1165                 1170                               1175 gaa gta  gag tcc ctc aga atg  caa ctg cta gac tat  cag gtatgtcag      51499
Glu Val  Glu Ser Leu Arg Met  Gln Leu Leu Asp Tyr  Gln
    1180                 1185                  1190 tattggctct tctacataga atccactttt ttccctaaat ttacattaga tgttgggagt    51559
gggatatgtt atacttttg tttgtttcga gatagggtct cattctgttg cccagggtgg     51619
agtgcagtgg tacattcaag gctcattgca gccttcacca cctgggttca ggtgatcctc    51679
ccacctcagc ctcttagaca gctgggacta caggcacgtg ccaccacacc taatttttt    51739 gcattttttg tagagacagg gtttcaccat gttgcctagg ctggtcccaa actcctgggt    51799
taaaatgatc tgcccacctt gacttcccag aatgctggga ttacaggtat gagccaccat    51859
gctgggccat tgttacattt ttaatcaaaa gatataccaa ccagaggctg ttattcttgt    51919
tagttggaac ctgattagaa agctctttaa tttgaaatat tgttcagtaa tccagtacag    51979
catttaaatg cctatagatg aattatgctg ctgatcaaaa ttaggacact gagaattgta    52039
gttagtaaat ctttaataac aatatttct cttgtattta tatgtaactt tttacatatt    52099
cttacgttat atatgttggg aattataaaa acatacacat tgtcctgatc agtattatgt    52159
tacttgcaat ggaggttaaa aaaaaactgt aacagtcagg catggtggct cacgcctgta    52219
atcccagcac tctgggaggc cgaggcaggc ggatcacgag gtcaggagtt cgagaccagc    52279
ctgaccaata tggtgaaacc ccgtccctac taaaaataca aaagttagcc aggcgtggtg    52339
gcatgtgcct gtaatcccag ctacccagga ggctgaggca ggagaattgc ttgaacccgg    52399
gaggtggagg ttgcagtgag ccaaaatcac gccattgcac tccagcttgg gtgacagagt    52459
gaaactctgt ctcaaaaaaa aaaaaaaaa acaccagtaa catacccact gttattcagt     52519
tacatttgga ttttaagttt gtttgattct aggttttttc tttttacagtt ctttggtaat    52579 tatttgtatt aaagcaaagt tacatttttg tagatctcat gtgccactgt gttaaaactt    52639
tgcttagtaa attgtgaatt ttaaatctgt gataactttc actggaaaaa tttgaaactt    52699
actacaaata tatattttt ttaatatcag gca cag tct gat  gaa aag tcg ctc     52753
```

|  |  |  |  |  |  |  |  |  |  |
|---|---|---|---|---|---|---|---|---|---|
|  |  |  |  | Ala<br> | Gln<br> | Ser<br> | Asp<br>1195 | Glu<br> | Lys<br> | Ser<br> | Leu<br> |

```
att gcc aag ttg cac caa cat aat gtc tct ctt caa ctg agt gag       52798
Ile Ala Lys Leu His Gln His Asn Val Ser Leu Gln Leu Ser Glu
1200             1205                 1210 gct act gct ctt ggt aag ttg gag tca att aca tct aaa ctg cag       52843
Ala Thr Ala Leu Gly Lys Leu Glu Ser Ile Thr Ser Lys Leu Gln
1215             1220                 1225 aag atg gag gcc tac aac ttg cgc tta gag cag aaa ctt gat gaa       52888
Lys Met Glu Ala Tyr Asn Leu Arg Leu Glu Gln Lys Leu Asp Glu
1230             1235                 1240 aaa gaa cag gct ctc tat tat gct cgt ttg gag gga aga aac aga       52933
Lys Glu Gln Ala Leu Tyr Tyr Ala Arg Leu Glu Gly Arg Asn Arg
1245             1250                 1255 gca aaa cat ctg cgc caa aca att cag tct cta cga cga cag ttt       52978
Ala Lys His Leu Arg Gln Thr Ile Gln Ser Leu Arg Arg Gln Phe
1260             1265                 1270 agt gga gct tta ccc ttg gca caa cag gaa aag ttc tcc aaa aca       53023
Ser Gly Ala Leu Pro Leu Ala Gln Gln Glu Lys Phe Ser Lys Thr
1275             1280                 1285 atg att caa cta caa aat gac aaa ctt aag ata atg caa gaa atg       53068
Met Ile Gln Leu Gln Asn Asp Lys Leu Lys Ile Met Gln Glu Met
1290             1295                 1300 aaa aat tct caa caa gaa cat aga aat atg gag aac aaa aca ttg       53113
Lys Asn Ser Gln Gln Glu His Arg Asn Met Glu Asn Lys Thr Leu
1305             1310                 1315 gag atg gaa tta aaa tta aag ggc ctg gaa gag tta ata agc act       53158
Glu Met Glu Leu Lys Leu Lys Gly Leu Glu Glu Leu Ile Ser Thr
1320             1325                 1330 tta aag gat acc aaa gga gcc caa aag gtaaacattt aaacttgatt         53205
Leu Lys Asp Thr Lys Gly Ala Gln Lys
1335             1340 ttttttttta agagacagta tcttgatctg tttcccaggc tggagttcag tggtgcaaac  53265
atagctggaa ctcctgggct caagggactc tctagcctca gcctcctgag tagttgtagc  53325
tggcagtaca ggtgcacacc accatacccta cctaattttt taaaattttt aattttttt  53385
gtagagacaa ggtctcactt tgtcacccag gctggccttg aactcctggc ttcaagtaat  53445
cctcctgctt tggtctctca aaagtgctga gattacaggc atgagccact gtgcccagcc  53505
aattttaaat tcattatctt caaaagagtt acatgataat ttcttaatat atgcctatat  53565
gaaaaatgct taagatacaa attccaatta tgattcatta atttagattt tataacttag  53625
cagtgttggc tatttgaatg tctattatac gtaaaaataa aattaggctt ttctaaccaa  53685
agattttagt gggaatgttc agattgtata atagcaaaga attttaatta ctataggaaa  53745
atttatatta attaaacact aattattata tttaaacatt gtagtagtta tcagttgatt  53805
tctactgttc ataattatct ttgatctaca agtagtgggc ccacatttac ttttaatatg  53865
gtttaatctt catttagaaa gaattaaatg aaaaataatt atcttgcaac tacatcctgt  53925
tctctaggct agaaacattt aggatttctg tttttgaaag taataccaaa gttccaatga  53985
cctgcttata gtcagtgttc aataaacgta taacaaatga aagtgaatat tagtgatgtc  54045
cattccaaca taatttgaag attttttattg taaaatccca catatttgta gaaaagtcta  54105
tggaaatcct aaataagatt ttgtcatgta gtttgacaaa agataacatt gtgtcttatt  54165
ttatttttaga atggccatta cttttcaatta aaatcattat catcaatgga ggaatgttat  54225
ttgttaatat agcatttata tttgtgtata taaattgtaa atcttag gta atc  aac     54281
                                                    Val Ile  Asn
```

```
                                                        1345
tgg cat atg aaa ata gaa gaa ctt cgt ctt caa gaa ctt aaa cta    54326
Trp His Met Lys Ile Glu Glu Leu Arg Leu Gln Glu Leu Lys Leu
            1350                1355                1360 aat cgg gaa tta gtc aag gat aaa gaa gaa ata aaa tat ttg aat    54371
Asn Arg Glu Leu Val Lys Asp Lys Glu Glu Ile Lys Tyr Leu Asn
            1365                1370                1375 aac ata att tct gaa tat gaa cgt aca atc agc agt ctt gaa gaa    54416
Asn Ile Ile Ser Glu Tyr Glu Arg Thr Ile Ser Ser Leu Glu Glu
            1380                1385                1390 gaa att gtg caa cag aac aag gttttatttt atatttattt cattttttc    54467
Glu Ile Val Gln Gln Asn Lys
            1395 cctaagtttt tttttttttt tttttttttt gagatggagt ctcactctgt cgcccagact   54527
ggagtgcagt ggcgtgatct cggctcactg caagctctgc ctcccgggtt catgccattc   54587
tcctgcctca gcctcccaag tagctgggac tacaggcacc cgccaccgtg cctggctaat   54647
tttttgtatt tttagtagag acggggtttc accatattag ccaggatggt cttgatctcc   54707
tgacctcatg atccgcccgc ctcggcctcc caaagtgctg ggattacagg cgtgagcccc   54767
taagatttta aacaagaata ttgcacaaat gactatgtta tccttctaat taagtgcacc   54827
ttccattact aattgattat ataataattt gttttttatt ttctaaacta ttctaaaaat   54887
tcatatttat ttagctttta taacagtagt cttaatctta aaaacggcaa tacataagca   54947
acctcatttg gtaagttaat ttttattttg atattggtta tttgactttt cacagttcca   55007
cgtttctact ggctctcact gatagagtaa gaagtcagct tcttatagaa taaagtatat   55067
acttcagaga cagatgaaat tcgtcaaaca tatgactgtc tcagagattg ttcccctgc    55127
ttaaattgtt cttaccctag atacctttgg tatttacact gtcagtgcct gcaggtctta   55187
gctcaaatgt cttaccttat cagtgtatcc ttccagcc acctaatata caacagtaaa     55247
tcctactatc cagattccta aatagagatt aattaactta atttttctcc aaagtgcttg   55307
taaccttctg acgtattaca tacttactgg tttattattg actgtctttc cttcgccaga   55367
atgcaagttc cgtggtgaca cggacttggt tttgtttact gccatgtttg tatttcctag   55427
aatgatgctt ggcacataat atatgtcatc aaatatcttt cgtatagctg aacggatgga   55487
tggatggatg gatggatgga tggatagact gaaatcctta cttcacatct gcctttgtga   55547
tcttacacaa gttacttcac ctctctgagt ttgtattttt ttccataaaa ggaaaataat   55607
tacagttttct tcaatgtgtt gtgaggatta gataagaaaa tatatataaa atgcctgtta   55667
tgtgcctgat gtcttcgtgt atgtgtctga cacaaattgt ccttttttta g ttt cat    55724
                                                         Phe His
                                                         1400 gaa gaa aga caa atg gcc tgg gat caa aga gaa gtt gac ctg gaa    55769
Glu Glu Arg Gln Met Ala Trp Asp Gln Arg Glu Val Asp Leu Glu
            1405                1410                1415 cgc caa cta gac att ttt gac cgt cag caa aat gaa ata cta aat   55814
Arg Gln Leu Asp Ile Phe Asp Arg Gln Gln Asn Glu Ile Leu Asn
            1420                1425                1430 gcg gca caa aag gtatgaatga ttaatcttgt ttgttactct gtagcatagt   55866
Ala Ala Gln Lys ctagagtgtt aactcacaga atatttcct gtatcagatg taattttaat tgatgttata    55926
ttgtatattt aaaatataag aggggtttaa tctatgtttt atcatacagc tgtaaaaatt   55986
aatagttact ctcaatgctg caactgcttt tttaaaaaac atactatttc ttaatag      56043
```

```
ttt gaa gaa gct aca gga tca atc cct gac cct agt ttg ccc ctt      56088
Phe Glu Glu Ala Thr Gly Ser Ile Pro Asp Pro Ser Leu Pro Leu
1435                1440                1445 cca aat caa ctt gag atc gct cta agg aaa att aag gag aac att      56133
Pro Asn Gln Leu Glu Ile Ala Leu Arg Lys Ile Lys Glu Asn Ile
1450                1455                1460 cga ata att cta gaa aca cgg gca act tgc aaa tca cta gaa gag      56178
Arg Ile Ile Leu Glu Thr Arg Ala Thr Cys Lys Ser Leu Glu Glu
1465                1470                1475 gtaattagaa gaatttgcat tttgattagt gtattatttg gtatgtttgg gggctttct  56238
aaataatatt tctttatgag ggcaatgcat agaatgatga atctattgct aatttcacta  56298
tttttctatt ctcctataat gtttctaata gccaataatg aacagcagat atagttaatt  56358
tgaattcact atttaattat tagttggtac ctttcggtac actgaatatg aaaggaaata  56418
aaaagcattt aattgtagtt ctatgagcaa tatattctct tatatgatct ctttattctt  56478
acttttttgg ttttattttg aagtgcatgt tacataatct atgaatcaat tttcagttca  56538
ttgcctttaa tgcatggtta aagggttgaa ggtaaattag aaattacttt ctgttttaac  56598
ctagatcttg aatttgatta gtaggtgatc aaatctgtca tcttcattaa attattcaga  56658
aaataatgta aactgaatgt gttttcattt tagttttcat ctaaataaac tgcaaataca  56718
tttaaaatat acataaagaa gttttttcaag taaaactgta cattttttaat catttcagga  56778
aacgtagatt ttcttcagta atttttaagat ttgtcattta tgtgaattgc cattgaatta  56838
cttaatttaa aatactcacc ttaatcctct tgaagagtaa aaattttttct gttttttttct  56898
ctttgtttta ataagctgcg gatttttatat tcgtaattta ttgagtttggg cctctaaaat  56958
tccagttttg tacttaactg acttatagat tagtctccta atgctctgct agtcaatgga  57018
ccaaaataaa agaaataatt tattacatat tcttcctaaa tctagtacca ccatacatgt  57078
ataattctaa actgtaatat ctcaataaag taccttaatt aaattttatg ttcatcataa  57138
caatgaagtt tctagcatat gtaatagtct tataaataag catgcaaata actgctgtca  57198
attagaatta gtcagtttaa ccttattaag tatcaaatgg ctattgtaca tatgatgtga  57258
aaaataaagt gaattttttt tggctaataa ctaatctaaa attcagatga agcattttaa  57318
agggaaaaag atactttaat gatttattat aatttaatca ttgcag aaa  cta aaa     57373
                                                  Lys Leu Lys
                                                       1480 gag aaa gaa tct gct tta agg tta gca gaa caa aat ata ctg tca      57418
Glu Lys Glu Ser Ala Leu Arg Leu Ala Glu Gln Asn Ile Leu Ser
         1485                1490                1495 aga gac aaa gta atc aat gaa ctg agg ctt cga ttg cct gcc act      57463
Arg Asp Lys Val Ile Asn Glu Leu Arg Leu Arg Leu Pro Ala Thr
         1500                1505                1510 gca gaa aga gaa aag ctc ata gct gag cta ggc aga aaa gag atg      57508
Ala Glu Arg Glu Lys Leu Ile Ala Glu Leu Gly Arg Lys Glu Met
         1515                1520                1525 gaa cca aaa tct cac cac aca ttg aaa att gct cat caa acc att      57553
Glu Pro Lys Ser His His Thr Leu Lys Ile Ala His Gln Thr Ile
         1530                1535                1540 gca aac atg caa gca agg tta aat caa aaa gaa gaa gta tta aag      57598
Ala Asn Met Gln Ala Arg Leu Asn Gln Lys Glu Glu Val Leu Lys
         1545                1550                1555 aag tat caa cgt ctt cta gaa aaa gcc aga gag gtattttatt          57641
Lys Tyr Gln Arg Leu Leu Glu Lys Ala Arg Glu
         1560                1565 atattatgag ttatgctgtt atccattagt tttttttaagc aaatgctaaa tattatttta  57701
```

```
ccctaaagtg gtatttcttt tcttgctttc aaatgattct atttaagaat tgttacttgc    57761
atgtgattgg attacacctc tgtcagtaaa actggaagtt tgtgtacatg tatctttcta    57821
ttatacactg actaaaccac gagtagctat catggtgaaa tcatatgatt ttgaaaaata    57881
ttttaattga gtttataggt gaggattgag gcaatagggt ggaatgaaat atatcacacc    57941
ggtaatcagt agaaatcaga tttgttagaa cttcgtgggg gaaagctaac atttaatttt    58001
ttctagaagt aagttaaaag atgatagata catgtcattc taatgttaag aataaattat    58061
gaactgaggc tgggcttgtc aacttgaaca ttgtctgagg ggacatgcat accagtctag    58121
atacatacat atatggagat actgtttctt cctcatctca aaggaatttt agaagattga    58181
agagaaaata tataaggtct tcaaaatgtg aatttgtttt aatcacaatt taagatatag    58241
tttcgatttt ctgtaaaaca g gag caa aga gaa att gtg aag aaa cat gag     58292
                         Glu Gln Arg Glu Ile Val Lys Lys His Glu
                         1570                1575
```

| gaa gac ctt cat att ctt cat cac aga tta gaa cta cag gct gat | 58337 |
|---|---|
| Glu Asp Leu His Ile Leu His His Arg Leu Glu Leu Gln Ala Asp | |
| 1580 1585 1590 | |

| agt tca cta aat aaa ttc aaa caa acg gct tgg gtaagattct | 58380 |
|---|---|
| Ser Ser Leu Asn Lys Phe Lys Gln Thr Ala Trp | |
| 1595 1600 | |

```
aagaactttg ttccattctt tattgatttt tgtgaccatg taaattaaaa ttcagctctc    58440
ttcttttttg gaatggaagt taccctttt gttgccaaaa taatcttctg aaaacatagc    58500
tctgatcatt cttcctcctg tagctcaccg ctgttcacaa aattatattt ataattctta    58560
gccatgtact caatctgcta tgaacctacc tgcctttctt ttcaaattct actcactgtg    58620
agtttagcta tatctaactt ccagaattca gctcatattt gcctcttttg accattctgt    58680
tccatatgta tgaaatgaca tgtctttcat ctttttaatgt gtaaccttag catatttgag    58740
cattacctcg ttaattcggt caacacttat tgatctcctg ctacgtgcag acattttgct    58800
agctattgta aatacaaata ataaagtctg catttcctgt cttctttaag ccttcattgc    58860
ctattaaatc attacatttt agattagata ttatatttg atcatttgag gaaccaaatt    58920
aaaaatatgg aataagtatg gcattgaatt atacatgcct attgctaata tattcatatt    58980
```

| ttatag gat tta atg aaa cag tct ccc act cca gtt cct acc aac aag | 59028 |
|---|---|
| Asp Leu Met Lys Gln Ser Pro Thr Pro Val Pro Thr Asn Lys | |
| 1605 1610 1615 | |

| cat ttt att cgt ctg gct gag atg gaa cag aca gta gca gaa caa | 59073 |
|---|---|
| His Phe Ile Arg Leu Ala Glu Met Glu Gln Thr Val Ala Glu Gln | |
| 1620 1625 1630 | |

| gat gac tct ctt tcc tca ctc ttg gtc aaa cta aag aaa gta tca | 59118 |
|---|---|
| Asp Asp Ser Leu Ser Ser Leu Leu Val Lys Leu Lys Lys Val Ser | |
| 1635 1640 1645 | |

| caa gat ttg gag aga caa aga gaa atc act gaa tta aaa gta aaa | 59163 |
|---|---|
| Gln Asp Leu Glu Arg Gln Arg Glu Ile Thr Glu Leu Lys Val Lys | |
| 1650 1655 1660 | |

| gaa ttt gaa aat atc aaa tta ca gtaagtcttc gaaatgtatt | 59206 |
|---|---|
| Glu Phe Glu Asn Ile Lys Leu Gln | |
| 1665 1670 | |

```
gtaaaaatag gcaaatgata agtgatataa tgaagataaa cataagtgtt tgctatgcca    59266
ggcactgttc taagactttt aagtatattg tctcattttt atcctcagga ctgctggtta    59326
catatgttat cattttcccc attttaaaga gaggatatgg cctcaggaat gcttaatagc    59386
atgtctgggg gtagatggga aagccataat ttgaaactag tcagtctgac tcaaaagcca    59446
```

```
atacaaattc ttttccagaa tctcattttt accttctttg agcctcagtt tcatcttatt    59506
tatttatttt tattttttgag acaaggtctg gctctatttc ctaggctgga gtgcagtgac   59566
ataatctcag ctcactgcaa ccttgacctt ccaggctcaa accatcttcc cacctcagcc    59626
tgcagagtag ctggcactac aggcaggtgc caccacacct gggtagtttt tttgtatttt    59686
tgtagagaca aggtttctcc atgttgccca ggctggtctt gaactcgtga gctcaagtga    59746
tccgcccact tcggcctccc aaagtgctgg gattacaggc ctgagccatt gcacccagcc    59806
tcatcatctt taaaatggaa ataataatac ttaccctggc cctttcaggg tggttatatg    59866
aaggtcaaat tataccgtgt atgaaagtaa tttgaaaact gtaaaataac atacagatag    59926 aaaactttg attacacact tataagagtg tctgtcatat aatagagatt ctaaacattg     59986
ttcaaccact ttatcagaac gtagattta aactcaaaat aggtttatag ttaggtagtt     60046
tctaatcatt ataatattat ctctatgggc ctaaatttta ttatctgaaa aaacatgaga    60106
aaattgaact gcttgactta taattccatt tcagctctca agccctgct agagtctttg     60166 attctttact cacttattca aatgcctctg acagaattaa cactattttt gctttgctaa    60226
ggagctgcca ctgttaagaa attactctct aaaagaaaga aaattggcaa cagcatatgt    60286
gtattttcag tctcttttcc tcactctatt aaattttgta caagagatgt tattttggt     60346 ctagtaaatt tctgtcatgt tttggagtat aaaattactt gtgcttttgc atctaatttg    60406
tgggtgtaga aaatcataat cttttgaaat accttatata atacattttt ttgccacagg    60466
aaatacttga agttattgtt gtgtaccta cgtcattta gtccaaaatt atacttgtgt      60526
tctctgtgtg catattttga tatgtattag gagattatgg atctgtgtga tttcttaagt   60586
aaatcctgat attttcacaa tttgatgatg actcttaaa gttagactta agttttgcca     60646
aaagcaagaa gcctcaaaga gtaacatttg ttcatgtctt aacactatct ccctcttatt    60706
ggtcagaatc tcagtatgga tgcagtgtcc atatgcacaa caatatatta attcagttta    60766
acagacttaa tgctgaataa gcaataagat taattgaatt aactaaatct tttgatagta    60826
tccacttcca tatatatagt tatagatata atgctagtga atttgaacca taaacaaatt    60886
aataatacat gtgatttctg tgaaatttta tattagtctt ttcaatatgt caatataggg    60946
cagtatttct caaatataga ggatcagttt ttcaccattg tccctcttgg ggacatttgg    61006
cgatgtctgg agacatttttt gattgtcatg gctcggggt gctactggta tccagtgggt    61066
agaatcaaaa gatgctgcta acatcctat catgcacaag gcagccccac caccaacaaa    61126
gaattatcca gtcaaaaatg ttactagtag tatggttagg aaactatcat atagaggaag    61186
caatcacatt ttacaagagc cataatattt aaaatgcctt tttgttcatt ctctgtatat    61246
ttgactagag tcacaaaata acttgataag attgttgcca aaaatattag aaactagaag    61306
aaaaatgtgt tgttaagtct aagagtagtt aaatgaaata aagaattatt cttctttgga   61366
tttggatgcc tgcatcaaga tttagattgt aaggatactt aggactgaac atttgctcta    61426
tatgaaattt gtattaatca aggtatgaat tgcagcaacc actctattaa ttacatatgt    61486
ttggccaggt gtggtggctc acacctgtaa tcccagcaat tgggatgcc aaagcgggct     61546 tatcacctga ggtcatgcgt tcaaactggc ctggccaaca tggtgaaacc ccatctctac    61606
taaaaataca aaaattagct gggcctgatg gtgcacgccc gtagtcccag ctactcagga    61666
agttgaggca aaaaaatcac ttgaatctgg gaggcagagg ttgcagtcag ccgagattgc    61726
gctgctgcac tccagcctgg gtgacagagt gagactgggt ctcaaaaaaa ttaaaaatta    61786 aaaacacac acacacatat gtttatttac atcag g ctt caa gaa aac  cat gaa    61840
```

```
                                    Leu Gln Glu Asn  His Glu
                                                1675 gat gaa gtg aaa aaa gta aaa gcg gaa gta gag gat tta aag tat         61885
Asp Glu Val Lys Lys Val Lys Ala Glu Val Glu Asp Leu Lys Tyr
        1680                1685                1690 ctt ctg gac cag tca caa aag gag tca cag tgt tta aaa tct gaa         61930
Leu Leu Asp Gln Ser Gln Lys Glu Ser Gln Cys Leu Lys Ser Glu
        1695                1700                1705 ctt cag gct caa aaa gaa gca aat tca aga gct cca aca act aca         61975
Leu Gln Ala Gln Lys Glu Ala Asn Ser Arg Ala Pro Thr Thr Thr
        1710                1715                1720 atg aga aat cta gta gaa cgg cta aag agc caa tta gcc ttg aag         62020
Met Arg Asn Leu Val Glu Arg Leu Lys Ser Gln Leu Ala Leu Lys
        1725                1730                1735 gag aaa caa cag aaa gtaagtaaca acagaaaatt atcaacattt aggaaaaata     62075
Glu Lys Gln Gln Lys
         1740 tgtggtagat tgcttttaga gaagatttgt aaatttataa aagatggtag tataaatctc   62135 cgtgttgtaa taaaaagtat gagctttatc ttatgctgtt aaacaaggta ttttagacaa   62195 tgctgttttt gtgggcagat atagtccaat ttatcttttt atgttttcgt caatctgatt   62255 tgtgaattat ctatatgaag ttaggaaaaa tcttaatgta cattacaaaa atataatata   62315 tattacattg tattttcttt ttttctactg gaatttatg ctactgaggc tattttttaac   62375 aaatgaacaa ttttgaacaa tttgagggat tgagggaagt atgataatga caaaaaggga   62435 tgaaaaaagg gggtcataga gatgttttg tgagaaggag ttggtcagtg tattctgatt    62495 tattagggtt tttttagtt tatctcagat ttgatctatt taaattgttt tagaagatgc    62555 tggtgttttt ctgtgctagc tatgaaattt atgggtaaac tttaagccctt tcctagtcct  62615 tttgttgtct acctaaattc aattaatttc atatggaagg atgtagtaag tgagtaatat   62675 aaatatctaa aattggatgt tgaaaacaa aacatacctg tttttgtaa tagcttgatt     62735 taatgctgag ttctcaaaat cattattaag attttgaact ttcacattca atgtggaaag   62795 aattgagtgt aattacaaaa gatttatttg aaaaagttga gttgttaatt tgtgaaatat   62855 gttccattaa actcataata ttttagaaaa atagtaggaa gtaataaagc ttgtttattt   62915 tttatatcat atattcatat aaaatgtcag ttttccttta aaattacat ttttttttg     62975 gttaattttt ag gca ctt agt  cgg gca ctt tta gaa  ctc cgg gca gaa     63023
              Ala Leu Ser  Arg Ala Leu Leu Glu  Leu Arg Ala Glu
                      1745                 1750 atg  aca gca gct gct gaa  gaa cgt att att tct  gca act tct caa      63068
Met  Thr Ala Ala Ala Glu  Glu Arg Ile Ile Ser  Ala Thr Ser Gln
1755                 1760                 1765 aaa gag gcc cat ctc aat gtt caa caa atc gtt gat cga cat act          63113
Lys Glu Ala His Leu Asn Val Gln Gln Ile Val Asp Arg His Thr
1770                1775                1780 aga gag cta aag gtgaacatca acacgtgtta atgtaacaaa atttctgata          63165
Arg Glu Leu Lys
1785 attcctattg gaagagaatt cactatgata tatagtaatt tgttgatga atagggaatt     63225 tataatgcac tgttggtggc tagacataga cacacacatg cattttttcaa caataagtct  63285 ctttatgata ctcatttact gattatcatc ttggggatta ggaaggata ggccattatg    63345 aactactgtt tctaatgaaa ttaaatttaa gaaatatttt acttaggatt tttttaaga    63405 ctttattatt tttttagagc aatttaggt tcacagcaaa attgagagga aggtacagag    63465
```

```
atttcctgta tatctcctac cctgaaagtg gtacatttgt taaaattgat gaacctatat    63525
tgatacatca taatcaccca aagtccaagt ttacctctat tttagctctt ggtattttac    63585
actctgtgtg tttagacaaa tgtataatga tatgtatcca tcattatagt attatacagg    63645 gtatttcac  tgccctaaaa atcttctgtg cctctcttct tcattcctcc ctctgcacct    63705
caccaaaccc ctggcaacca gtgatctttt tactgtctcc atagtttcac cttttccaga    63765
atatgttata gatggaaaca tacagtgtgt ccccatcatt ctcaccatag acagctagg     63825 aactcctttc tagtggcata catattgtct agtattgtaa gttaccctt  tatatcttat    63885 ctttgtaaac taggttagaa attacttcaa gtcagagatt tgttctgtac tactcttatg    63945
cttcatagtg tttaaaacgt tgtcatatat attgttatat acttgtttgt ttaattaatt    64005
cagccaaaat gaaacgtgca tatttgataa aattttgttt gtgggtgttt gttgaagatg    64065
aattgcttta cactagttt  ttttttttt  ctcaaagtcg acttttttcc tcaaggtaga    64125
cttgacatga atatgaaaa  atatatgtag tttgtggtta ttttttttct cttgtgtact    64185
taaaaattca gactgaattt ttcttataat ggtatatttt ctgttttatg ttcctttat    64245 cattgatact tcttgaagag tcatgaataa taccttctt  tttctcttat tag aca       64301
                                                              Thr caa gtt gaa gat tta aat gaa aat ctt tta aaa ttg aaa gaa gca           64346
Gln Val Glu Asp Leu Asn Glu Asn Leu Leu Lys Leu Lys Glu Ala
1790                1795                1800 ctt aaa aca agt aaa aac aga gaa aac tca cta act gat aat ttg           64391
Leu Lys Thr Ser Lys Asn Arg Glu Asn Ser Leu Thr Asp Asn Leu
1805                1810                1815 aat gac tta aat aat gaa ctg caa aag aaa caa aaa gcc tat aat           64436
Asn Asp Leu Asn Asn Glu Leu Gln Lys Lys Gln Lys Ala Tyr Asn
1820                1825                1830 aaa ata ctt aga gag aaa gag gaa att gat caa gag aat gat gaa           64481
Lys Ile Leu Arg Glu Lys Glu Glu Ile Asp Gln Glu Asn Asp Glu
1835                1840                1845 ctg aaa agg caa att aaa aga cta acc agt gga tta cag gtaatttat         64530
Leu Lys Arg Gln Ile Lys Arg Leu Thr Ser Gly Leu Gln
1850                1855                1860 atttaactct gataatgtct gatttacaat atagaggtag tagtttattt ctactttatc    64590
attttatcta tggtatttgt taaaactgac tttcaaatca ctttgattaa tgtaattaat    64650
ttcttttgtg acttctattg tgtttatagt tctagagtag catattagta tgttgtatta    64710
aaatgcagaa gcagctacca gattatctta tgtattaagt gtcatttaga agtatggtc     64770 agtgatagct tcagaaagtt gctattatat aattgaaata tttactgtct attttgtttt    64830
acatttattt gtaaaaatat aaagttacat tttattttt  ag ggc aaa ccc ctg       64884
                                              Gly Lys Pro Leu
                                                          1865 aca gat aat aaa caa agt cta att gaa gaa ctc caa agg aaa     gtt       64929
Thr Asp Asn Lys Gln Ser Leu Ile Glu Glu Leu Gln Arg Lys     Val
1870                1875                1880 aaa aaa cta gag aac caa tta gag gga aag gtg gag gaa gta  gac          64974
Lys Lys Leu Glu Asn Gln Leu Glu Gly Lys Val Glu Glu Val  Asp
1885                1890                1895 cta aaa cct atg aaa gaa aag gtatgtgaag aaacatactg acttatatgc          65025
Leu Lys Pro Met Lys Glu Lys
                1900 ttaaggtagt gacagagtaa gttaaataca tagctgatta acagttaata tactgcctta    65085 atttgatgac ctggctgtat taattctgta ttaatttga  ggactataag cagtattgaa    65145
```

```
taacgtagaa aagtctaagt ttctgttctg taggaattta gagtctactt gaggagatac    65205
ctataatgta actcttattt ggaaattact acatcaattt cattcatctt tctgacatta    65265
gagtacctct gaagttcctt cacaccttaa catattcaac tgtgtatcat ttctctccaa    65325
agtaatcatt tacacaggtt ggtgcttttg acttttggga cagaaagata gacattttaa    65385
gataccccac tttgacccaa ataggtcctt tttaatcctt caggagacta ggctgttatt    65445
tcagatagca aagttatttg gaatatcttc agtatttgca gtaataatca gtaaccaatc    65505
tgctcataga ttaattctgt gggagaaatt gcttaaaatt ttatagttca tagtaaactg    65565
ttttgtaata aaaattactg attgaaataa ccccaaaaaa aactaaaatt ggctaaaatg    65625
cgtgtaatta aatttgttat ggacaataaa ttggagataa cttgttggta acattcaaaa    65685
tatcgaaagt gaactgggaa atgttgatgt tagcagtaat atttgccatt gaagaaaatc    65745
agtatggagg agctatggtt aggaaaattt ttattataaa atttacccag aaaatattta    65805
atgtctataa aataatttca atcacatgaa aatggaaaag aaaattctgt ctttaaaggc    65865
attgaataga aaataggtaa tggaattcaa atttcttaat agagtatgct cccaaaatta    65925
ttttctatga aaattcatta atgtcagtgt aatttattga cactatttgc gtggagtcac    65985
aacatgcttg ctgtcagaag ctttgctggt gaaaactgta agatcaaagt gtccttaatc    66045
ttttggattt ccatctttct aactccctaa ttggggatag gcctgatctt atccctaaat    66105
ggggataggt tagaaactgg tatgtttgtt cctaactggt gtgtttctat accagtttct    66165
aacctgattc ctatcagaat gttttaagag ccttgtggct ttgcctggac tcttctatgc    66225
tacagtttat ttagtttatt tattcagttt attcctcctt aaagtgggaa taatactatc    66285
tgtattgcca gtttctcagg attattttac ataaatgat atgatatgcg gaagtctttt    66345
gtaagccatc acatccatag cagtataaga tattactact aactagaaag agaaaacagg    66405
ggtctatgcc cagtattaaa attggcattc aggaatctag tgagaatatt ttttcaggtt    66465
cattgcttgg gcatttctaa tttatactca agaaatgctt tcatattgtt tggaaatttt    66525
agtacccttt tctctgtaaa cagaatttgt agtctaccta tgtaacaaaa cccaccctg    66585 tgccttgcat ttcattctcc ttagcattta ttactatctt aacatactag acatgtactt    66645
gtcttttgtt catctttttt ttttctttt ttattagacc ataaactttg atggcaggaa    66705
ctttgcctat tttatttatt attgtattcc cagcacctag aacaatcgct ggcacatagt    66765
agatgctcag tatttgttga atgaatataa attttaaat gttataataa tattattctg    66825
aaatctatgc atacgaagct tttggtacag aaaacatgaa aagagaacta ctgccttatc    66885
atccagtctt cttccctctt ctcattcagt ctagaacata acctgttttg gaaaaagttc    66945
tcaaaccata tgtttatctt gccctcaaac cataacaaca atcaatgcaa aagacttctg    67005 tgaccccag aatatgtggg gatttctcca catcagcaag caagcagttg gttttgtagc    67065
agacaccaac tgggtgtcgt ccaattcaat tcatcatcta cctggagata gtgtcagatc    67125
ccacagatat cttacttcga tcaaatcaca agtccaggcc tccgtgactt ccgaagttcc    67185
cacatcccca gccccagct tgggtttga ttaatttcct ggagtggctc acagaactca    67245
gggaaacatt tacttacatt taccagttta taataaaggt tattacaaag gatacaggtt    67305
aagagatgtg taagaagaga tatgggggaa ggggtgtgga ccttccatgc ctttctgggg    67365
tgccaccttc ctctagaaac ctccacatgt tcagttctcc agaacctctc tgaacccagt    67425
cctcttggtt tttagggaag cttcatgaca tcagtatttc ttctcctagg gtatgggca    67485 ggacccctc gtattagggt tttaagaccc acagtcagaa aggcagggga agattacagt    67545
```

```
cctgccttag ggcaggtgaa aggaggatgg gagaaggtca gagagactct tttctgaggt    67605
gtgctcggaa ggcctaacac actcaatatt ataactaaag atgaggacaa gggctatgag    67665
agttataagc caggaaccat ggaaaaaagc ctatatgtaa taacaccaca atacccatgg    67725
taccattcac gtttgttgtt tttctgtttt tcaattgttc tttcagtctt ggttcccttta   67785 atcttaattt agcaagtaat gccaggtggg ataaaattgc ccaaacccaa caaagtactg    67845
tgtgctgcag gattatttaa tgacatacct tatgtccccc actagtattt acatttctgg    67905
gagtacagaa aaattcttgt acatatttca gaaaaatga aattaataac tatcaaccac     67965
ttagtgaagt ttttactttt tttttgaga tggagtttta ttcttgtcac ccaggctgga     68025
gtgcaatggc gcaatctcag ctcactgcaa cctccgcctc ctgggttcaa gtgattctcc    68085
tgcatcaacc tcccaagtag ctgggattac aggtgcctgg caccacgact ggctaatttt    68145
tgaattttta gtaaagatgg ggtttcacca tgttggccag gctagtctca aactcctgac    68205
ctcaggtgat ctgcccgcct tggccccca aagtgctgga ttacaggtat gagccaccac     68265
acccagactg aagttttac attttttaaa gggcacttat tagctgaatt aaataaggta     68325
aaaaattgac tagtattaga gacaagaatt ggagaatata gttctctagt attcgagaaa    68385
gtcgttttga taggacaact aatcttagtg agaatttggc tttatttcat attttttaa     68445 ttttttgaga tgacgtctta ctatgttgcc ctggctggtc tttgaactct gggctcaaac    68505
aatcttcctg cctcggcctc ccaaagtgct gagattataa gcatgagcca tctccccagg    68565
aatttgactt taaccatgg ttctcaaccc tttcagattc aacattccct ttaataaaaa     68625
atataatgtt tcataatttc ccctttacta ttataattga aatgcatagt taacataaac    68685
tctacctact tacataattt caaaaatgtc attatgaatg tcctaaatga aatatatagg    68745
gggaacataa aaggaatatt catatttcaa catgtaaatg ctttggcatg actccattgg    68805
aaaatataat gaactagtca tgtgcttgca ccttcattaa tgtgagttca aagctacgat    68865
tgcagactga cacaaatgtg ttctattggc aactgatggg tcatgatggt attgccattt    68925
gtaatttgat ttccaaaatg gtaaacaaat tgttggtgca gttctcagca aaacaatgtc    68985
tataatctta cctttataa gactgttgta ttcctagaaa acttagtgta tagtaaaacc     69045
attaaaaaat tacttagtgt gaatatgtta gttggagata aattcttagc tcagaccagt    69105
gtaagcagaa ttttttactg tattaatatc cagtagaaca tttgaaagtt gttcagtgca    69165
tgagactatt ctgcattgga taggctttct ttggctcctt tatcatagtt ataataaacc    69225
atgacaccta cccctgaaat gccctaattc ccttccgttt cttttctttt tttcttttta    69285
gcacttaaaa ctagctaact tactacaaaa tagatttaga tttatttctt gttttgttat    69345
ctgtatcgtt tgctcccttc tccccaatct atctaaccaa ctagtataaa ctagatagta    69405
agattcatga agatacactt ttttatctga ttttattcat ttgttctatt cctattgcct    69465
ctagagtagt acttggcaca tggttagcac taaataagta cctgtcaaat gagtgaagta    69525
atgtgcattg aagacttgaa ggggctctga tgctaggaaa ttgtcatggg ataatagatg    69585
aggttggtcg tttgtacaga ggattcttgt tagaagctta ctctagtcat gattgtatta    69645
gaatcttcat ttaaaggctc ctgaagggtg ttggcattag tcagaactgt ctcccagaat    69705
tttatttgtc ttgtgataga ataaagcata gttagcctaa agagcagttt tcctaatagc    69765
tcggcatgcc caaagattct aggagttata caggttgaac atctaatcca aaaatctgaa    69825
atgctccaag atacaaaatt ttttgagcac caatatgatg ccacaagtgg aaaattctga    69885
```

```
tgtgacctca tatgatgagt cacagtcaaa acacagtcaa aactttgttt catgtacaaa    69945
attattaaaa aatattgtat aatactacct ccaagctatg tgtagaaggt gtatgtgaaa    70005
cataagtgaa ttttgtgttt ggacttggga cccatcccta agatatctca ttatgtatat    70065
gcaaatattc caaaaatatt ttttaaaaaa atccaaattc taaaacacgg ctggttccaa    70125
gcgtttcgta agggatactc aacctgtata gcaaaatgaa catatttaca tattctctag    70185
gaaatattag tttacaattt ttctaggcaa attataattg ataaatcata agaaaatttt    70245
aaaataacac tggtaatttt cctacctcct tcgttattgt tacag aat gct  aaa        70299
                                                Asn Ala  Lys
                                                         1905 gaa gaa tta att  agg tgg gaa gaa ggt  aaa aag tgg caa gcc  aaa        70344
Glu Glu Leu Ile  Arg Trp Glu Glu Gly  Lys Lys Trp Gln Ala  Lys
            1910                 1915                      1920 ata gaa gga att  cga aac aag tta aaa  gag aaa gag ggg gaa  gtc        70389
Ile Glu Gly Ile  Arg Asn Lys Leu Lys  Glu Lys Glu Gly Glu  Val
            1925                 1930                      1935 ttt act tta aca  aag cag ttg aat act  ttg aag gat ctt ttt  gcc        70434
Phe Thr Leu Thr  Lys Gln Leu Asn Thr  Leu Lys Asp Leu Phe  Ala
            1940                 1945                      1950 aa  gtgagtttaa atatcattat aaaactaatt atgtgtaaaa tcctttagtg             70486
Lys acctggaaat tatatagctt tatcatagtt gataatatga gaatggtct agtttaaatg      70546 atcatttatt atctatgatt tacttacttt ttattttctt taaaatctgt tttaaatata    70606
ttgtaacaat tatagatgga ttttcctgtg atctcgttgt aaattagctt atgacaaata    70666
tagggtgtta caattattgt aatttggttt ggtaatgagt atgcaattga aaagccaaac    70726
actgaatggt atatttcatg attctatatt aaattccaca g a gcc gat aaa  gag      70780
                                             Ala Asp Lys  Glu
                                                          1955 aaa ctt act ttg  cag agg aaa cta aaa  aca act ggc atg act  gtt        70825
Lys Leu Thr Leu  Gln Arg Lys Leu Lys  Thr Thr Gly Met Thr  Val
            1960                 1965                      1970 gat cag gtt ttg  gga ata cga gct ttg  gag tca gaa aaa gaa  ttg        70870
Asp Gln Val Leu  Gly Ile Arg Ala Leu  Glu Ser Glu Lys Glu  Leu
            1975                 1980                      1985 gaa gaa tta aaa  aag aga aat ctt gac  tta gaa aat gat ata  ttg        70915
Glu Glu Leu Lys  Lys Arg Asn Leu Asp  Leu Glu Asn Asp Ile  Leu
            1990                 1995                      2000 tat atg ag gtaagctatt atgtggaaat gtgccaccca ttgtaatgaa                70963
Tyr Met Arg aaactggttg acccctagaa attgaaataa taaatgtgtg ttgtcttaag cttgggttat    71023
gttttctttt cccatgtgaa ttgagatatt cctggttctt catatgccac ataatttgg     71083 tgtattttg atcttttgaa tattatattg tgagactctg gttcttgttt aaattctatg     71143
ggaaaatgta gatactttg ttttagcatg caatcggtct aattaggttc aggccacaag     71203
ttccaacctc atttcttggg ctgtggttcc attttttcaaa gccttttcaa tactcttcag   71263
atctgtcctg cctgtgtacc tcacaatagg tgatctggta tgtgagctat gtaccattag    71323
ttcagttctt agaactttg gtattctgat taggatcgat ccatacattt gcagctcaag     71383
agtgagccca gaagttcata aacaacttta tagggtccct ttcttgagct cctccctctt    71443
tgccatctct ctgatacttt gtttccctag ggatttccat tggggctttt agttacccag    71503
tgatgccatg tacttcagga attgcacact tctgcagcca agcaagcaag aggagagtag    71563
aaagaggaag aaaaaaacga cttttacctt accctcttag tatcatagct ctaccaattg    71623
```

```
gagatttccc tcccaaaaaa tattagcttc tgtgagttcc cattgcagcc tctattacca    71683
ctgctatggg atggcttaag ggttggggca tgaaagaaca gatagaagaa aaaaaaagtg    71743
aggtgttttc atattgtctc ttgagtgtta aaagattccc tttctcttta ctcgagctag    71803
aattagaagg tttacctgga gctctctctg tcagtgcaga cacccatctt caggtttcaa    71863
ataatgttgt cttcagggca ggcagtaaca gaataaaaga aaaggtaaat tcatcacctg    71923
tttgctgcta ctttaagtcc tggtattcta ttgtaatctg ccttctactc ctttgcaaag    71983
tcctcaaatg gttgctccat gcatttagga gagagaagat tgaatgtatt tactccattg    72043
tacctggaac cagatgccct tgccctgcat caccccatgt catttcttag cagagccttt    72103 gagattttg tgtgtgtgtg ctttacaatc tctttccaag ttatatcttc tgatacagtc    72163
atggtcgtga aaagcaaaat aaaatcatgt gttaacattt aaaacttttt aattttattc    72223
tgacaacagc taaaactatt taatcttctg tttcgctcat ttcttccaag gtaaacttca    72283
gttggtttta cgtgatttgc tatttcttct tctttgcatt tacaaatgat ctgtgatcat    72343
attactgatc tttgtaaagg gctaatatct acctgcaaca tttggatatg acagtattta    72403
ccctttgtaa atacacattt tctatttatc ttcaaaaatt accattcatt agtctgtgtt    72463
aatgtctgtt tactattgtg tcattatgaa tgtgatgtga acatacgaag ttgaacttat    72523
ttaaacgaac actctcatga gcttctaatc cacattcctt cctttccctt ctaagttacc    72583
atttcttaaa aatctttag aagtttcctt gatagggaaa acacaaatta ttgaggaatt    72643 tttcttctc ttgacatctg tttatagtta ctctcttgtt ccagcagtgg atatttcccc    72703
tccatgtttt tctttgtcta aacatatgtt caaaacaaaa cactttttatt cttctttgca    72763 ggttttacaa ggatcaactt ttagttttga aacctgctat tacttttaga ggccattttt    72823
tttttctcta ataatgtgag ttcatgcggg ctgaagtaat tggaatactt tatagaaaag    72883
attgaatttg tcttctctct gaactctagt ttgaatttct aaattttatg aatcatctag    72943
atattaaaga ggaggggcat atcaaagagg agaaccctag cagagataag aggcaagagt    73003
aaatgtttca tgtatgggta agagtggatt tgtatttacc taagtaaagg tagaccctgg    73063
acaataaggt tggatagatg tggaggtggc aaaccatgga gggtcttgta ggtcaagtgg    73123
atgtttttag acttgaagtg ttaaattatt atctgaaatc attaagagtc ttttttagatc    73183 cttgagcttc ttgagaagac catggatatt atgcagttat tatataatgt tttaaaatag    73243
taagtatttt agtttaactg tcttatgtaa ttccatataa atggatgcat gttctttaaa    73303
aatgttaatg tatttcagta aatcaaaata tacttttga ctcatcattt aaaggaggcc    73363
ttcagtgaat gctctgtaga ggattatttt ataatactaa ttttgatatc ctaatttatt    73423
tgttataaag tttagaaggt ttgaagaatt taaaatatag tgttaataaa cacactgaac    73483 ttttctttt ttatcttgta tttttatata gtacaacaga aaaagatga aatgtgaata    73543 gtaaagagtc tgtgattgtt gttcatag g gcc cac caa gct ctt cct cga        73593
                                Ala His Gln Ala Leu Pro Arg
                                2005                 2010 gat tct gtt gta gaa gat tta cat tta caa aat aga tac ctc  caa         73638
Asp Ser Val Val Glu Asp Leu His Leu Gln Asn Arg Tyr Leu Gln
            2015                2020                2025 gaa aaa ctt cat gct tta gaa aaa cag ttt tca aag gat aca tat           73683
Glu Lys Leu His Ala Leu Glu Lys Gln Phe Ser Lys Asp Thr Tyr
            2030                2035                2040 tct aag cct tca gtaagtgtat atctttatt attttttct tttttccatg             73735
Ser Lys Pro Ser
```

```
                                                             2045
ttaaaatgca tgaaagtgaa atcaacttct ttcttaatct ggccaaaagc attacatctt    73795
tctcattaat agtaatacag taaattcaac ttttattttt aacaggtagt gatgtgtaat    73855
aatttattta atcctttta acataataac agtaaactta agattcttaa gcttttcata    73915
aagctcataa atgatttcta gaaattttaa atatgtagtt atcattatgt attttgctgt    73975
agcagcagta tacagttaaa taaaatagga aaacatgttc caagactgtt ttcattcaaa    74035
tatttatgct atattttag cttataaaaa ctcattaatc attaatgtaa aattatttgt    74095 tggattttt aaatatttag tgtattattt ttgtttcttt tttctttcca tgtttcttca    74155
ttcttccacc ttaagcagaa tcaggtgtgt gacacaacta tgttttctat ccttgttacc    74215
attattaata aatacaaggg catgatattt ttcacaaaag aaacactttg ttcagaacca    74275
aaaaagatca tggcaacagt cagaattaaa aatggtaaaa gactaggtgc caagatgac    74335 ttacataatt gggtacctag aaatattcta tggtattaca gtaatgatga aaatacaaa    74395 ttagaacaca ttttagatcc tattgagtta aataaatcag agtcaagacc aaacaataaa    74455
taaagtcaat ttacgtcaac aaatggtaag ttggcagatt ttaactccct ttttgaaaat    74515
gaaccatgat cctaaggttg gtaaaattaa tcaagaatgt tgtcaaaatg ataaagataa    74575
aaatgaggaa gagaataaga taggcaagag tgagaaagga aagagacaca tagctgaaaa    74635
tgtgagtcac aacaactaca tagatccgta gaatctgcta tggaggactg tgattatgtg    74695
acagttgctg atgccgtggc ttagtgagct gagggtgatg cacaggcagg cgatgtaact    74755
gatgcgtcag tccagccaag aaaggacgcg tccctggttt ggctacgtgg ccgtcccttta   74815 tttctttgtt aactgaattt tcttatagta agtagcttac gtacatatat agtgcaaatg    74875
ggaaagtgtg taagatttag aaaaagcatt aactattagt aaactttatc ttaagctcta    74935
acttttgatt agttcctaca aaaattagtg aatatgcatt ttctaattta gtgctttttt    74995
tttttttaca attggtgttc acttaatgtt atattagata aatgaatagc aaaaataagg    75055
tactttagag ttgattgttt tgccttacaa acttctaatc catccagctg tatttagaag    75115
taagatctca ctacagcgaa ttatatcagt aaaattttgt tacagtgttg tgcagtgtcc    75175
taagatgtat actaagttcc ttcagtggct tttttgcca tgttttataa cagataattt     75235
tgttataatg agaaaaggaa acttggatgt gttgctgtct atattgtgtt aggctcaggc    75295
aggatgctgt ggcttactca tttaatcact ttgggaggca ggggcaggaa gattgcttga    75355
ggccaagagt ttgagatcag cttgggcagc atagccagac cctgtctcta caaaaaattt    75415
agacagatgt ggtggaacac atttgtagtc ctagctatta gggaggctgt ggtgggagga    75475
tcatttgagc ccaggagttt gatgttacat tgccctattg cactccagac tgggcaacag    75535
agtgagacct gtctctaaaa taataataat gataatgata aatggtgtta ggctctgtgc    75595
ctaagtatat ttttcacata ggctgggtaa agtggctcat gcctgcaatc ccagcacttt    75655
gggaggccaa ggcagcagga gcatttgagg ccaggagtca aagaccagcc ttgagagacc    75715
ccatctctac cagaaaaaaa aaaaaaaaga aacaattagc tgggtgtgat tgtgcacacc    75775
tgtagtccta gctactcggg aggcagaggt gggcagatca cttgagccca ggagtttgag    75835
gttatagtga gctaagattg tgccactgca ctccagactg gcaacagag caagactgtc    75895 tcaaacaaaa acaaacaaac aaaaagcact ttgcagaata tcagtctaac tctacagttt    75955
atggactttt tatgtacgta ctacttttgg ctagcttaca ttgagataca gaataaaagt    76015
ttgttcatag catttatcgt ttttttcttt atactgtcca cctgagatat tccagtcacc    76075
```

```
taagtcatgg aaacatcaac taaaattaaa tatctatgtt aagagaaaat ggctgaaagt    76135
gatttaattc ataacacttt ttttcacatg ctaataaata agagtttgag acttccacta    76195
ggcattatct ctaactccta tccactaaga atttgatttt aagtagttga tggcttttaa    76255
ccggattatt cttctgtaag agtttggaag tctcgtgaag ttcgttatac aagaattctg    76315
tttacaagag agcattacat tagaatttgt ttttcagaaa tttggactat ctcaacgaat    76375
acctttagtt ttattatttc aaaatgcaag ggaaaaaatg agccataatc actaatagta    76435
actgcatcat attttagtga gaaatgtgtt aaaaatatcc tcatgtgaga tcttccttag    76495
atagaattac cctctactct aatatttaat atattttata tctaccaatc agtgatatta    76555
ataggtgttt atcatttgct gaatcaaata ggtacaacag aagacaggaa gtttgggaga    76615
tagaagagct cagggacagg aaatcacaga tgtccatatc tgaaataacc ttaaaagtta    76675
tcctgtctaa tgccttcact tataaactgt agtggtagaa tttgcctagt attaacctaa    76735
tagtggtaga tttgaatgta tacttgggct ttcttattaa gtggaaatgt attcctgtga    76795
tttacatata tcaacaaaaa tgtttgtctt ctttttttg ctacgacata tgtgcatgtg     76855
cacacacatc tcctcaaaca aaaatcagat ggacacatgc agtcattgga tctaaaagat    76915
gttataaagt tgtgtataat aggtatttta taataatata ttttaagacc cataatgtcg    76975
gtggagtaac tgactttaca gcccatcaag ccaatagaga gagaaaggag aaaaaaatga    77035
aagttgtgct gaataattaa aaaaaattat ttcctatgat gcttataaca gtcctatgag    77095
gtaggtggta ttctaatta tagaaaaaat gcatagaaaa atataattaa gcacagttaa     77155
aaaaaataaa gtttagaatg agaagtaaca acataaataa tgacccaatg tagattcagg    77215
tcaaaagaaa tgaaaatata atattaatgg ttttcaaaga gggaaccatt actttagctc    77275
aaagaatgaa ggagggcttt ccgaaggagt aaagaattat ggcagttctt ttgtagccta    77335
gtgtattcat ttgctaaggt ggctgtaaca gactactaca gatttggtgg cttaaacaat    77395
agaaatttat ggtcttagtt ctggagacct agaagtccaa aatcaagaca tcagcagggt    77455
tgatttcctc tgcacaatca gagggaaaga tctttcccaa tcctctctcc ttggcttata    77515
aatgtccatg ttttccctgt ttcttttat catcttcctt ctgtacatgt ctctgtgtct     77575
aaatccccaa attttctctt ttcataagga taccagtcac agtcgaatag ggtttaccct    77635
gaaatctcat tttaacttga atacctctgt aaagacccag tctccaaata aagtcacatt    77695
ctgaggtact ggaaattatg actttaatat ataaatgtgg agggtaaggg gaacacagtt    77755
caacccataa cggttagata acaatcgtgc tttattttgg actagtaaaa ccaccataga    77815
tcagtttaac cattatgaaa ttatacatga aggcattata tgtatggaca ttattaagtc    77875
atacttgctt tgcttccatt gtaattaaaa caaaccatac tacctttgtt ctgcaagttt    77935
tgtattctaa cttatttatt tttggctttc accagaacac tccgattttc tcatattcct    77995
ttgaggaaaa aaagtaccct tttgacagta ttttcttatc cagtatgtct tttatggctt    78055
ttatttatta aactttaaaa atattcctaa tttcatttcc ctgaag tca gga          78110
                                                      Ile Ser Gly ata gag tca gat gat cat tgt cag aga gaa cag gag ctt cag aag          78155
Ile Glu Ser Asp Asp His Cys Gln Arg Glu Gln Glu Leu Gln Lys
    2050                2055                2060 gaa aac ttg aag ttg tca tct gaa aat att gaa ctg aaa ttt cag          78200
Glu Asn Leu Lys Leu Ser Ser Glu Asn Ile Glu Leu Lys Phe Gln
    2065                2070                2075 ctt gaa caa gca aat aaa gat ttg cca aga tta aag gtgaatttaa           78246
```

```
Leu Glu  Gln Ala Asn Lys Asp  Leu Pro Arg Leu Lys
    2080         2085              2090 tgttttttat taggaaatct aatgcctaaa actccttcct tagttgttat gtttactttt    78306
attagcttat taagaagtca aaaatgcata ttcctaatat atcatggtga tggtatactt    78366
tatacatttg ctctttagca tttatttgtt gaaggcctac tttatattaa acactcctcc    78426
agatgctggg aaacagcagt caaaaaattc cttatactca taggacttac gttctagtgg    78486
agaagactga caataaacaa gtcactaaat agtatgtcat ctgatgttag tgctaaggag    78546
agaaataaag catgattggt gtaaagagta tggggagaga aagggggtgt aactgaaaat    78606
agagtagtaa gggaggtctt ccttaataag atgatatatg aacagagagc taaggagggg    78666
taaaggaagt gagtcataca gatactagaa aaataattac agacaacaga aatagcaagt    78726
tcagatgtcc taaggtggga ggatgcgtgg tatatttcat taaaaattat cacactgtaa    78786
aatataagaa taatttgttt cttttagaaa ttttacttta ttctgatatt aataatgatt    78846
ttttaatctt tggttttcca agtcttaccc tatttatggg aatctttttt ttcttttggc    78906
tagctaattg cttcagtttt gttttctaat ctagaatgtt agcaatctgt taattccact    78966
ggtaatgata tagttaagct atgtcttgct tctcacactt tatttattta tttactcagg    79026
gcactaatct gccattttt cgcactttt ttcctttttt ttttttttgg tactgcttct    79086
tattctggtt tttacattga tagaaccaat gttagacgtt catttgcctt ttgctgtgta    79146
tatttgggta aggatctata tgtgcaatat atgggacagt taaaatcaga attctaaatt    79206
tgtattattg catcaggcaa taatgtggga aataccttga catttcatat acacaatatt    79266
cttgtattaa tttaacgtct tagttcaaaa tcttccttgt taatatagag accctattat    79326
ttggtttggc aatacagttg aagagattga tggttcttat gaattgtttg ccttttcttt    79386
tcaatggctg tagctatgtt aaattattac atgtttgctt gttatctttc ag aat caa    79444
                                                           Asn Gln gtc aga gat ttg aag gaa atg tgt  gaa ttt ctt aag aaa  gaa aaa       79489
Val Arg Asp Leu Lys Glu Met Cys  Glu Phe Leu Lys Lys  Glu Lys
    2095             2100                         2105 gca gaa gtt cag cgg aaa ctt ggc  cat gtt aga ggg gtatgtgaga         79535
Ala Glu Val Gln Arg Lys Leu Gly  His Val Arg Gly
    2110             2115 atttaccata catttgtttt ggtttcagca gtgataagcc agaaatgaaa agtttagata   79595
tgttgtaaaa gtactgatat gcctctacaa gtgccctgta gtttcagtgt ttattctgca   79655 tctgtaaatat aaaacagtaa gcatttctat gtgtctcaaa gtattttatc atctgttata  79715
ccttacatac tttcatctct ctttttattg aatatgcctc catccttga aaacatttaa    79775 cttccaggaa tccttttgtt tatggaggta actgctaact ggtccttggt ccaatgctgc   79835
cattttgtaa ccatttgtta tgatatcttc ccagcttggt ataatgtttt ataattacat   79895
tgttcctccc cctctttttt tgtgttcttg taattttctc cctatgttat tttgtattca   79955
ttttatataa tgaataaatg ttgcttatga ggtcaaggcc aaagacttaa gctcctgttg   80015
atttcatgtt gctgagtgtc ataaatggaa gcaatcataa tgcagagtca ttctggtagt   80075
aatattaaat atatgatgga ttcagtgaaa atattatgtg ttattagaaa atattcaga    80135 acaggccggg ggcagtggct cacacctgta atcccagcaa tttgggaggc cgaggcgggc   80195
agatcactgg aagtcaggag ttcaagacca gcctggccga catggtgaaa ccccatctct   80255
actaaaaata tgaaaattag ctgggcatgg tggctcatgc ctgtaatcct agctactcag   80315
gaggttgagg caggagaatt gcttgaacct ggcaggcgga ggttacagtg agccatggtc   80375
```

```
acacaactgt actccagcct gggcgacaga gcgagactcc atctttttaaa acaaaaaaaa   80435 aaaaggaaaa atattcagaa cagtatcttg ctggcagcaa catttgtttc atcaatgaaa   80495
atatgtgtta atttgacctt ttctatctaa gttaattatg aaagtgcata ctaaaatgat   80555
gtaaaagttt atatttcagg attattctta ttcatggatg attaactaaa atgcaaaaag   80615
aaattaagca tactgtttgg ctaaactgtt aaaaattatt tttatttttaa atgataagca   80675 gttaaactta ttaagtgatg actcatctct gctgatatat ttatgcaagg ttttttattt   80735
cagataactc ttctatttat attaaacaga aactgtattt ctaagcaata gcatttctta   80795
gagaaaattg cctctattat gttgcaatta aaatttaatt actcatgagc tctttaaaga   80855
cacaatttct cttgtgtggt tttatttcat ataagaaaaa actctgatat actggagaga   80915
acattagcta aatagactat ttagacttaa tcattttgat cagacatcaa ggctagacta   80975
tttaagctgt tacttattag ctgcatgatt ttaggaatgt caaatttcct aagtcttggt   81035
tttcttgtat ttaaaatgga aattataatt cctatctcat agaattgttt taaggatgaa   81095
ttgaattaat acagttttga cttcaaatat taggaattat tgagtataat aagcctgttg   81155
tattgttggt acttcgtatt atacttacta aaatatttga ttaaagattt aacatattct   81215 ttcgtag tct   ggt aga agt gga aag   aca atc cca gaa ctg   gaa aaa      81261
        Ser   Gly Arg Ser Gly Lys   Thr Ile Pro Glu Leu   Glu Lys
        2120                  2125                  2130 acc att ggt   tta atg aaa aaa gta   gtt gaa aaa gtc cag   aga gaa      81306
Thr Ile Gly   Leu Met Lys Lys Val   Val Glu Lys Val Gln   Arg Glu
        2135                  2140                  2145 aat gaa cag   ttg aaa aaa gca tca   gga ata ttg act agt   gaa aaa      81351
Asn Glu Gln   Leu Lys Lys Ala Ser   Gly Ile Leu Thr Ser   Glu Lys
        2150                  2155                  2160 atg gct aat   att gag cag gaa aat   gaa aaa ttg aag gtaatttttt         81397
Met Ala Asn   Ile Glu Gln Glu Asn   Glu Lys Leu Lys
        2165                  2170 ttaatgtgat cattttaggg ggaatatttt acgttttgtt actatttagg aaaatttcaa   81457
atatgctcat tactatataa aatggcttta atgaatacaa tacatatttt ataaatatag   81517
aaaaaaactt atgagaggca aggctaaggg ttatagagta ggtctacctg atctttcttg   81577
ttatttcaag accaatactt ttcacttttc tctctgacag catagattaa ttacctgtgt   81637
ctctcttttt ttttctttt gagatggagt actgctttgt cacccaggct ggaatgcagt    81697
ggtgcaatct tgactcactg caagctctgc ctcccgggtt catgccattc tcctgcctca   81757
gcctccccca gtagctggga ctacaggtgc ccaccaccac gctggctaa cttttcgtat    81817 ttttagtaga gatggggttt caccatgtta accaggactg tctcgatctc ctgacctcgt   81877
gatccgccca ctgcggcctc tgtgtctctt tgtgaaaata cagatgccca agctcccatc   81937
cctgaaattg atttaattat tttagggtgg gtcctgacac agatatgtat gttgttgtta   81997
ttttaagtca tcaatttatt ctaatatgta gccaacgttg gaacttcgt tctcactaat    82057 attcaaatga agactttaat tctaatcata tcaaatatgg tttctaaaac tactttgaag   82117
atttatgagt ttataagatt atcttttatt tccttgtttt gataatgtat acttttttatt   82177 ttgtttgttt ttttactag gct   gaa tta gaa aaa ctt   aaa gct cat ctt       82226
                       Ala   Glu Leu Glu Lys Leu   Lys Ala His Leu
                             2175                  2180 ggg cat cag ttg agc atg   cac tat gaa tcc aag   acc aaa ggc aca        82271
Gly His Gln Leu Ser Met   His Tyr Glu Ser Lys   Thr Lys Gly Thr
2185                  2190                  2195
```

| | | |
|---|---|---|
| gaa aaa att att gct gaa aat gaa agg ctt cgt aaa gaa ctt aaa<br>Glu Lys Ile Ile Ala Glu Asn Glu Arg Leu Arg Lys Glu Leu Lys<br>2200                         2205                      2210 | | 82316 |
| aaa gtatgactt tatgactgat tataactttt gattttatt ttacttaata<br>Lys<br>2215 | | 82369 |
| cctcttggaa aaactggaag tagatccttg atgagagtgt ctgtaaaggt agatattaag | | 82429 |
| agattgagga attgtgtttc tatgcctgct gtcatcacat tccaccatga aaaacattga | | 82489 |
| taataaaagt taatacattt aggctgggca cggtggctca cgcctgtaat cccagcactt | | 82549 |
| tgggaggcca aggcgggtgg atcacgaggt caggagatcg agaccatcct ggctaacacg | | 82609 |
| gtgaaacccc gtctctacta aaaatacaaa aaattagccg ggcgtggtgg cgggcgcctg | | 82669 |
| tagtcccagc tactcgggaa gctgaggcag gagaatcgct tgaacccggg aggcagaggt | | 82729 |
| tgcagtgagc cgagatcgca ccactacact ccagcctggg caacagagcg agactccatc | | 82789 |
| tcaaacaaac aaaaaaaaga aatgatctac gttgcttaca catacctatt gcttatagct | | 82849 |
| aggtctcgta agcattagga agtcaaaaca aagaatcttt tacatgtgta aaggtataaa | | 82909 |
| ctatcccatt tttctaaaaa tatagaggaa caaagtgtca aatttaaagt aatcactagt | | 82969 |
| aactaaatat attcctctga cctcatttc gtgatctgtt gttctaatta ttattggcca | | 83029 |
| tattgctgct ttaaggaga gatgttgaat tgttgaaat tttaatcagc atttagagcc | | 83089 |
| ccaggttatt tttgttttcc aatttgtaat gataattttg aatacactga atctatgaga | | 83149 |
| acagtattat gttttctcat aaaatactaa ttagcattta atgatag gaa act gat<br>                                                                                            Glu Thr Asp | | 83205 |
| gct gca gag aaa tta cgg ata gca aag aat aat tta gag ata tta<br>Ala Ala Glu Lys Leu Arg Ile Ala Lys Asn Asn Leu Glu Ile Leu<br>    2220                         2225                           2230 | | 83250 |
| aat gag aag atg aca gtt caa cta gaa gag act ggt aag aga ttg<br>Asn Glu Lys Met Thr Val Gln Leu Glu Glu Thr Gly Lys Arg Leu<br>    2235                         2240                           2245 | | 83295 |
| cag ttt gca gaa agc aga ggt cca cag ctt gaa ggt gct gac agt<br>Gln Phe Ala Glu Ser Arg Gly Pro Gln Leu Glu Gly Ala Asp Ser<br>    2250                         2255                           2260 | | 83340 |
| aag agc tgg aaa tcc att gtg gtt aca ag gtaggaacag agttttaaac<br>Lys Ser Trp Lys Ser Ile Val Val Thr Arg<br>    2265                         2270 | | 83389 |
| ttgtacaaag tttaatcatt tcaaattttg gcattgtttt aaaagacaac actattctgg | | 83449 |
| ataacctggt ttcttcctga tgaacagttt gttggttgt tgttttaaca taatactttt | | 83509 |
| tttctgttgt agtattgttg gagactttt cttccttgaa atgttaact tgtttaacct | | 83569 |
| tgtttgggtg gcagggcatg aacagtgta gagctgggc tgggcgaagg agttggagct | | 83629 |
| gtgtgtgcgt catgaagctg tcatcagcta tgagcctggg ctgaggctgc tcagcttctc | | 83689 |
| ctgggtgcta ttttctcca actgcagctt cagcttcttg attgtataat tgcttcctc | | 83749 |
| aagtatgagc caggaataat tgagctgtct tgtcacaatg tgtggcatac tggatctagg | | 83809 |
| ctgtgctgca atgctttag agttatatcc tgggcaactt tctcttcaga tagccccaag | | 83869 |
| agatgaattc agcaccagct ttgatgtttt actagcttct gctttctggt acttgatttt | | 83929 |
| ctcccacccc gaacacatgg gattccaacc tgtgaaacta attttgtgg ctatgaaaga | | 83989 |
| ggtagtggta gtttatgagt aaacattcag tctgttgcca ctatcatcat gtgtggttca | | 84049 |
| tcatgactgt gatgagtagg taaaggctc tttgtgtcat tctcattcc aattttaagc | | 84109 |
| agctgcttca aggagtctgg aagtcattga ccagtgggat cctgcctgtg tcttttccca | | 84169 |

```
ttaaagccat cctgtatgaa gtggtatcct ttaccatcta gcacatctgc cgcccccatt    84229
tcaaaaggca tactcatctt tatctcaaca ttctcataca gttccttatg tccatgcacc    84289
tccaatgtcc cctttgatgt ctttgaggtt ttcatcttcc atgtctgcta tttggaatgg    84349
tcttgatggg aggcaagata gtgatcacta caactaggat gggagtctta gtaccgtgag    84409
gctacagcaa gtcccacaga gggcctgctg cactgtactt gcctctgtca accaagtcta    84469
aggagaaaga ttaagcaggc atattaaagg acagcccaga tggacatgaa gtcctggagg    84529
aggccttggt tcctgtccta atactaaacc tagagtaccc agaatccaca cttctccact    84589
ctagctctca cttttcccat ctacacactg ggaaaaatta ttctgtcaga aagccagtgt    84649
caaggtgaga acaaataaca aatgtgatga tatggagtgg gagaagggt  ctcttctact    84709 gtcttattgg accctagcag tggctctgag ccagcagtcc tgtcagttga tttcttggtc    84769
gttcctttgt tttcttctat aatcacatgt ggactcagaa tgaattttga gttactctga    84829
aatctattta ttcaacagat atttacttag tacctcctat tgccagactc tgctttatgt    84889
tggatattat tttttaaaag cccaccttgc ctagatttcc tcaaaggacc aggtggcttc    84949
cctggttttg aaagacccta attcttacta tgatcttaag taaattatat cctttctgtg    85009
ggctcaagtt ctttctaaga gggctctttg gggctacaaa agaaattgtt agtgcaaaaa    85069
gagtttataa ggtttataaa tggttagtag aggtgatgat gatatttaac cataattgaa    85129
gatgactttg catttagat  catatacgtg ttttcgtct gagaacgata caggtcactg    85189
agcataccat aagccttcag taaatcattt gcagaagaca ttgcagaaga cataagtcta    85249
agtagaaatc tcttgacaga gagaaggctc gttttgatcc ttgacctcaa atttaggttc    85309
cctaaatcca ttaaaaaga  gaaagaaaaa gaaaaaaagt tactaaagtt taaatctggg    85369
aggattatat acccttctca ataaagcagt ttagagagat ctcttttggg acccatgaca    85429
caggtcttgc tcatgctgac atctttatag ttgctttatt atttattcaa caaacttagt    85489
aacacgtatt ctatgtcagg ccttttcctg actactggga caaaccaggg tgatgtgggg    85549
gctgttttag atagggtgat cagaggaggc ctctctgttt gggtggcttt tgaatagaaa    85609
attagatgaa gtgaaggagt aagcttctga tatttcactg tttacttgtg gtagatctgt    85669
gataatctct gtcaggttaa aaacattccc ttctaatcta agtttctaag atctatcaaa    85729
agctgtttga atatatttag acaatcataa ttttcctttc ttgtattatc ctagcagatt    85789
ttgttgccaa agctatactg gccattttaa cttagaatgc agtctttcta ttcatttctc    85849
tggaaaagtt tggatattgt aagcattatt tttcttaagg tatgatgaac ctgcagaact    85909
gtttggttca attatgaatt ttttttttct ggagtctgta tttttttgaa ctattaatca    85969
tttctttaat gattataaat ctattcagat ttttacaagc tttatccctc tcccatcata    86029
cactattttt cttacccatg cttttgcaca attttttcct ctcccttagt gttttcctac    86089
ctagatacct cctatgtgtg tctgtgtatg tgagaaaagc ttttatttg  ccatcttat    86149 atttctaaga atatctagta atacagaatt ttatattctg aagaatttta ctttgcattt    86209 tcttatttg  tgattgaaaa aaggtattaa ttttaaaatg gtcaaatcag gctccatcct    86269
tggaaaatac ccaaatcctt tattttgatt gggccatctg ttaattaggg ataccttatc    86329
tcttgccacc acttttttaat gctaaataaa tatgtagcta aaactttgac tagaagaaac    86389 agtaaaaataa gatattcttg cttattttta gtacagttat ttgaactgac ttttaaatca    86449
gtgacataaa ttatttgcca tgtctatact ttttttcctt atactttag a atg tat    86506
                                                         Met Tyr
                                                         2275
```

```
gaa acc aag tta aaa gaa ttg gaa act gat att gcc aaa aaa aat        86551
Glu Thr Lys Leu Lys Glu Leu Glu Thr Asp Ile Ala Lys Lys Asn
            2280                2285                2290 caa agc att act gac ctt aaa cag ctt gta aaa gaa gca aca gag        86596
Gln Ser Ile Thr Asp Leu Lys Gln Leu Val Lys Glu Ala Thr Glu
            2295                2300                2305 aga gaa caa aaa gtt aac aaa tac aat gaa gac ctt gaa caa cag        86641
Arg Glu Gln Lys Val Asn Lys Tyr Asn Glu Asp Leu Glu Gln Gln
            2310                2315                2320 gtaagtaacg taattttctt ttacatgata aaataatgca taatatcgca agatgttcct   86701
tgcattgtct tatatagata aaaatggact ctattaagaa gacccatcta actgaagggc   86761
acccccattca cccatttgct taagccagaa actttggatc atcaacgact tcattctttt   86821
cattctccac attttctatc attaaatcat gtcagctcta ttttcaaact atatcctaaa   86881
tatgaccact tcttggtatc ttgagacatc actaccagtc ttgtccaagc tattgtttta   86941
tacctgaata actgcaataa tttccaagct ggtatctcag cttccactct tggattattt   87001
cacccctattt ctatttctgg gctgtctcca cacagttgcc aggtaaccct tttaaaacat   87061
aaagcacatc acaaagcaca aagtcctatc ctcagaatct tccagtggtt ctccatcacc   87121
ctaaaataaa acttaaaagt tcttttcata tcccaaaaca acatatgagg tctggcaccc   87181
agttttcttc ccaatctcat cttctactac ttttcccttc atttcattca caatgtttta   87241
accacagtaa ccttctttca gtactttaaa caatccaaac tcgtttaagc gtcaagtcct   87301
tatacttgtt tcctttgttt agaatactgt tcacccaaat attctcatag cttgctccca   87361
gacttcatgt ctctgctgaa atagaggctc cttagagaga ccttccctaa ccctaaccct   87421
aaccctatac tacttgccat cactctttat cctcttaccc tggattattt tttcttgata   87481
gctcttccta ccatctggca ctatattaca tcatatcata ttaaacacac attctttgtg   87541
cttccccact aaacaaggac catgcaagat ggaacattgc cattttgttc actgctgtta   87601
gcctctgtgc ctaggacaat gccagttatg cagtagttac tcaatacttg ttgaatgaat   87661
ggtgaataga acatagaaat ttgcctatgc gtgcttttga aaaccatatt ttaatattac   87721
gctttgttaa aaatgtgtat cttttataaat cctcatattt ccatggcaaa ccttatcttc   87781
taacttttca ttgtcctcaa ag att aag att ctt aaa cat gtt cct gaa       87830
                        Ile Lys Ile Leu Lys His Val Pro Glu
                                            2325 ggt gct gag aca gag caa ggc ctt aaa cgg gag ctt caa gtt ctt        87875
Gly Ala Glu Thr Glu Gln Gly Leu Lys Arg Glu Leu Gln Val Leu
2330                2335                2340 ag   gtacatcatg tattcatatg actactttgt ttttttcttt aaaaaaaaaa        87927
Arg
2345 ttattagttt ttatatactc cgaattgcta caactagaga caagcatttt tcgactttac   87987
tgcctaacag gcttattagg tccttatttc ttccctctaa tgctaatcac tcttttttcat   88047
aatacacact agaaaaaaag gataaaccca actctaagtt tccagtttgt aatttagttt   88107
aaacttttct aagagcatag aatgagttaa accttagctt cccagaggaa aatactaatg   88167
aaagagaaca agtaattttt ttactttcag gggtctctgt agcctgcttt cattaagctc   88227
ctcttataac gaaaccacac ttgcaaatgc catcaggtca gatattaaga aaaacgtgaa   88287
ggcttttgta ttccaggctt tttgtttgag aatggtgaca ttgtagcatt gagagtaaat   88347
gtttacttcg ataaaggcta gcttgttctg attactgtac atcactagtt cataagaaat   88407
```

```
gcccatatat tttatgaagc aatatctgct ttatttttt aacacattat cattgtgttc    88467
```

```
tag a tta gct aat cat cag  ctg gat aaa gag aaa  gca gaa tta atc    88513
    Leu Ala Asn His Gln  Leu Asp Lys Glu Lys  Ala Glu Leu Ile
                     2350              2355
```

```
cat cag ata gaa gct aac  aag gac caa agt gga  gct gaa agc acc      88558
His Gln Ile Glu Ala Asn  Lys Asp Gln Ser Gly  Ala Glu Ser Thr
2360             2365                 2370
```

```
ata cct g gtaatgtatt ttaaaaaaca tgttagctac ccccaagttt ttgaatttgg    88615
Ile Pro
2375
```

```
gtttgccttt tttttttttt tttggctcag atttctgatc attgtctccc tgtaaaatcg   88675
aattcctgat aagctttggg tcttttgtct ctctgtgcta ttaatataaa aatattccca   88735
tttttctctt tgtgttgttt atactataga gtagcaagta cccaagtgtt cttctctttg   88795
ttctccatct gggtgttaca gatttaatca caatacagtg ctaagcaatg aatactaaat   88855
ctgttgcttc cagtttctaa gtataggctc tttcaagtcc tctgaacatt tttaaaaact   88915
gcaaataagt aaatactgcc tatatttttt tccgtttaca agtaaaaag aaaatctttc    88975
tgctcccttc cattcccatt caaaagtgat tactaatcat tcctcattcc tgcatataca   89035
tacacacata ttttgtatac atatatatca cacatatgca tacatgtgtt tgtatgttca   89095
tatgtacaat gtacatatcc tcattatttg tggattctgt attttctaaa tcacctcctc   89155
actaaagtgt gtatgtaatc ccaaatcaac actcgcagca catttgcaaa catccacaga   89215
gccttggaaa gtttgaataa tccaacctac atgtccccag cagaagtcca acaaggcagt   89275
gctcagtatc ctcatttcag ttttcataga gaaatgagca gaggatggag acagtagagg   89335
gcagcacagc atagtgcaag aagctgtggc tctggggcct ggtggaaggg atttgaatcc   89395
caattctgag gcttgttact gctctagcct taggagagtc atgtaacact tctgaatctt   89455
gttttcttat gtaaataaat agaatttacc aggatgagtt atctttagga tttaagatta   89515
tcatctgtgt gagatatgta ggtgtatgta tatatatgcg tgtatgtata tatatgcgtg   89575
tatgtatata tatgcatgtc tgtacatatt tcccgtagca gcagtggttt gatattcact   89635
aattgggcta actttataga ccaaaactac tatggataga gaatactttg tttgcattta   89695
cgtatatata tttttcttgg c aagtaacata aaattgaact aatactatac acatttctag  89755
catatttgcc tttaacagtt tatcatggac atcttttgag gtctgttcat aaattatctc   89815
atccatttaa taattccata gtgtattatt gcatgtataa gcacatcgaa ccatttatgt   89875
tttgatggat atttagtttg cttccaagtt tctgcttcta taaatatga ttaatctatt    89935
gacctaatta tgccattgtg ataggatgat agagatgcca ttctctccaa aggattatac   89995
caatttatat ctgaactatc tttgactatc tcttgtagct ttttcagtat gctatgtagt   90055
cctattacta atttgtaata aaagccatca tgtgtgagtt gtactagaca ctatgctaat   90115
tgccttacaa gcattctata tttacaacca tatatgatag gtattactgt ctccatttta   90175
tgtgataaac aaattcaaag tggttaagta accattccct aagccagcta ggaaatagag   90235
gcaggattaa aatctaaatg tatgaaactc cacagctcct tggcattcct agtccttaac   90295
ccgctatgct atgctacgtc ttggtaacta aaagtacata ttaaatactc tcaaaatatg   90355
tctcatagca gccagcttgg tatgtacact agacacagta ttaatgctgt tgatgtgagg   90415
aaaattttat aattttcctt ccatccatat actaaccagg cccaacagtg cttagcttct   90475
gagatcagag atcaggtgca tgtgcattaa gggtcatatg gccatagata gttctctaat   90535
cttttccattc ctcagttct taagggaatt tctgaaccct caaaattcct tatttcctaa   90595
```

```
gtagacagat tacctgtcat ttttcaaaga ttaaggctta agatcaaacc agaactgttt    90655
tggaaattct aaatcactgt ctatataaat ggcaagataa cttttaagat atttatacca    90715
agcccagtac agtagcacac cacacctgta atcccagcac tttgggaggc tgaagtgggt    90775
ggatcacatg aggtcaggag ttcgagacca ctctggccaa catggtgaaa ccctgtctct    90835
actaaaaata taaaaattag ccaggcatgg tggcacttgc ctgttatccc agctacaagg    90895
gaggctaagg caggagaatc gctttaacct gggaggcagt ggttgttgca gtgagccaag    90955
attgcaccac tgcactctag cctgggcgac agagtgagac tgtctcaaaa aaaaaaaaaa    91015
aaaaaaagat acttgtccca gccatgaaaa tgtttgctgc cccttacttt cgcaaacttt    91075
tagtatttta ttattttca atggctgtaa aatatgactt attaaatgta gtataatata    91135
aagaaaagag atatctagca aagatagcat taaagcaaaa atcctatttg cctgctgata    91195
aagttagagg tgttaacttg gagggtgaat ccaataaatt agaactttg tgctatattt     91255 ggagactttt gttttcctac caaagtatca gggctatgtc ttacttatct ttgtattaca    91315
cagcctgcat gacacgtttt gcacatagta attgcacagt aaatgtgtaa taacctacat    91375
ggaatagcca gtgttgtgtt ggatagcggg agcatttggc tagcttatgg ttatagtccc    91435
ttacccaaca gtctgctttt cttctgttgt acttttagta cctaacaagt ttccctggct    91495
ttaggatttt ttccatgtaa aatttctatc atgtgaagaa aaataacttt ggcctacact    91555
tctaatacct agcacatacc tctttctgcc tgctatgaaa ttataatact tgatggaggg    91615
aggcagcatt aagtgtttac atcctgaagt atttcagcca taacatccag tgttttccag    91675
gttctaggtt tcataaaatg tatctctgtt ctctagaaca aatccattac cttgaactca    91735
ttcgtagtgg gaaaaagctg agtctaattt gtatgacttt tcaacag at  gct gat       91791
                                                     Asp Ala Asp caa cta aag gaa aaa ata aaa gat cta gag aca cag ctc aaa atg          91836
Gln Leu Lys Glu Lys Ile Lys Asp Leu Glu Thr Gln Leu Lys Met
2380             2385                 2390 tca gat cta gaa aag cag cat ttg aag gtaatattta attatatttt           91883
Ser Asp Leu Glu Lys Gln His Leu Lys
2395                 2400 agtatcgttt tgtgaaaaca gctgttgaaa actattttca ttaccatctt taactacgta   91943
tcctaaaaaa ttcagtaata acatcttata tttgaccttt atattgcaaa gttaattatg   92003
ttcatctgac tattcctaac atattagagt taacaaaaaa ttcagactca acataggatt   92063
aagtagtaaa tttattttt aattgtaaca aatatatgcc attagtatgt tcttaagttt    92123
tgggtcacat tggcaacagt gtctttattt ttttttttgaa attcttttca ggaatcctaa  92183
ggttatagtt ccccttaaaaa aatatttgct gttttacctc ttttaagact gtaaacagga  92243
caaaaaggca tggatatgag aattagctag tgatcactgg ctattctaaa tagtcactaa   92303
ggcttgaatt gtctcttcac cagatgcctg tcagaagtcc caaggtttc cctgatcata    92363 ttaataactt tataaaaaat tgatcattat tcattaaata ttagatatta gtaaggaaaa   92423
tataaatgaa gtctaaacca aaactcttaa ccagactaac ttcaatgtta tgaatcacaa   92483 aatcttttg attgattgct ctattgacaa gctcttatat gctttagag aaagattaag    92543 tcccattata agagatgata aattttagtc aaagactaga acacaactta cagaatacat   92603
aactggactt gacagttaac aacttagtta tttacactgt acaatggaac aaagaaaaat   92663
cttaattctt ctgcctttat tgctgtattt gaccattcag gaatactttg gctttcatat   92723
ttacaattaa atctccttgt tcaaacgtaa aatatgtata tttcctatat gcaacttta    92783
```

```
aagataatgt tccattag gag gaa ata aag aag ctg aaa aaa gaa ctg          92832
                    Glu Glu Ile Lys Lys Leu Lys Lys Glu Leu
                        2405            2410 gaa aat ttt gat cct tca ttt ttt gaa gaa att gaa gat ctt aag          92877
Glu Asn Phe Asp Pro Ser Phe Phe Glu Glu Ile Glu Asp Leu Lys
    2415            2420            2425 tat aat tac aag gaa gaa gtg aag aag aat att ctc tta gaa gag          92922
Tyr Asn Tyr Lys Glu Glu Val Lys Lys Asn Ile Leu Leu Glu Glu
    2430            2435            2440 aag gta aaa aaa ctt tca gaa caa ttg gga gtt gaa tta act agc          92967
Lys Val Lys Lys Leu Ser Glu Gln Leu Gly Val Glu Leu Thr Ser
    2445            2450            2455 cct gtt gct gct tct gaa gag ttt gaa gat gaa gaa gaa agt cct          93012
Pro Val Ala Ala Ser Glu Glu Phe Glu Asp Glu Glu Glu Ser Pro
    2460            2465            2470 gtt aat ttc ccc att tac taa aggtcaccta taaactttgt ttcatttaac         93063
Val Asn Phe Pro Ile Tyr
    2475 tatttattaa ctttataagt taaatatact tggaaataag cagttctccg aactgtagta    93123 tttccttctc actaccttgt acctttatac ttagattgga attcttaata aataaaatta    93183 tatgaaattt tcaacttatt                                                93203

<210> SEQ ID NO 2
<211> LENGTH: 7972
<212> TYPE: DNA
<213> ORGANISM: Homo sapiens
<220> FEATURE:
<221> NAME/KEY: CDS
<222> LOCATION: (345)..(7781)

<400> SEQUENCE: 2
atttgaagtc ctcgttccac gccttctcat catcctgaac accgagctct gggactccgg     60
cggagaatct aaacgtaaag catcacccac ggtcgtgaac tgtaggctct cctggcatcc    120
gggatcttat tctggccttg gcggagttgg ggatggtgtc gcctagcagc cgctgccgct    180
ttggcttgct cgggaccatt tggctggacc cagagtccgc gtggaaccgc gatagggatc    240
tgtcagggcc cgcggccggg tccagcttgg tggttgcggt agtgagaggc ctccgctggt    300
tgccaggctt ggtctagagg tggagcacag tgaaagaatt caag atg cca cct aat     356
                                                Met Pro Pro Asn
                                                1 ata aac tgg aaa gaa ata atg aaa gtt gac cca gat gac ctg ccc cgt      404
Ile Asn Trp Lys Glu Ile Met Lys Val Asp Pro Asp Asp Leu Pro Arg
5               10              15              20 caa gaa gaa ctg gca gat aat tta ttg att tcc tta tcc aag gtg gaa      452
Gln Glu Glu Leu Ala Asp Asn Leu Leu Ile Ser Leu Ser Lys Val Glu
            25              30              35 gta aat gag cta aaa agt gaa aag caa gaa aat gtg ata cac ctt ttc      500
Val Asn Glu Leu Lys Ser Glu Lys Gln Glu Asn Val Ile His Leu Phe
        40              45              50 aga att act cag tca cta atg aag atg aaa gct caa gaa gtg gag ctg      548
Arg Ile Thr Gln Ser Leu Met Lys Met Lys Ala Gln Glu Val Glu Leu
    55              60              65 gct ttg gaa gaa gta gaa aaa gct gga gaa gaa caa gca aaa ttt gaa      596
Ala Leu Glu Glu Val Glu Lys Ala Gly Glu Glu Gln Ala Lys Phe Glu
70              75              80 aat caa tta aaa act aaa gta atg aaa ctg gaa aat gaa ctg gag atg      644
Asn Gln Leu Lys Thr Lys Val Met Lys Leu Glu Asn Glu Leu Glu Met
85              90              95              100
```

```
gct cag cag tct gca ggt gga cga gat act cgg ttt tta cgt aat gaa      692
Ala Gln Gln Ser Ala Gly Gly Arg Asp Thr Arg Phe Leu Arg Asn Glu
            105                 110                 115 att tgc caa ctt gaa aaa caa tta gaa caa aaa gat aga gaa ttg gag      740
Ile Cys Gln Leu Glu Lys Gln Leu Glu Gln Lys Asp Arg Glu Leu Glu
        120                 125                 130 gac atg gaa aag gag ttg gag aaa gag aag aaa gtt aat gag caa ttg      788
Asp Met Glu Lys Glu Leu Glu Lys Glu Lys Lys Val Asn Glu Gln Leu
        135                 140                 145 gct ctt cga aat gag gag gca gaa aat gaa aac agc aaa tta aga aga      836
Ala Leu Arg Asn Glu Glu Ala Glu Asn Glu Asn Ser Lys Leu Arg Arg
150                 155                 160 gag aac aaa cgt cta aag aaa aag aat gaa caa ctt tgt cag gat att      884
Glu Asn Lys Arg Leu Lys Lys Lys Asn Glu Gln Leu Cys Gln Asp Ile
165                 170                 175                 180 att gac tac cag aaa caa ata gat tca cag aaa gaa aca ctt tta tca      932
Ile Asp Tyr Gln Lys Gln Ile Asp Ser Gln Lys Glu Thr Leu Leu Ser
                185                 190                 195 aga aga ggg gaa gac agt gac tac cga tca cag ttg tct aaa aaa aac      980
Arg Arg Gly Glu Asp Ser Asp Tyr Arg Ser Gln Leu Ser Lys Lys Asn
            200                 205                 210 tat gag ctt atc caa tat ctt gat gaa att cag act tta aca gaa gct     1028
Tyr Glu Leu Ile Gln Tyr Leu Asp Glu Ile Gln Thr Leu Thr Glu Ala
        215                 220                 225 aat gag aaa att gaa gtt cag aat caa gaa atg aga aaa aat tta gaa     1076
Asn Glu Lys Ile Glu Val Gln Asn Gln Glu Met Arg Lys Asn Leu Glu
        230                 235                 240 gag tct gta cag gaa atg gag aag atg act gat gaa tat aat aga atg     1124
Glu Ser Val Gln Glu Met Glu Lys Met Thr Asp Glu Tyr Asn Arg Met
245                 250                 255                 260 aaa gct att gtg cat cag aca gat aat gta ata gat cag tta aaa aaa     1172
Lys Ala Ile Val His Gln Thr Asp Asn Val Ile Asp Gln Leu Lys Lys
                265                 270                 275 gaa aac gat cat tat caa ctt caa gtg cag gag ctt aca gat ctt ctg     1220
Glu Asn Asp His Tyr Gln Leu Gln Val Gln Glu Leu Thr Asp Leu Leu
            280                 285                 290 aaa tca aaa aat gaa gaa gat gat cca att atg gta gct gtc aat gca     1268
Lys Ser Lys Asn Glu Glu Asp Asp Pro Ile Met Val Ala Val Asn Ala
        295                 300                 305 aaa gta gaa gaa tgg aag cta att ttg tct tct aaa gat gat gaa att     1316
Lys Val Glu Glu Trp Lys Leu Ile Leu Ser Ser Lys Asp Asp Glu Ile
        310                 315                 320 att gag tat cag caa atg tta cat aac cta agg gag aaa ctt aag aat     1364
Ile Glu Tyr Gln Gln Met Leu His Asn Leu Arg Glu Lys Leu Lys Asn
325                 330                 335                 340 gct cag ctt gat gct gat aaa agt aat gtt atg gct cta cag cag ggt     1412
Ala Gln Leu Asp Ala Asp Lys Ser Asn Val Met Ala Leu Gln Gln Gly
                345                 350                 355 ata cag gaa cga gac agt caa att aag atg ctc acc gaa caa gta gaa     1460
Ile Gln Glu Arg Asp Ser Gln Ile Lys Met Leu Thr Glu Gln Val Glu
            360                 365                 370 caa tat aca aaa gaa atg gaa aag aat act tgt att att gaa gat ttg     1508
Gln Tyr Thr Lys Glu Met Glu Lys Asn Thr Cys Ile Ile Glu Asp Leu
        375                 380                 385 aaa aat gag ctc caa aga aac aaa ggt gct tca acc ctt tct caa cag     1556
Lys Asn Glu Leu Gln Arg Asn Lys Gly Ala Ser Thr Leu Ser Gln Gln
        390                 395                 400 act cat atg aaa att cag tca acg tta gac att tta aaa gag aaa act     1604
Thr His Met Lys Ile Gln Ser Thr Leu Asp Ile Leu Lys Glu Lys Thr
```

```
                405                 410                 415                 420
aaa gag gct gag aga aca gct gaa ctg gct gag gct gat gct agg gaa          1652
Lys Glu Ala Glu Arg Thr Ala Glu Leu Ala Glu Ala Asp Ala Arg Glu
                    425                 430                 435 aag gat aaa gaa tta gtt gag gct ctg aag agg tta aaa gat tat gaa          1700
Lys Asp Lys Glu Leu Val Glu Ala Leu Lys Arg Leu Lys Asp Tyr Glu
                440                 445                 450 tcg gga gta tat ggt tta gaa gat gct gtc gtt gaa ata aag aat tgt          1748
Ser Gly Val Tyr Gly Leu Glu Asp Ala Val Val Glu Ile Lys Asn Cys
            455                 460                 465 aaa aac caa att aaa ata aga gat cga gag att gaa ata tta aca aag          1796
Lys Asn Gln Ile Lys Ile Arg Asp Arg Glu Ile Glu Ile Leu Thr Lys
        470                 475                 480 gaa atc aat aaa ctt gaa ttg aag atc agt gat ttc ctt gat gaa aat          1844
Glu Ile Asn Lys Leu Glu Leu Lys Ile Ser Asp Phe Leu Asp Glu Asn
485                 490                 495                 500 gag gca ctt aga gag cgt gtg ggc ctt gaa cca aag aca atg att gat          1892
Glu Ala Leu Arg Glu Arg Val Gly Leu Glu Pro Lys Thr Met Ile Asp
                    505                 510                 515 tta act gaa ttt aga aat agc aaa cac tta aaa cag cag cag tac aga          1940
Leu Thr Glu Phe Arg Asn Ser Lys His Leu Lys Gln Gln Gln Tyr Arg
                520                 525                 530 gct gaa aac cag att ctt ttg aaa gag att gaa agt cta gag gaa gaa          1988
Ala Glu Asn Gln Ile Leu Leu Lys Glu Ile Glu Ser Leu Glu Glu Glu
            535                 540                 545 cga ctt gat ctg aaa aaa aaa att cgt caa atg gct caa gaa aga gga          2036
Arg Leu Asp Leu Lys Lys Lys Ile Arg Gln Met Ala Gln Glu Arg Gly
        550                 555                 560 aaa aga agt gca act tca gga tta acc act gag gac ctg aac cta act          2084
Lys Arg Ser Ala Thr Ser Gly Leu Thr Thr Glu Asp Leu Asn Leu Thr
565                 570                 575                 580 gaa aac att tct caa gga gat aga ata agt gaa aga aaa ttg gat tta          2132
Glu Asn Ile Ser Gln Gly Asp Arg Ile Ser Glu Arg Lys Leu Asp Leu
                    585                 590                 595 ttg agc ctc aaa aat atg agt gaa gca caa tca aag aat gaa ttt ctt          2180
Leu Ser Leu Lys Asn Met Ser Glu Ala Gln Ser Lys Asn Glu Phe Leu
                600                 605                 610 tca aga gaa cta att gaa aaa gaa aga gat tta gaa agg agt agg aca          2228
Ser Arg Glu Leu Ile Glu Lys Glu Arg Asp Leu Glu Arg Ser Arg Thr
            615                 620                 625 gtg ata gcc aaa ttt cag aat aaa tta aaa gaa tta gtt gaa gaa aat          2276
Val Ile Ala Lys Phe Gln Asn Lys Leu Lys Glu Leu Val Glu Glu Asn
        630                 635                 640 aag caa ctt gaa gaa ggt atg aaa gaa ata ttg caa gca att aag gaa          2324
Lys Gln Leu Glu Glu Gly Met Lys Glu Ile Leu Gln Ala Ile Lys Glu
645                 650                 655                 660 atg cag aaa gat cct gat gtt aaa gga gga gaa aca tct cta att atc          2372
Met Gln Lys Asp Pro Asp Val Lys Gly Gly Glu Thr Ser Leu Ile Ile
                    665                 670                 675 cct agc ctt gaa aga cta gtt aat gct ata gaa tca aag aat gca gaa          2420
Pro Ser Leu Glu Arg Leu Val Asn Ala Ile Glu Ser Lys Asn Ala Glu
                680                 685                 690 gga atc ttt gat gcg agt ctg cat ttg aaa gcc caa gtt gat cag ctt          2468
Gly Ile Phe Asp Ala Ser Leu His Leu Lys Ala Gln Val Asp Gln Leu
            695                 700                 705 acc gga aga aat gaa gaa tta aga cag gag ctc agg gaa tct cgg aaa          2516
Thr Gly Arg Asn Glu Glu Leu Arg Gln Glu Leu Arg Glu Ser Arg Lys
        710                 715                 720 gag gct ata aat tat tca cag cag ttg gca aaa gct aat tta aag ata          2564
```

```
Glu Ala Ile Asn Tyr Ser Gln Gln Leu Ala Lys Ala Asn Leu Lys Ile
725                 730                 735                 740 gac cat ctt gaa aaa gaa act agt ctt tta cga caa tca gaa gga tcg      2612
Asp His Leu Glu Lys Glu Thr Ser Leu Leu Arg Gln Ser Glu Gly Ser
                745                 750                 755 aat gtt gtt ttt aaa gga att gac tta cct gat ggg ata gca cca tct      2660
Asn Val Val Phe Lys Gly Ile Asp Leu Pro Asp Gly Ile Ala Pro Ser
            760                 765                 770 agt gcc agt atc att aat tct cag aat gaa tat tta ata cat ttg tta      2708
Ser Ala Ser Ile Ile Asn Ser Gln Asn Glu Tyr Leu Ile His Leu Leu
        775                 780                 785 cag gaa cta gaa aat aaa gaa aaa aag tta aag aat tta gaa gat tct      2756
Gln Glu Leu Glu Asn Lys Glu Lys Lys Leu Lys Asn Leu Glu Asp Ser
    790                 795                 800 ctt gaa gat tac aac aga aaa ttt gct gta att cgt cat caa caa agt      2804
Leu Glu Asp Tyr Asn Arg Lys Phe Ala Val Ile Arg His Gln Gln Ser
805                 810                 815                 820 ttg ttg tat aaa gaa tac cta agt gaa aag gag acc tgg aaa aca gaa      2852
Leu Leu Tyr Lys Glu Tyr Leu Ser Glu Lys Glu Thr Trp Lys Thr Glu
                825                 830                 835 tct aaa aca ata aaa gag gaa aag aga aaa ctt gag gat caa gtc caa      2900
Ser Lys Thr Ile Lys Glu Glu Lys Arg Lys Leu Glu Asp Gln Val Gln
            840                 845                 850 caa gat gct ata aaa gta aaa gaa tat aat aat ttg ctc aat gct ctt      2948
Gln Asp Ala Ile Lys Val Lys Glu Tyr Asn Asn Leu Leu Asn Ala Leu
        855                 860                 865 cag atg gat tcg gat gaa atg aaa aaa ata ctt gca gaa aat agt agg      2996
Gln Met Asp Ser Asp Glu Met Lys Lys Ile Leu Ala Glu Asn Ser Arg
    870                 875                 880 aaa att act gtt ttg caa gtg aat gaa aaa tca ctt ata agg caa tat      3044
Lys Ile Thr Val Leu Gln Val Asn Glu Lys Ser Leu Ile Arg Gln Tyr
885                 890                 895                 900 aca acc tta gta gaa ttg gag cga caa ctt aga aaa gaa aat gag aag      3092
Thr Thr Leu Val Glu Leu Glu Arg Gln Leu Arg Lys Glu Asn Glu Lys
                905                 910                 915 caa aag aat gaa ttg ttg tca atg gag gct gaa gtt tgt gaa aaa att      3140
Gln Lys Asn Glu Leu Leu Ser Met Glu Ala Glu Val Cys Glu Lys Ile
            920                 925                 930 ggg tgt ttg caa aga ttt aag gaa atg gcc att ttc aag att gca gct      3188
Gly Cys Leu Gln Arg Phe Lys Glu Met Ala Ile Phe Lys Ile Ala Ala
        935                 940                 945 ctc caa aaa gtt gta gat aat agt gtt tct ttg tct gaa cta gaa ctg      3236
Leu Gln Lys Val Val Asp Asn Ser Val Ser Leu Ser Glu Leu Glu Leu
    950                 955                 960 gct aat aaa cag tac aat gaa ctg act gct aag tac agg gac atc ttg      3284
Ala Asn Lys Gln Tyr Asn Glu Leu Thr Ala Lys Tyr Arg Asp Ile Leu
965                 970                 975                 980 caa aaa gat aat atg ctt gtt caa aga aca agt aac ttg gaa cac ctg      3332
Gln Lys Asp Asn Met Leu Val Gln Arg Thr Ser Asn Leu Glu His Leu
                985                 990                 995 gag tgt gaa aac atc tcc tta aaa gaa caa gtg gag tct ata aat          3377
Glu Cys Glu Asn Ile Ser Leu Lys Glu Gln Val Glu Ser Ile Asn
            1000                1005                1010 aaa gaa ctg gag att acc aag gaa aaa ctt cac act att gaa caa          3422
Lys Glu Leu Glu Ile Thr Lys Glu Lys Leu His Thr Ile Glu Gln
        1015                1020                1025 gcc tgg gaa cag gaa act aaa tta ggt aat gaa tct agc atg gat          3467
Ala Trp Glu Gln Glu Thr Lys Leu Gly Asn Glu Ser Ser Met Asp
    1030                1035                1040
```

| | | | | | | | | | | | | |
|---|---|---|---|---|---|---|---|---|---|---|---|---|
| aag | gca | aag | aaa | tca | ata | acc | aac | agt | gac | att | gtt | tcc | att | tca | 3512 |
| Lys | Ala | Lys | Lys | Ser | Ile | Thr | Asn | Ser | Asp | Ile | Val | Ser | Ile | Ser | |
| | | 1045 | | | | 1050 | | | | | 1055 | | | | |
| aaa | aaa | ata | act | atg | ctg | gaa | atg | aag | gaa | tta | aat | gaa | agg | cag | 3557 |
| Lys | Lys | Ile | Thr | Met | Leu | Glu | Met | Lys | Glu | Leu | Asn | Glu | Arg | Gln | |
| | | | 1060 | | | | 1065 | | | | | 1070 | | | |
| cgg | gct | gaa | cat | tgt | caa | aaa | atg | tat | gaa | cac | tta | cgg | act | tcg | 3602 |
| Arg | Ala | Glu | His | Cys | Gln | Lys | Met | Tyr | Glu | His | Leu | Arg | Thr | Ser | |
| | 1075 | | | | | 1080 | | | | | 1085 | | | | |
| tta | aag | caa | atg | gag | gaa | cgt | aat | ttt | gaa | ttg | gaa | acc | aaa | ttt | 3647 |
| Leu | Lys | Gln | Met | Glu | Glu | Arg | Asn | Phe | Glu | Leu | Glu | Thr | Lys | Phe | |
| | | | 1090 | | | | 1095 | | | | | 1100 | | | |
| gct | gag | ctt | acc | aaa | atc | aat | ttg | gat | gca | cag | aag | gtg | gaa | cag | 3692 |
| Ala | Glu | Leu | Thr | Lys | Ile | Asn | Leu | Asp | Ala | Gln | Lys | Val | Glu | Gln | |
| | | 1105 | | | | | 1110 | | | | | 1115 | | | |
| atg | tta | aga | gat | gaa | tta | gct | gat | agt | gtg | agc | aag | gca | gta | agt | 3737 |
| Met | Leu | Arg | Asp | Glu | Leu | Ala | Asp | Ser | Val | Ser | Lys | Ala | Val | Ser | |
| | | | 1120 | | | | 1125 | | | | | 1130 | | | |
| gat | gct | gat | agg | caa | cgg | att | cta | gaa | tta | gag | aag | aat | gaa | atg | 3782 |
| Asp | Ala | Asp | Arg | Gln | Arg | Ile | Leu | Glu | Leu | Glu | Lys | Asn | Glu | Met | |
| | 1135 | | | | | 1140 | | | | | 1145 | | | | |
| gaa | cta | aaa | gtt | gaa | gtg | tca | aaa | ctg | aga | gag | att | tct | gat | att | 3827 |
| Glu | Leu | Lys | Val | Glu | Val | Ser | Lys | Leu | Arg | Glu | Ile | Ser | Asp | Ile | |
| | | 1150 | | | | | 1155 | | | | | 1160 | | | |
| gcc | aga | aga | caa | gtt | gaa | att | ttg | aat | gca | caa | caa | caa | tct | agg | 3872 |
| Ala | Arg | Arg | Gln | Val | Glu | Ile | Leu | Asn | Ala | Gln | Gln | Gln | Ser | Arg | |
| | 1165 | | | | | 1170 | | | | | 1175 | | | | |
| gac | aag | gaa | gta | gag | tcc | ctc | aga | atg | caa | ctg | cta | gac | tat | cag | 3917 |
| Asp | Lys | Glu | Val | Glu | Ser | Leu | Arg | Met | Gln | Leu | Leu | Asp | Tyr | Gln | |
| | | 1180 | | | | | 1185 | | | | | 1190 | | | |
| gca | cag | tct | gat | gaa | aag | tcg | ctc | att | gcc | aag | ttg | cac | caa | cat | 3962 |
| Ala | Gln | Ser | Asp | Glu | Lys | Ser | Leu | Ile | Ala | Lys | Leu | His | Gln | His | |
| | 1195 | | | | | 1200 | | | | | 1205 | | | | |
| aat | gtc | tct | ctt | caa | ctg | agt | gag | gct | act | gct | ctt | ggt | aag | ttg | 4007 |
| Asn | Val | Ser | Leu | Gln | Leu | Ser | Glu | Ala | Thr | Ala | Leu | Gly | Lys | Leu | |
| | | 1210 | | | | | 1215 | | | | | 1220 | | | |
| gag | tca | att | aca | tct | aaa | ctg | cag | aag | atg | gag | gcc | tac | aac | ttg | 4052 |
| Glu | Ser | Ile | Thr | Ser | Lys | Leu | Gln | Lys | Met | Glu | Ala | Tyr | Asn | Leu | |
| | | 1225 | | | | | 1230 | | | | | 1235 | | | |
| cgc | tta | gag | cag | aaa | ctt | gat | gaa | aaa | gaa | cag | gct | ctc | tat | tat | 4097 |
| Arg | Leu | Glu | Gln | Lys | Leu | Asp | Glu | Lys | Glu | Gln | Ala | Leu | Tyr | Tyr | |
| | | 1240 | | | | | 1245 | | | | | 1250 | | | |
| gct | cgt | ttg | gag | gga | aga | aac | aga | gca | aaa | cat | ctg | cgc | caa | aca | 4142 |
| Ala | Arg | Leu | Glu | Gly | Arg | Asn | Arg | Ala | Lys | His | Leu | Arg | Gln | Thr | |
| | 1255 | | | | | 1260 | | | | | 1265 | | | | |
| att | cag | tct | cta | cga | cga | cag | ttt | agt | gga | gct | tta | ccc | ttg | gca | 4187 |
| Ile | Gln | Ser | Leu | Arg | Arg | Gln | Phe | Ser | Gly | Ala | Leu | Pro | Leu | Ala | |
| | | 1270 | | | | | 1275 | | | | | 1280 | | | |
| caa | cag | gaa | aag | ttc | tcc | aaa | aca | atg | att | caa | cta | caa | aat | gac | 4232 |
| Gln | Gln | Glu | Lys | Phe | Ser | Lys | Thr | Met | Ile | Gln | Leu | Gln | Asn | Asp | |
| | 1285 | | | | | 1290 | | | | | 1295 | | | | |
| aaa | ctt | aag | ata | atg | caa | gaa | atg | aaa | aat | tct | caa | caa | gaa | cat | 4277 |
| Lys | Leu | Lys | Ile | Met | Gln | Glu | Met | Lys | Asn | Ser | Gln | Gln | Glu | His | |
| | | 1300 | | | | | 1305 | | | | | 1310 | | | |
| aga | aat | atg | gag | aac | aaa | aca | ttg | gag | atg | gaa | tta | aaa | tta | aag | 4322 |
| Arg | Asn | Met | Glu | Asn | Lys | Thr | Leu | Glu | Met | Glu | Leu | Lys | Leu | Lys | |
| | | 1315 | | | | | 1320 | | | | | 1325 | | | |
| ggc | ctg | gaa | gag | tta | ata | agc | act | tta | aag | gat | acc | aaa | gga | gcc | 4367 |
| Gly | Leu | Glu | Glu | Leu | Ile | Ser | Thr | Leu | Lys | Asp | Thr | Lys | Gly | Ala | |
| | | 1330 | | | | | 1335 | | | | | 1340 | | | |

```
caa aag gta atc aac tgg cat atg aaa ata gaa gaa ctt cgt ctt      4412
Gln Lys Val Ile Asn Trp His Met Lys Ile Glu Glu Leu Arg Leu
        1345                1350                1355 caa gaa ctt aaa cta aat cgg gaa tta gtc aag gat aaa gaa gaa      4457
Gln Glu Leu Lys Leu Asn Arg Glu Leu Val Lys Asp Lys Glu Glu
    1360                1365                1370 ata aaa tat ttg aat aac ata att tct gaa tat gaa cgt aca atc      4502
Ile Lys Tyr Leu Asn Asn Ile Ile Ser Glu Tyr Glu Arg Thr Ile
1375                1380                1385 agc agt ctt gaa gaa gaa att gtg caa cag aac aag ttt cat gaa      4547
Ser Ser Leu Glu Glu Glu Ile Val Gln Gln Asn Lys Phe His Glu
            1390                1395                1400 gaa aga caa atg gcc tgg gat caa aga gaa gtt gac ctg gaa cgc      4592
Glu Arg Gln Met Ala Trp Asp Gln Arg Glu Val Asp Leu Glu Arg
        1405                1410                1415 caa cta gac att ttt gac cgt cag caa aat gaa ata cta aat gcg      4637
Gln Leu Asp Ile Phe Asp Arg Gln Gln Asn Glu Ile Leu Asn Ala
    1420                1425                1430 gca caa aag ttt gaa gaa gct aca gga tca atc cct gac cct agt      4682
Ala Gln Lys Phe Glu Glu Ala Thr Gly Ser Ile Pro Asp Pro Ser
1435                1440                1445 ttg ccc ctt cca aat caa ctt gag atc gct cta agg aaa att aag      4727
Leu Pro Leu Pro Asn Gln Leu Glu Ile Ala Leu Arg Lys Ile Lys
            1450                1455                1460 gag aac att cga ata att cta gaa aca cgg gca act tgc aaa tca      4772
Glu Asn Ile Arg Ile Ile Leu Glu Thr Arg Ala Thr Cys Lys Ser
        1465                1470                1475 cta gaa gag aaa cta aaa gag aaa gaa tct gct tta agg tta gca      4817
Leu Glu Glu Lys Leu Lys Glu Lys Glu Ser Ala Leu Arg Leu Ala
    1480                1485                1490 gaa caa aat ata ctg tca aga gac aaa gta atc aat gaa ctg agg      4862
Glu Gln Asn Ile Leu Ser Arg Asp Lys Val Ile Asn Glu Leu Arg
1495                1500                1505 ctt cga ttg cct gcc act gca gaa aga gaa aag ctc ata gct gag      4907
Leu Arg Leu Pro Ala Thr Ala Glu Arg Glu Lys Leu Ile Ala Glu
            1510                1515                1520 cta ggc aga aaa gag atg gaa cca aaa tct cac cac aca ttg aaa      4952
Leu Gly Arg Lys Glu Met Glu Pro Lys Ser His His Thr Leu Lys
        1525                1530                1535 att gct cat caa acc att gca aac atg caa gca agg tta aat caa      4997
Ile Ala His Gln Thr Ile Ala Asn Met Gln Ala Arg Leu Asn Gln
    1540                1545                1550 aaa gaa gaa gta tta aag aag tat caa cgt ctt cta gaa aaa gcc      5042
Lys Glu Glu Val Leu Lys Lys Tyr Gln Arg Leu Leu Glu Lys Ala
1555                1560                1565 aga gag gag caa aga gaa att gtg aag aaa cat gag gaa gac ctt      5087
Arg Glu Glu Gln Arg Glu Ile Val Lys Lys His Glu Glu Asp Leu
            1570                1575                1580 cat att ctt cat cac aga tta gaa cta cag gct gat agt tca cta      5132
His Ile Leu His His Arg Leu Glu Leu Gln Ala Asp Ser Ser Leu
        1585                1590                1595 aat aaa ttc aaa caa acg gct tgg gat tta atg aaa cag tct ccc      5177
Asn Lys Phe Lys Gln Thr Ala Trp Asp Leu Met Lys Gln Ser Pro
    1600                1605                1610 act cca gtt cct acc aac aag cat ttt att cgt ctg gct gag atg      5222
Thr Pro Val Pro Thr Asn Lys His Phe Ile Arg Leu Ala Glu Met
1615                1620                1625 gaa cag aca gta gca gaa caa gat gac tct ctt tcc tca ctc ttg      5267
Glu Gln Thr Val Ala Glu Gln Asp Asp Ser Leu Ser Ser Leu Leu
```

-continued

|  | 1630 |  |  |  | 1635 |  |  |  | 1640 |  |  |  |  |
|---|---|---|---|---|---|---|---|---|---|---|---|---|---|
| gtc | aaa | cta | aag | aaa | gta | tca | caa | gat | ttg | gag | aga | caa | aga | gaa | 5312 |
| Val | Lys | Leu | Lys | Lys | Val | Ser | Gln | Asp | Leu | Glu | Arg | Gln | Arg | Glu |  |
|  | 1645 |  |  |  | 1650 |  |  |  | 1655 |  |  |  |  |

```
gtc aaa cta aag aaa gta tca caa gat ttg gag aga caa aga gaa    5312
Val Lys Leu Lys Lys Val Ser Gln Asp Leu Glu Arg Gln Arg Glu
        1645            1650                1655 atc act gaa tta aaa gta aaa gaa ttt gaa aat atc aaa tta cag    5357
Ile Thr Glu Leu Lys Val Lys Glu Phe Glu Asn Ile Lys Leu Gln
        1660            1665                1670 ctt caa gaa aac cat gaa gat gaa gtg aaa aaa gta aaa gcg gaa    5402
Leu Gln Glu Asn His Glu Asp Glu Val Lys Lys Val Lys Ala Glu
        1675            1680                1685 gta gag gat tta aag tat ctt ctg gac cag tca caa aag gag tca    5447
Val Glu Asp Leu Lys Tyr Leu Leu Asp Gln Ser Gln Lys Glu Ser
        1690            1695                1700 cag tgt tta aaa tct gaa ctt cag gct caa aaa gaa gca aat tca    5492
Gln Cys Leu Lys Ser Glu Leu Gln Ala Gln Lys Glu Ala Asn Ser
        1705            1710                1715 aga gct cca aca act aca atg aga aat cta gta gaa cgg cta aag    5537
Arg Ala Pro Thr Thr Thr Met Arg Asn Leu Val Glu Arg Leu Lys
        1720            1725                1730 agc caa tta gcc ttg aag gag aaa caa cag aaa gca ctt agt cgg    5582
Ser Gln Leu Ala Leu Lys Glu Lys Gln Gln Lys Ala Leu Ser Arg
        1735            1740                1745 gca ctt tta gaa ctc cgg gca gaa atg aca gca gct gct gaa gaa    5627
Ala Leu Leu Glu Leu Arg Ala Glu Met Thr Ala Ala Ala Glu Glu
        1750            1755                1760 cgt att att tct gca act tct caa aaa gag gcc cat ctc aat gtt    5672
Arg Ile Ile Ser Ala Thr Ser Gln Lys Glu Ala His Leu Asn Val
        1765            1770                1775 caa caa atc gtt gat cga cat act aga gag cta aag aca caa gtt    5717
Gln Gln Ile Val Asp Arg His Thr Arg Glu Leu Lys Thr Gln Val
        1780            1785                1790 gaa gat tta aat gaa aat ctt tta aaa ttg aaa gaa gca ctt aaa    5762
Glu Asp Leu Asn Glu Asn Leu Leu Lys Leu Lys Glu Ala Leu Lys
        1795            1800                1805 aca agt aaa aac aga gaa aac tca cta act gat aat ttg aat gac    5807
Thr Ser Lys Asn Arg Glu Asn Ser Leu Thr Asp Asn Leu Asn Asp
        1810            1815                1820 tta aat aat gaa ctg caa aag aaa caa aaa gcc tat aat aaa ata    5852
Leu Asn Asn Glu Leu Gln Lys Lys Gln Lys Ala Tyr Asn Lys Ile
        1825            1830                1835 ctt aga gag aaa gag gaa att gat caa gag aat gat gaa ctg aaa    5897
Leu Arg Glu Lys Glu Glu Ile Asp Gln Glu Asn Asp Glu Leu Lys
        1840            1845                1850 agg caa att aaa aga cta acc agt gga tta cag ggc aaa ccc ctg    5942
Arg Gln Ile Lys Arg Leu Thr Ser Gly Leu Gln Gly Lys Pro Leu
        1855            1860                1865 aca gat aat aaa caa agt cta att gaa gaa ctc caa agg aaa gtt    5987
Thr Asp Asn Lys Gln Ser Leu Ile Glu Glu Leu Gln Arg Lys Val
        1870            1875                1880 aaa aaa cta gag aac caa tta gag gga aag gtg gag gaa gta gac    6032
Lys Lys Leu Glu Asn Gln Leu Glu Gly Lys Val Glu Glu Val Asp
        1885            1890                1895 cta aaa cct atg aaa gaa aag aat gct aaa gaa gaa tta att agg    6077
Leu Lys Pro Met Lys Glu Lys Asn Ala Lys Glu Glu Leu Ile Arg
        1900            1905                1910 tgg gaa gaa ggt aaa aag tgg caa gcc aaa ata gaa gga att cga    6122
Trp Glu Glu Gly Lys Lys Trp Gln Ala Lys Ile Glu Gly Ile Arg
        1915            1920                1925 aac aag tta aaa gag aaa gag ggg gaa gtc ttt act tta aca aag    6167
```

|  |  |  |  |  |  |  |  |  |  |  |  |  |  |  |
|---|---|---|---|---|---|---|---|---|---|---|---|---|---|---|
| Asn | Lys | Leu | Lys<br>1930 | Glu | Lys | Glu | Gly<br>1935 | Glu | Val | Phe | Thr | Leu<br>1940 | Thr | Lys |

| cag | ttg | aat | act | ttg | aag | gat | ctt | ttt | gcc | aaa | gcc | gat | aaa | gag | 6212 |
|---|---|---|---|---|---|---|---|---|---|---|---|---|---|---|---|
| Gln | Leu | Asn | Thr<br>1945 | Leu | Lys | Asp | Leu<br>1950 | Phe | Ala | Lys | Ala | Asp<br>1955 | Lys | Glu | |

| aaa | ctt | act | ttg | cag | agg | aaa | cta | aaa | aca | act | ggc | atg | act | gtt | 6257 |
|---|---|---|---|---|---|---|---|---|---|---|---|---|---|---|---|
| Lys | Leu | Thr | Leu<br>1960 | Gln | Arg | Lys | Leu<br>1965 | Lys | Thr | Thr | Gly | Met<br>1970 | Thr | Val | |

| gat | cag | gtt | ttg | gga | ata | cga | gct | ttg | gag | tca | gaa | aaa | gaa | ttg | 6302 |
|---|---|---|---|---|---|---|---|---|---|---|---|---|---|---|---|
| Asp | Gln | Val | Leu<br>1975 | Gly | Ile | Arg | Ala<br>1980 | Leu | Glu | Ser | Glu | Lys<br>1985 | Glu | Leu | |

| gaa | gaa | tta | aaa | aag | aga | aat | ctt | gac | tta | gaa | aat | gat | ata | ttg | 6347 |
|---|---|---|---|---|---|---|---|---|---|---|---|---|---|---|---|
| Glu | Glu | Leu | Lys<br>1990 | Lys | Arg | Asn | Leu<br>1995 | Asp | Leu | Glu | Asn | Asp<br>2000 | Ile | Leu | |

| tat | atg | agg | gcc | cac | caa | gct | ctt | cct | cga | gat | tct | gtt | gta | gaa | 6392 |
|---|---|---|---|---|---|---|---|---|---|---|---|---|---|---|---|
| Tyr | Met | Arg | Ala<br>2005 | His | Gln | Ala | Leu<br>2010 | Pro | Arg | Asp | Ser | Val<br>2015 | Val | Glu | |

| gat | tta | cat | tta | caa | aat | aga | tac | ctc | caa | gaa | aaa | ctt | cat | gct | 6437 |
|---|---|---|---|---|---|---|---|---|---|---|---|---|---|---|---|
| Asp | Leu | His | Leu<br>2020 | Gln | Asn | Arg | Tyr<br>2025 | Leu | Gln | Glu | Lys | Leu<br>2030 | His | Ala | |

| tta | gaa | aaa | cag | ttt | tca | aag | gat | aca | tat | tct | aag | cct | tca | att | 6482 |
|---|---|---|---|---|---|---|---|---|---|---|---|---|---|---|---|
| Leu | Glu | Lys | Gln<br>2035 | Phe | Ser | Lys | Asp<br>2040 | Thr | Tyr | Ser | Lys | Pro<br>2045 | Ser | Ile | |

| tca | gga | ata | gag | tca | gat | gat | cat | tgt | cag | aga | gaa | cag | gag | ctt | 6527 |
|---|---|---|---|---|---|---|---|---|---|---|---|---|---|---|---|
| Ser | Gly | Ile | Glu<br>2050 | Ser | Asp | Asp | His<br>2055 | Cys | Gln | Arg | Glu | Gln<br>2060 | Glu | Leu | |

| cag | aag | gaa | aac | ttg | aag | ttg | tca | tct | gaa | aat | att | gaa | ctg | aaa | 6572 |
|---|---|---|---|---|---|---|---|---|---|---|---|---|---|---|---|
| Gln | Lys | Glu | Asn<br>2065 | Leu | Lys | Leu | Ser<br>2070 | Ser | Glu | Asn | Ile | Glu<br>2075 | Leu | Lys | |

| ttt | cag | ctt | gaa | caa | gca | aat | aaa | gat | ttg | cca | aga | tta | aag | aat | 6617 |
|---|---|---|---|---|---|---|---|---|---|---|---|---|---|---|---|
| Phe | Gln | Leu | Glu<br>2080 | Gln | Ala | Asn | Lys<br>2085 | Asp | Leu | Pro | Arg | Leu<br>2090 | Lys | Asn | |

| caa | gtc | aga | gat | ttg | aag | gaa | atg | tgt | gaa | ttt | ctt | aag | aaa | gaa | 6662 |
|---|---|---|---|---|---|---|---|---|---|---|---|---|---|---|---|
| Gln | Val | Arg | Asp<br>2095 | Leu | Lys | Glu | Met<br>2100 | Cys | Glu | Phe | Leu | Lys<br>2105 | Lys | Glu | |

| aaa | gca | gaa | gtt | cag | cgg | aaa | ctt | ggc | cat | gtt | aga | ggg | tct | ggt | 6707 |
|---|---|---|---|---|---|---|---|---|---|---|---|---|---|---|---|
| Lys | Ala | Glu | Val<br>2110 | Gln | Arg | Lys | Leu<br>2115 | Gly | His | Val | Arg | Gly<br>2120 | Ser | Gly | |

| aga | agt | gga | aag | aca | atc | cca | gaa | ctg | gaa | aaa | acc | att | ggt | tta | 6752 |
|---|---|---|---|---|---|---|---|---|---|---|---|---|---|---|---|
| Arg | Ser | Gly | Lys<br>2125 | Thr | Ile | Pro | Glu<br>2130 | Leu | Glu | Lys | Thr | Ile<br>2135 | Gly | Leu | |

| atg | aaa | aaa | gta | gtt | gaa | aaa | gtc | cag | aga | gaa | aat | gaa | cag | ttg | 6797 |
|---|---|---|---|---|---|---|---|---|---|---|---|---|---|---|---|
| Met | Lys | Lys | Val<br>2140 | Val | Glu | Lys | Val<br>2145 | Gln | Arg | Glu | Asn | Glu<br>2150 | Gln | Leu | |

| aaa | aaa | gca | tca | gga | ata | ttg | act | agt | gaa | aaa | atg | gct | aat | att | 6842 |
|---|---|---|---|---|---|---|---|---|---|---|---|---|---|---|---|
| Lys | Lys | Ala | Ser<br>2155 | Gly | Ile | Leu | Thr<br>2160 | Ser | Glu | Lys | Met | Ala<br>2165 | Asn | Ile | |

| gag | cag | gaa | aat | gaa | aaa | ttg | aag | gct | gaa | tta | gaa | aaa | ctt | aaa | 6887 |
|---|---|---|---|---|---|---|---|---|---|---|---|---|---|---|---|
| Glu | Gln | Glu | Asn<br>2170 | Glu | Lys | Leu | Lys<br>2175 | Ala | Glu | Leu | Glu | Lys<br>2180 | Leu | Lys | |

| gct | cat | ctt | ggg | cat | cag | ttg | agc | atg | cac | tat | gaa | tcc | aag | acc | 6932 |
|---|---|---|---|---|---|---|---|---|---|---|---|---|---|---|---|
| Ala | His | Leu | Gly<br>2185 | His | Gln | Leu | Ser<br>2190 | Met | His | Tyr | Glu | Ser<br>2195 | Lys | Thr | |

| aaa | ggc | aca | gaa | aaa | att | att | gct | gaa | aat | gaa | agg | ctt | cgt | aaa | 6977 |
|---|---|---|---|---|---|---|---|---|---|---|---|---|---|---|---|
| Lys | Gly | Thr | Glu<br>2200 | Lys | Ile | Ile | Ala<br>2205 | Glu | Asn | Glu | Arg | Leu<br>2210 | Arg | Lys | |

| gaa | ctt | aaa | aaa | gaa | act | gat | gct | gca | gag | aaa | tta | cgg | ata | gca | 7022 |
|---|---|---|---|---|---|---|---|---|---|---|---|---|---|---|---|
| Glu | Leu | Lys | Lys<br>2215 | Glu | Thr | Asp | Ala<br>2220 | Ala | Glu | Lys | Leu | Arg<br>2225 | Ile | Ala | |

| | | | | | | | | | | | | |
|---|---|---|---|---|---|---|---|---|---|---|---|---|
| aag | aat | aat | tta | gag | ata | tta | aat | gag | aag | atg | aca | gtt | caa | cta | 7067 |
| Lys | Asn | Asn | Leu | Glu | Ile | Leu | Asn | Glu | Lys | Met | Thr | Val | Gln | Leu | |
| | | | 2230 | | | | | 2235 | | | | | 2240 | | | gaa gag act ggt aag aga ttg cag ttt gca gaa agc aga ggt cca 7112
Glu Glu Thr Gly Lys Arg Leu Gln Phe Ala Glu Ser Arg Gly Pro
           2245              2250              2255 cag ctt gaa ggt gct gac agt aag agc tgg aaa tcc att gtg gtt 7157
Gln Leu Glu Gly Ala Asp Ser Lys Ser Trp Lys Ser Ile Val Val
           2260              2265              2270 aca aga atg tat gaa acc aag tta aaa gaa ttg gaa act gat att 7202
Thr Arg Met Tyr Glu Thr Lys Leu Lys Glu Leu Glu Thr Asp Ile
           2275              2280              2285 gcc aaa aaa aat caa agc att act gac ctt aaa cag ctt gta aaa 7247
Ala Lys Lys Asn Gln Ser Ile Thr Asp Leu Lys Gln Leu Val Lys
           2290              2295              2300 gaa gca aca gag aga gaa caa aaa gtt aac aaa tac aat gaa gac 7292
Glu Ala Thr Glu Arg Glu Gln Lys Val Asn Lys Tyr Asn Glu Asp
           2305              2310              2315 ctt gaa caa cag att aag att ctt aaa cat gtt cct gaa ggt gct 7337
Leu Glu Gln Gln Ile Lys Ile Leu Lys His Val Pro Glu Gly Ala
           2320              2325              2330 gag aca gag caa ggc ctt aaa cgg gag ctt caa gtt ctt aga tta 7382
Glu Thr Glu Gln Gly Leu Lys Arg Glu Leu Gln Val Leu Arg Leu
           2335              2340              2345 gct aat cat cag ctg gat aaa gag aaa gca gaa tta atc cat cag 7427
Ala Asn His Gln Leu Asp Lys Glu Lys Ala Glu Leu Ile His Gln
           2350              2355              2360 ata gaa gct aac aag gac caa agt gga gct gaa agc acc ata cct 7472
Ile Glu Ala Asn Lys Asp Gln Ser Gly Ala Glu Ser Thr Ile Pro
           2365              2370              2375 gat gct gat caa cta aag gaa aaa ata aaa gat cta gag aca cag 7517
Asp Ala Asp Gln Leu Lys Glu Lys Ile Lys Asp Leu Glu Thr Gln
           2380              2385              2390 ctc aaa atg tca gat cta gaa aag cag cat ttg aag gag gaa ata 7562
Leu Lys Met Ser Asp Leu Glu Lys Gln His Leu Lys Glu Glu Ile
           2395              2400              2405 aag aag ctg aaa aaa gaa ctg gaa aat ttt gat cct tca ttt ttt 7607
Lys Lys Leu Lys Lys Glu Leu Glu Asn Phe Asp Pro Ser Phe Phe
           2410              2415              2420 gaa gaa att gaa gat ctt aag tat aat tac aag gaa gaa gtg aag 7652
Glu Glu Ile Glu Asp Leu Lys Tyr Asn Tyr Lys Glu Glu Val Lys
           2425              2430              2435 aag aat att ctc tta gaa gag aag gta aaa aaa ctt tca gaa caa 7697
Lys Asn Ile Leu Leu Glu Glu Lys Val Lys Lys Leu Ser Glu Gln
           2440              2445              2450 ttg gga gtt gaa tta act agc cct gtt gct gct tct gaa gag ttt 7742
Leu Gly Val Glu Leu Thr Ser Pro Val Ala Ala Ser Glu Glu Phe
           2455              2460              2465 gaa gat gaa gaa gaa agt cct gtt aat ttc ccc att tac taaaggtcac 7791
Glu Asp Glu Glu Glu Ser Pro Val Asn Phe Pro Ile Tyr
           2470              2475 ctataaactt tgtttcattt aactatttat taactttata agttaaatat acttggaaat   7851
aagcagttct ccgaactgta gtatttcctt ctcactacct tgtaccttta tacttagatt   7911
ggaattctta ataaataaaa ttatatgaaa ttttcaactt attaaaaaaa aaaaaaaaaa   7971
a                                                                    7972

<210> SEQ ID NO 3
<211> LENGTH: 2479

```
<212> TYPE: PRT
<213> ORGANISM: Homo sapiens

<400> SEQUENCE: 3

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
                20                  25                  30

Ser Lys Val Glu Val Asn Glu Leu Lys Ser Lys Gln Glu Asn Val
            35                  40                  45

Ile His Leu Phe Arg Ile Thr Gln Ser Leu Met Lys Met Lys Ala Gln
    50                  55                  60

Glu Val Glu Leu Ala Leu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
                100                 105                 110

Leu Arg Asn Glu Ile Cys Gln Leu Glu Lys Gln Leu Glu Gln Lys Asp
                115                 120                 125

Arg Glu Leu Glu Asp Met Glu Lys Glu Leu Glu Lys Glu Lys Lys Val
                130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Asn Glu Gln Leu
                165                 170                 175

Cys Gln Asp Ile Ile Asp Tyr Gln Lys Gln Ile Asp Ser Gln Lys Glu
                180                 185                 190

Thr Leu Leu Ser Arg Arg Gly Glu Asp Ser Asp Tyr Arg Ser Gln Leu
                195                 200                 205

Ser Lys Lys Asn Tyr Glu Leu Ile Gln Tyr Leu Asp Glu Ile Gln Thr
            210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                245                 250                 255

Tyr Asn Arg Met Lys Ala Ile Val His Gln Thr Asp Asn Val Ile Asp
                260                 265                 270

Gln Leu Lys Lys Glu Asn Asp His Tyr Gln Leu Gln Val Gln Glu Leu
                275                 280                 285

Thr Asp Leu Leu Lys Ser Lys Asn Glu Glu Asp Asp Pro Ile Met Val
290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
                340                 345                 350

Leu Gln Gln Gly Ile Gln Glu Arg Asp Ser Gln Ile Lys Met Leu Thr
                355                 360                 365

Glu Gln Val Glu Gln Tyr Thr Lys Glu Met Lys Asn Thr Cys Ile
                370                 375                 380

Ile Glu Asp Leu Lys Asn Glu Leu Gln Arg Asn Lys Gly Ala Ser Thr
385                 390                 395                 400
```

```
Leu Ser Gln Gln Thr His Met Lys Ile Gln Ser Thr Leu Asp Ile Leu
                405                 410                 415
Lys Glu Lys Thr Lys Glu Ala Glu Arg Thr Ala Glu Leu Ala Glu Ala
            420                 425                 430
Asp Ala Arg Glu Lys Asp Lys Glu Leu Val Glu Ala Leu Lys Arg Leu
            435                 440                 445
Lys Asp Tyr Glu Ser Gly Val Tyr Gly Leu Glu Asp Ala Val Val Glu
            450                 455                 460
Ile Lys Asn Cys Lys Asn Gln Ile Lys Ile Arg Asp Arg Glu Ile Glu
465                 470                 475                 480
Ile Leu Thr Lys Glu Ile Asn Lys Leu Glu Leu Lys Ile Ser Asp Phe
                485                 490                 495
Leu Asp Glu Asn Glu Ala Leu Arg Glu Arg Val Gly Leu Glu Pro Lys
                500                 505                 510
Thr Met Ile Asp Leu Thr Glu Phe Arg Asn Ser Lys His Leu Lys Gln
                515                 520                 525
Gln Gln Tyr Arg Ala Glu Asn Gln Ile Leu Leu Lys Glu Ile Glu Ser
            530                 535                 540
Leu Glu Glu Glu Arg Leu Asp Leu Lys Lys Lys Ile Arg Gln Met Ala
545                 550                 555                 560
Gln Glu Arg Gly Lys Arg Ser Ala Thr Ser Gly Leu Thr Thr Glu Asp
                565                 570                 575
Leu Asn Leu Thr Glu Asn Ile Ser Gln Gly Asp Arg Ile Ser Glu Arg
            580                 585                 590
Lys Leu Asp Leu Leu Ser Leu Lys Asn Met Ser Glu Ala Gln Ser Lys
            595                 600                 605
Asn Glu Phe Leu Ser Arg Glu Leu Ile Glu Lys Glu Arg Asp Leu Glu
            610                 615                 620
Arg Ser Arg Thr Val Ile Ala Lys Phe Gln Asn Lys Leu Lys Glu Leu
625                 630                 635                 640
Val Glu Glu Asn Lys Gln Leu Glu Glu Gly Met Lys Glu Ile Leu Gln
                645                 650                 655
Ala Ile Lys Glu Met Gln Lys Asp Pro Asp Val Lys Gly Gly Glu Thr
            660                 665                 670
Ser Leu Ile Ile Pro Ser Leu Glu Arg Leu Val Asn Ala Ile Glu Ser
            675                 680                 685
Lys Asn Ala Glu Gly Ile Phe Asp Ala Ser Leu His Leu Lys Ala Gln
            690                 695                 700
Val Asp Gln Leu Thr Gly Arg Asn Glu Glu Leu Arg Gln Glu Leu Arg
705                 710                 715                 720
Glu Ser Arg Lys Glu Ala Ile Asn Tyr Ser Gln Gln Leu Ala Lys Ala
                725                 730                 735
Asn Leu Lys Ile Asp His Leu Glu Lys Glu Thr Ser Leu Leu Arg Gln
            740                 745                 750
Ser Glu Gly Ser Asn Val Val Phe Lys Gly Ile Asp Leu Pro Asp Gly
            755                 760                 765
Ile Ala Pro Ser Ser Ala Ser Ile Ile Asn Ser Gln Asn Glu Tyr Leu
            770                 775                 780
Ile His Leu Leu Gln Glu Leu Glu Asn Lys Glu Lys Lys Leu Lys Asn
785                 790                 795                 800
Leu Glu Asp Ser Leu Glu Asp Tyr Asn Arg Lys Phe Ala Val Ile Arg
                805                 810                 815
```

-continued

His Gln Gln Ser Leu Leu Tyr Lys Glu Tyr Leu Ser Glu Lys Glu Thr
            820                 825                 830

Trp Lys Thr Glu Ser Lys Thr Ile Lys Glu Glu Lys Arg Lys Leu Glu
            835                 840                 845

Asp Gln Val Gln Gln Asp Ala Ile Lys Val Lys Glu Tyr Asn Asn Leu
            850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
            885                 890                 895

Ile Arg Gln Tyr Thr Thr Leu Val Glu Leu Glu Arg Gln Leu Arg Lys
            900                 905                 910

Glu Asn Glu Lys Gln Lys Asn Glu Leu Leu Ser Met Glu Ala Glu Val
            915                 920                 925

Cys Glu Lys Ile Gly Cys Leu Gln Arg Phe Lys Glu Met Ala Ile Phe
            930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
            965                 970                 975

Arg Asp Ile Leu Gln Lys Asp Asn Met Leu Val Gln Arg Thr Ser Asn
            980                 985                 990

Leu Glu His Leu Glu Cys Glu Asn Ile Ser Leu Lys Glu Gln Val Glu
            995                 1000                1005

Ser Ile Asn Lys Glu Leu Glu Ile Thr Lys Glu Lys Leu His Thr
            1010                1015                1020

Ile Glu Gln Ala Trp Glu Gln Glu Thr Lys Leu Gly Asn Glu Ser
            1025                1030                1035

Ser Met Asp Lys Ala Lys Lys Ser Ile Thr Asn Ser Asp Ile Val
            1040                1045                1050

Ser Ile Ser Lys Lys Ile Thr Met Leu Glu Met Lys Glu Leu Asn
            1055                1060                1065

Glu Arg Gln Arg Ala Glu His Cys Gln Lys Met Tyr Glu His Leu
            1070                1075                1080

Arg Thr Ser Leu Lys Gln Met Glu Glu Arg Asn Phe Glu Leu Glu
            1085                1090                1095

Thr Lys Phe Ala Glu Leu Thr Lys Ile Asn Leu Asp Ala Gln Lys
            1100                1105                1110

Val Glu Gln Met Leu Arg Asp Glu Leu Ala Asp Ser Val Ser Lys
            1115                1120                1125

Ala Val Ser Asp Ala Asp Arg Gln Arg Ile Leu Glu Leu Glu Lys
            1130                1135                1140

Asn Glu Met Glu Leu Lys Val Glu Val Ser Lys Leu Arg Glu Ile
            1145                1150                1155

Ser Asp Ile Ala Arg Arg Gln Val Glu Ile Leu Asn Ala Gln Gln
            1160                1165                1170

Gln Ser Arg Asp Lys Glu Val Glu Ser Leu Arg Met Gln Leu Leu
            1175                1180                1185

Asp Tyr Gln Ala Gln Ser Asp Glu Lys Ser Leu Ile Ala Lys Leu
            1190                1195                1200

His Gln His Asn Val Ser Leu Gln Leu Ser Glu Ala Thr Ala Leu
            1205                1210                1215

Gly Lys Leu Glu Ser Ile Thr Ser Lys Leu Gln Lys Met Glu Ala

```
                1220              1225              1230

Tyr Asn Leu Arg Leu Glu Gln Lys Leu Asp Glu Lys Glu Gln Ala
    1235              1240              1245

Leu Tyr Tyr Ala Arg Leu Glu Gly Arg Asn Arg Ala Lys His Leu
    1250              1255              1260

Arg Gln Thr Ile Gln Ser Leu Arg Arg Gln Phe Ser Gly Ala Leu
    1265              1270              1275

Pro Leu Ala Gln Gln Glu Lys Phe Ser Lys Thr Met Ile Gln Leu
    1280              1285              1290

Gln Asn Asp Lys Leu Lys Ile Met Gln Glu Met Lys Asn Ser Gln
    1295              1300              1305

Gln Glu His Arg Asn Met Glu Asn Lys Thr Leu Glu Met Glu Leu
    1310              1315              1320

Lys Leu Lys Gly Leu Glu Glu Leu Ile Ser Thr Leu Lys Asp Thr
    1325              1330              1335

Lys Gly Ala Gln Lys Val Ile Asn Trp His Met Lys Ile Glu Glu
    1340              1345              1350

Leu Arg Leu Gln Glu Leu Lys Leu Asn Arg Glu Leu Val Lys Asp
    1355              1360              1365

Lys Glu Glu Ile Lys Tyr Leu Asn Asn Ile Ile Ser Glu Tyr Glu
    1370              1375              1380

Arg Thr Ile Ser Ser Leu Glu Glu Ile Val Gln Gln Asn Lys
    1385              1390              1395

Phe His Glu Glu Arg Gln Met Ala Trp Asp Gln Arg Glu Val Asp
    1400              1405              1410

Leu Glu Arg Gln Leu Asp Ile Phe Asp Arg Gln Gln Asn Glu Ile
    1415              1420              1425

Leu Asn Ala Ala Gln Lys Phe Glu Glu Ala Thr Gly Ser Ile Pro
    1430              1435              1440

Asp Pro Ser Leu Pro Leu Pro Asn Gln Leu Glu Ile Ala Leu Arg
    1445              1450              1455

Lys Ile Lys Glu Asn Ile Arg Ile Ile Leu Glu Thr Arg Ala Thr
    1460              1465              1470

Cys Lys Ser Leu Glu Glu Lys Leu Lys Glu Lys Glu Ser Ala Leu
    1475              1480              1485

Arg Leu Ala Glu Gln Asn Ile Leu Ser Arg Asp Lys Val Ile Asn
    1490              1495              1500

Glu Leu Arg Leu Arg Leu Pro Ala Thr Ala Glu Arg Glu Lys Leu
    1505              1510              1515

Ile Ala Glu Leu Gly Arg Lys Glu Met Glu Pro Lys Ser His His
    1520              1525              1530

Thr Leu Lys Ile Ala His Gln Thr Ile Ala Asn Met Gln Ala Arg
    1535              1540              1545

Leu Asn Gln Lys Glu Glu Val Leu Lys Lys Tyr Gln Arg Leu Leu
    1550              1555              1560

Glu Lys Ala Arg Glu Glu Gln Arg Glu Ile Val Lys Lys His Glu
    1565              1570              1575

Glu Asp Leu His Ile Leu His His Arg Leu Glu Leu Gln Ala Asp
    1580              1585              1590

Ser Ser Leu Asn Lys Phe Lys Gln Thr Ala Trp Asp Leu Met Lys
    1595              1600              1605

Gln Ser Pro Thr Pro Val Pro Thr Asn Lys His Phe Ile Arg Leu
    1610              1615              1620
```

```
Ala Glu Met Glu Gln Thr Val Ala Glu Gln Asp Asp Ser Leu Ser
        1625                1630            1635

Ser Leu Leu Val Lys Leu Lys Lys Val Ser Gln Asp Leu Glu Arg
        1640                1645            1650

Gln Arg Glu Ile Thr Glu Leu Lys Val Lys Glu Phe Glu Asn Ile
        1655                1660            1665

Lys Leu Gln Leu Gln Glu Asn His Glu Asp Glu Val Lys Lys Val
        1670                1675            1680

Lys Ala Glu Val Glu Asp Leu Lys Tyr Leu Leu Asp Gln Ser Gln
        1685                1690            1695

Lys Glu Ser Gln Cys Leu Lys Ser Glu Leu Gln Ala Gln Lys Glu
        1700                1705            1710

Ala Asn Ser Arg Ala Pro Thr Thr Thr Met Arg Asn Leu Val Glu
        1715                1720            1725

Arg Leu Lys Ser Gln Leu Ala Leu Lys Glu Lys Gln Gln Lys Ala
        1730                1735            1740

Leu Ser Arg Ala Leu Leu Glu Leu Arg Ala Glu Met Thr Ala Ala
        1745                1750            1755

Ala Glu Glu Arg Ile Ile Ser Ala Thr Ser Gln Lys Glu Ala His
        1760                1765            1770

Leu Asn Val Gln Gln Ile Val Asp Arg His Thr Arg Glu Leu Lys
        1775                1780            1785

Thr Gln Val Glu Asp Leu Asn Glu Asn Leu Leu Lys Leu Lys Glu
        1790                1795            1800

Ala Leu Lys Thr Ser Lys Asn Arg Glu Asn Ser Leu Thr Asp Asn
        1805                1810            1815

Leu Asn Asp Leu Asn Asn Glu Leu Gln Lys Lys Gln Lys Ala Tyr
        1820                1825            1830

Asn Lys Ile Leu Arg Glu Lys Glu Glu Ile Asp Gln Glu Asn Asp
        1835                1840            1845

Glu Leu Lys Arg Gln Ile Lys Arg Leu Thr Ser Gly Leu Gln Gly
        1850                1855            1860

Lys Pro Leu Thr Asp Asn Lys Gln Ser Leu Ile Glu Glu Leu Gln
        1865                1870            1875

Arg Lys Val Lys Lys Leu Glu Asn Gln Leu Glu Gly Lys Val Glu
        1880                1885            1890

Glu Val Asp Leu Lys Pro Met Lys Glu Lys Asn Ala Lys Glu Glu
        1895                1900            1905

Leu Ile Arg Trp Glu Glu Gly Lys Lys Trp Gln Ala Lys Ile Glu
        1910                1915            1920

Gly Ile Arg Asn Lys Leu Lys Glu Lys Glu Gly Glu Val Phe Thr
        1925                1930            1935

Leu Thr Lys Gln Leu Asn Thr Leu Lys Asp Leu Phe Ala Lys Ala
        1940                1945            1950

Asp Lys Glu Lys Leu Thr Leu Gln Arg Lys Leu Lys Thr Thr Gly
        1955                1960            1965

Met Thr Val Asp Gln Val Leu Gly Ile Arg Ala Leu Glu Ser Glu
        1970                1975            1980

Lys Glu Leu Glu Glu Leu Lys Lys Arg Asn Leu Asp Leu Glu Asn
        1985                1990            1995

Asp Ile Leu Tyr Met Arg Ala His Gln Ala Leu Pro Arg Asp Ser
        2000                2005            2010
```

Val Val Glu Asp Leu His Leu Gln Asn Arg Tyr Leu Gln Glu Lys
2015                2020                    2025

Leu His Ala Leu Glu Lys Gln Phe Ser Lys Asp Thr Tyr Ser Lys
2030                2035                    2040

Pro Ser Ile Ser Gly Ile Glu Ser Asp Asp His Cys Gln Arg Glu
2045                2050                    2055

Gln Glu Leu Gln Lys Glu Asn Leu Lys Leu Ser Ser Glu Asn Ile
2060                2065                    2070

Glu Leu Lys Phe Gln Leu Glu Gln Ala Asn Lys Asp Leu Pro Arg
2075                2080                    2085

Leu Lys Asn Gln Val Arg Asp Leu Lys Glu Met Cys Glu Phe Leu
2090                2095                    2100

Lys Lys Glu Lys Ala Glu Val Gln Arg Lys Leu Gly His Val Arg
2105                2110                    2115

Gly Ser Gly Arg Ser Gly Lys Thr Ile Pro Glu Leu Glu Lys Thr
2120                2125                    2130

Ile Gly Leu Met Lys Lys Val Val Glu Lys Val Gln Arg Glu Asn
2135                2140                    2145

Glu Gln Leu Lys Lys Ala Ser Gly Ile Leu Thr Ser Glu Lys Met
2150                2155                    2160

Ala Asn Ile Glu Gln Glu Asn Glu Lys Leu Lys Ala Glu Leu Glu
2165                2170                    2175

Lys Leu Lys Ala His Leu Gly His Gln Leu Ser Met His Tyr Glu
2180                2185                    2190

Ser Lys Thr Lys Gly Thr Glu Lys Ile Ile Ala Glu Asn Glu Arg
2195                2200                    2205

Leu Arg Lys Glu Leu Lys Lys Glu Thr Asp Ala Ala Glu Lys Leu
2210                2215                    2220

Arg Ile Ala Lys Asn Asn Leu Glu Ile Leu Asn Glu Lys Met Thr
2225                2230                    2235

Val Gln Leu Glu Glu Thr Gly Lys Arg Leu Gln Phe Ala Glu Ser
2240                2245                    2250

Arg Gly Pro Gln Leu Glu Gly Ala Asp Ser Lys Ser Trp Lys Ser
2255                2260                    2265

Ile Val Val Thr Arg Met Tyr Glu Thr Lys Leu Lys Glu Leu Glu
2270                2275                    2280

Thr Asp Ile Ala Lys Lys Asn Gln Ser Ile Thr Asp Leu Lys Gln
2285                2290                    2295

Leu Val Lys Glu Ala Thr Glu Arg Glu Gln Lys Val Asn Lys Tyr
2300                2305                    2310

Asn Glu Asp Leu Glu Gln Gln Ile Lys Ile Leu Lys His Val Pro
2315                2320                    2325

Glu Gly Ala Glu Thr Glu Gln Gly Leu Lys Arg Glu Leu Gln Val
2330                2335                    2340

Leu Arg Leu Ala Asn His Gln Leu Asp Lys Glu Lys Ala Glu Leu
2345                2350                    2355

Ile His Gln Ile Glu Ala Asn Lys Asp Gln Ser Gly Ala Glu Ser
2360                2365                    2370

Thr Ile Pro Asp Ala Asp Gln Leu Lys Glu Lys Ile Lys Asp Leu
2375                2380                    2385

Glu Thr Gln Leu Lys Met Ser Asp Leu Glu Lys Gln His Leu Lys
2390                2395                    2400

Glu Glu Ile Lys Lys Leu Lys Lys Glu Leu Glu Asn Phe Asp Pro

```
                 2405                2410                2415

Ser Phe Phe Glu Glu Ile Glu  Asp Leu Lys Tyr Asn  Tyr Lys Glu
    2420                2425                2430

Glu Val Lys Lys Asn Ile Leu  Leu Glu Glu Lys Val  Lys Lys Leu
    2435                2440                2445

Ser Glu Gln Leu Gly Val Glu  Leu Thr Ser Pro Val  Ala Ala Ser
    2450                2455                2460

Glu Glu Phe Glu Asp Glu Glu  Glu Ser Pro Val Asn  Phe Pro Ile
    2465                2470                2475

Tyr

<210> SEQ ID NO 4
<211> LENGTH: 128
<212> TYPE: DNA
<213> ORGANISM: Homo sapiens
<220> FEATURE:
<221> NAME/KEY: misc_feature
<222> LOCATION: (1)..(128)
<223> OTHER INFORMATION: 128 nucleotide aberrant CEO290 exon

<400> SEQUENCE: 4
tagagatggg gtttcacctt gttagccagg atggtgtcga tctcctgaac tcgtgatcca    60
cccgcctcgg cctcctaaag tgctgggatt acagatgtga gccaccgcac ctggccccag   120
ttgtaatt                                                             128

<210> SEQ ID NO 5
<211> LENGTH: 997
<212> TYPE: PRT
<213> ORGANISM: Homo sapiens
<220> FEATURE:
<221> NAME/KEY: misc_feature
<222> LOCATION: (1)..(997)
<223> OTHER INFORMATION: Aberrant CEP290 polypeptide

<400> SEQUENCE: 5

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
            85                  90                  95

Glu Leu Glu Met Ala Gln Gln Ser Ala Gly Gly Arg Asp Thr Arg Phe
        100                 105                 110

Leu Arg Asn Glu Ile Cys Gln Leu Glu Lys Gln Leu Glu Gln Lys Asp
    115                 120                 125

Arg Glu Leu Glu Asp Met Glu Lys Glu Leu Glu Lys Glu Lys Lys Val
    130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
            165                 170                 175
```

```
Cys Gln Asp Ile Ile Asp Tyr Gln Lys Gln Ile Asp Ser Gln Lys Glu
                180                 185                 190

Thr Leu Leu Ser Arg Arg Gly Glu Asp Ser Asp Tyr Arg Ser Gln Leu
            195                 200                 205

Ser Lys Lys Asn Tyr Glu Leu Ile Gln Tyr Leu Asp Glu Ile Gln Thr
        210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Lys Met Thr Asp Glu
                245                 250                 255

Tyr Asn Arg Met Lys Ala Ile Val His Gln Thr Asp Asn Val Ile Asp
            260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Asp Pro Ile Met Val
    290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
            340                 345                 350

Leu Gln Gln Gly Ile Gln Glu Arg Asp Ser Gln Ile Lys Met Leu Thr
        355                 360                 365

Glu Gln Val Glu Gln Tyr Thr Lys Glu Met Glu Lys Asn Thr Cys Ile
    370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
                405                 410                 415

Lys Glu Lys Thr Lys Glu Ala Glu Arg Thr Ala Glu Leu Ala Glu Ala
            420                 425                 430

Asp Ala Arg Glu Lys Asp Lys Glu Leu Val Glu Ala Leu Lys Arg Leu
        435                 440                 445

Lys Asp Tyr Glu Ser Gly Val Tyr Gly Leu Asp Ala Val Val Glu
    450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
                485                 490                 495

Leu Asp Glu Asn Glu Ala Leu Arg Glu Arg Val Gly Leu Glu Pro Lys
            500                 505                 510

Thr Met Ile Asp Leu Thr Glu Phe Arg Asn Ser Lys His Leu Lys Gln
        515                 520                 525

Gln Gln Tyr Arg Ala Glu Asn Gln Ile Leu Leu Lys Glu Ile Glu Ser
    530                 535                 540

Leu Glu Glu Glu Arg Leu Asp Leu Lys Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
            580                 585                 590

Lys Leu Asp Leu Leu Ser Leu Lys Asn Met Ser Glu Ala Gln Ser Lys
```

595					600					605
Asn Glu Phe Leu Ser Arg Glu Leu Ile Glu Lys Glu Arg Asp Leu Glu
			610					615					620
Arg Ser Arg Thr Val Ile Ala Lys Phe Gln Asn Lys Leu Lys Glu Leu
625					630					635					640
Val Glu Glu Asn Lys Gln Leu Glu Glu Gly Met Lys Glu Ile Leu Gln
				645					650					655
Ala Ile Lys Glu Met Gln Lys Asp Pro Asp Val Lys Gly Gly Glu Thr
				660					665					670
Ser Leu Ile Ile Pro Ser Leu Glu Arg Leu Val Asn Ala Ile Glu Ser
				675					680					685
Lys Asn Ala Glu Gly Ile Phe Asp Ala Ser Leu His Leu Lys Ala Gln
				690					695					700
Val Asp Gln Leu Thr Gly Arg Asn Glu Glu Leu Arg Gln Glu Leu Arg
705					710					715					720
Glu Ser Arg Lys Glu Ala Ile Asn Tyr Ser Gln Gln Leu Ala Lys Ala
				725					730					735
Asn Leu Lys Ile Asp His Leu Glu Lys Glu Thr Ser Leu Leu Arg Gln
				740					745					750
Ser Glu Gly Ser Asn Val Val Phe Lys Gly Ile Asp Leu Pro Asp Gly
				755					760					765
Ile Ala Pro Ser Ser Ala Ser Ile Ile Asn Ser Gln Asn Glu Tyr Leu
				770					775					780
Ile His Leu Leu Gln Glu Leu Glu Asn Lys Glu Lys Lys Leu Lys Asn
785					790					795					800
Leu Glu Asp Ser Leu Glu Asp Tyr Asn Arg Lys Phe Ala Val Ile Arg
				805					810					815
His Gln Gln Ser Leu Leu Tyr Lys Glu Tyr Leu Ser Glu Lys Glu Thr
				820					825					830
Trp Lys Thr Glu Ser Lys Thr Ile Lys Glu Glu Lys Arg Lys Leu Glu
				835					840					845
Asp Gln Val Gln Gln Asp Ala Ile Lys Val Lys Glu Tyr Asn Asn Leu
				850					855					860
Leu Asn Ala Leu Gln Met Asp Ser Asp Glu Met Lys Lys Ile Leu Ala
865					870					875					880
Glu Asn Ser Arg Lys Ile Thr Val Leu Gln Val Asn Glu Lys Ser Leu
				885					890					895
Ile Arg Gln Tyr Thr Thr Leu Val Glu Leu Glu Arg Gln Leu Arg Lys
				900					905					910
Glu Asn Glu Lys Gln Lys Asn Glu Leu Leu Ser Met Glu Ala Glu Val
				915					920					925
Cys Glu Lys Ile Gly Cys Leu Gln Arg Phe Lys Glu Met Ala Ile Phe
				930					935					940
Lys Ile Ala Ala Leu Gln Lys Val Val Asp Asn Ser Val Ser Leu Ser
945					950					955					960
Glu Leu Glu Leu Ala Asn Lys Gln Tyr Asn Glu Leu Thr Ala Lys Tyr
				965					970					975
Arg Asp Ile Leu Gln Lys Asp Asn Met Leu Val Gln Arg Thr Ser Asn
				980					985					990
Leu Glu His Leu Glu
		995

<210> SEQ ID NO 6

```
<211> LENGTH: 143
<212> TYPE: DNA
<213> ORGANISM: Homo sapiens
<220> FEATURE:
<221> NAME/KEY: misc_feature
<222> LOCATION: (1)..(143)
<223> OTHER INFORMATION: 143 nucleotide motif

<400> SEQUENCE: 6
tagagatggg gtttcacctt gttagccagg atggtgtcga tctcctgaac tcgtgatcca      60
cccgcctcgg cctcctaaag tgctgggatt acagatgtga gccaccgcac ctggcccag     120 ttgtaattgt gaatatctca tac                                            143

<210> SEQ ID NO 7
<211> LENGTH: 42
<212> TYPE: DNA
<213> ORGANISM: Homo sapiens
<220> FEATURE:
<221> NAME/KEY: misc_feature
<222> LOCATION: (1)..(42)
<223> OTHER INFORMATION: 42 nucleotide motif

<400> SEQUENCE: 7
acagatgtga gccaccgcac ctggccccag ttgtaattgt ga                         42

<210> SEQ ID NO 8
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: 24 nucleotide motif

<400> SEQUENCE: 8
ccaccgcacc tggccccagt tgta                                             24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-1

<400> SEQUENCE: 9
taatcccagc actttaggag                                                  20

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-2

<400> SEQUENCE: 10
gggccaggtg cggtgg                                                      16

<210> SEQ ID NO 11
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: AON-3

<400> SEQUENCE: 11
aactggggcc aggtgcg                                                    17

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-4

<400> SEQUENCE: 12
tacaactggg gccaggtg                                                   18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-5

<400> SEQUENCE: 13
actcacaatt acaactgggg                                                 20

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SON-3

<400> SEQUENCE: 14
cgcacctggc cccagtt                                                    17

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 15
tgctaagtac agggacatct tgc                                             23

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 16
```

```
agactccact tgttcttta aggag                                                25

<210> SEQ ID NO 17
<211> LENGTH: 36
<212> TYPE: DNA
<213> ORGANISM: Homo sapiens

<400> SEQUENCE: 17
cacctggccc cagttgtaat tgtgaatatc tcatac                                   36

<210> SEQ ID NO 18
<211> LENGTH: 36
<212> TYPE: RNA
<213> ORGANISM: Homo sapiens

<400> SEQUENCE: 18
caccuggccc caguuguaau ugugaauauc ucauac                                   36

<210> SEQ ID NO 19
<211> LENGTH: 36
<212> TYPE: DNA
<213> ORGANISM: Homo sapiens

<400> SEQUENCE: 19
cacctggccc cagttgtaat tgtgagtatc tcatac                                   36

<210> SEQ ID NO 20
<211> LENGTH: 36
<212> TYPE: RNA
<213> ORGANISM: Homo sapiens

<400> SEQUENCE: 20
caccuggccc caguuguaau ugugaguauc ucauac                                   36

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
auacuacuaa uuacaacugg g                                                   21
```

ANTISENSE OLIGONUCLEOTIDES FOR THE TREATMENT OF LEBER CONGENITAL AMAUROSIS

CROSS-REFERENCE TO RELATED APPLICATIONS

The present application is a U.S. National Phase of International Patent Application No. PCT/NL2012/050275, filed Apr. 25, 2012, which claims priority from Netherlands Patent Application No. 2007351, filed Sep. 5, 2011, and U.S. Provisional Application No. 61/531,137, filed Sep. 6, 2011. The contents of these applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Jul. 11, 2014, is named 069818-9675_SL.txt and is 234,443 bytes in size.

FIELD OF THE INVENTION

The present invention relates to the fields of medicine and immunology. In particular, it relates to novel antisense oligonucleotides that may be used in the treatment, prevention and/or delay of Leber congenital amaurosis.

BACKGROUND OF THE INVENTION

Leber congenital amaurosis (LCA) is the most severe form of inherited retinal dystrophy, with an onset of disease symptoms in the first years of life (Leber, T., 1869) and an estimated prevalence of approximately 1 in 50,000 worldwide (Koenekoop et al, 2007; Stone, 2007). Genetically, LCA is a heterogeneous disease, with fifteen genes identified to date in which mutations are causative for LCA (den Hollander et al, 2008; Estrada-Cuzcano et al, 2011). The most frequently mutated LCA gene is CEP290, accounting for ~15% of all cases (Stone, 2007; den Hollander, 2008; den Hollander, 2006; Perrault et al, 2007). Severe mutations in CEP290 have been reported to cause a spectrum of systemic diseases that, besides retinal dystrophy, are characterized by brain defects, kidney malformations, polydactyly and/or obesity (Baal et al, 2007; den Hollander et al, 2008; Helou et al, 2007; Valente et al, 2006). There is no clear-cut genotype-phenotype correlation between the combination of CEP290 mutations and the associated phenotypes, but patients with LCA and early-onset retinal dystrophy very often carry hypomorphic alleles (Stone, 2007; den Hollander et al, 2006; Perrault et al, 2007; Coppieters et al, 2010; Liitink et al 2010). The by far most frequently occurring hypomorphic CEP290 mutation, especially in European countries and in the US, is a change in intron 26 of CEP290 (c.2991+1655A>G) (Stone, 2007; den Hollander et al, 2006; Perrault et al, 2007; Liitink et al, 2010). This mutation creates a cryptic splice donor site in intron 26 which results in the inclusion of an aberrant exon of 128 bp in the mutant CEP290 mRNA, and inserts a premature stop codon (p.C998X) (see FIGS. 1A and 1B). Besides the mutant CEP290 mRNA, also the wild-type transcript that lacks the aberrant exon is still produced, explaining the hypomorphic nature of this mutation (Estrada-Cuzcano et al, 2011).

LCA, and other retinal dystrophies, for long have been considered incurable diseases. However, the first phase I/II clinical trials using gene augmentation therapy have lead to promising results in a selected group of adult LCA/RP patients with mutations in the RPE65 gene (Bainbridge et al, 2008; Cideciyan et al, 2008; Hauswirth et al, 2008; Maguire et al, 2008). Unilateral subretinal injections of adeno-associated viruses particles carrying constructs encoding the wild-type RPE65 cDNA were shown to be safe and moderately effective in some patients, without causing any adverse effects. In a follow-up study using adults and children, visual improvements were more sustained, especially in the children who all gained ambulatory vision (Maguire et al, 2009). Together, these studies have shown the potential to treat LCA, and thereby enormously boosted the development of therapeutic strategies for other genetic subtypes of retinal dystrophies (den Hollander et al, 2010). However, due to the tremendous variety in gene size, and technical limitations of the vehicles that are used to deliver therapeutic constructs, gene augmentation therapy may not be applicable to all genes. The RPE65 cDNA is for instance only 1.6 kb, whereas the CEP290 cDNA amounts to about 7.4 kb, thereby exceeding the cargo size of many available vectors, including the presently used adeno-associated vectors (AAV). In addition, using gene replacement therapy, it is hard to control the expression levels of the therapeutic gene which for some genes need to be tightly regulated. It is therefore an objective of the present invention to provide a convenient therapeutic strategy for the prevention, treatment or delay of Leber congenital amaurosis as caused by an intronic mutation in CEP290.

DETAILED DESCRIPTION OF THE INVENTION

Surprisingly, it has now been demonstrated that specific antisense oligonucleotides (AONs) are able to block the aberrant splicing of CEP290 that is caused by the intronic LCA mutation.

Accordingly, in a first aspect the present invention provides an exon skipping molecule that binds to and/or is complementary to a polynucleotide with the nucleotide sequence as shown in SEQ ID NO: 6, preferably SEQ ID NO: 7, more preferably SEQ ID NO: 8, or a part thereof.

In all embodiments of the present invention, the terms "modulating splicing" and "exon skipping" are synonymous. In respect of CEP290, "modulating splicing" or "exon skipping" are to be construed as the exclusion of the aberrant 128 nucleotide exon (SEQ ID NO: 4) from the CEP290 mRNA (see FIGS. 1A and 1B). The term exon skipping is herein defined as the induction within a cell of a mature mRNA that does not contain a particular exon that would be present in the mature mRNA without exon skipping. Exon skipping is achieved by providing a cell expressing the pre-mRNA of said mature mRNA with a molecule capable of interfering with sequences such as, for example, the (cryptic) splice donor or (cryptic) splice acceptor sequence required for allowing the enzymatic process of splicing, or with a molecule that is capable of interfering with an exon inclusion signal required for recognition of a stretch of nucleotides as an exon to be included in the mature mRNA; such molecules are herein referred to as exon skipping molecules The term pre-mRNA refers to a non-processed or partly processed precursor mRNA that is synthesized from a DNA template in the nucleus of a cell by transcription.

The term "antisense oligonucleotide" is understood to refer to a nucleotide sequence which is substantially complementary to a target nucleotide sequence in a pre-mRNA molecule, hrRNA (heterogenous nuclear RNA) or mRNA molecule. The degree of complementarity (or substantial complementarity) of the antisense sequence is preferably such that a molecule comprising the antisense sequence can form a stable hybrid with the target nucleotide sequence in the RNA molecule under physiological conditions.

The terms "antisense oligonucleotide" and "oligonucleotide" are used interchangeably herein and are understood to refer to an oligonucleotide comprising an antisense sequence.

In an embodiment, an exon skipping molecule as defined herein can be a compound molecule that binds and/or is complementary to the specified sequence, or a protein such as an RNA-binding protein or a non-natural zinc-finger protein that has been modified to be able to bind to the indicated nucleotide sequence on a RNA molecule. Methods for screening compound molecules that bind specific nucleotide sequences are, for example, disclosed in PCT/NL01/00697 and U.S. Pat. No. 6,875,736, which are herein incorporated by reference. Methods for designing RNA-binding Zinc-finger proteins that bind specific nucleotide sequences are disclosed by Friesen and Darby, Nature Structural Biology 5: 543-546 (1998) which is herein incorporated by reference. Binding to one of the specified SEQ ID NO: 6, 7 or 8 sequence, preferably in the context of the aberrant 128 nucleotide CEP290 exon (SEQ ID NO: 4) may be assessed via techniques known to the skilled person. A preferred technique is gel mobility shift assay as described in EP 1 619 249. In a preferred embodiment, an exon skipping molecule is said to bind to one of the specified sequences as soon as a binding of said molecule to a labeled sequence SEQ ID NO: 6, 7 or 8 is detectable in a gel mobility shift assay.

In all embodiments of the invention, an exon skipping molecule is preferably a nucleic acid molecule, preferably an oligonucleotide. Preferably, an exon skipping molecule according to the invention is a nucleic acid molecule, preferably an oligonucleotide, which is complementary or substantially complementary to a nucleotide sequence as shown in SEQ ID NO: 6, preferably SEQ ID NO: 7, more preferably SEQ ID NO: 8, or a part thereof as later defined herein.

The term "substantially complementary" used in the context of the present invention indicates that some mismatches in the antisense sequence are allowed as long as the functionality, i.e. inducing skipping of the aberrant 128 nucleotide CEP290 exon (SEQ ID NO: 4), is still acceptable. Preferably, the complementarity is from 90% to 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc.

The present invention provides a method for designing an exon skipping molecule, preferably an oligonucleotide able to induce skipping of the aberrant 128 nucleotide CEP290 exon (SEQ ID NO: 4). First, said oligonucleotide is selected to bind to one of SEQ ID NO: 6, 7 or 8 or a part thereof as defined later herein. Subsequently, in a preferred method at least one of the following aspects has to be taken into account for designing, improving said exon skipping molecule any further:

The exon skipping molecule preferably does not contain a CpG or a stretch of CpG, The exon skipping molecule has acceptable RNA binding kinetics and/or thermodynamic properties.

The presence of a CpG or a stretch of CpG in an oligonucleotide is usually associated with an increased immunogenicity of said oligonucleotide (Dorn and Kippenberger, 2008). This increased immunogenicity is undesired since it may induce damage of the tissue to be treated, i.e. the eye. Immunogenicity may be assessed in an animal model by assessing the presence of CD4+ and/or CD8+ cells and/or inflammatory mononucleocyte infiltration. Immunogenicity may also be assessed in blood of an animal or of a human being treated with an oligonucleotide of the invention by detecting the presence of a neutralizing antibody and/or an antibody recognizing said oligonucleotide using a standard immunoassay known to the skilled person.

An increase in immunogenicity may be assessed by detecting the presence or an increasing amount of a neutralizing antibody or an antibody recognizing said oligonucleotide using a standard immunoassay.

The invention allows designing an oligonucleotide with acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (www.unc.edu/~cail/biotool/oligo/index.html) for single stranded RNA using the basic Tm and the nearest neighbor model), and/or the free energy of the AON-target exon complex (using RNA structure version 4.5). If a Tm is too high, the oligonucleotide is expected to be less specific. An acceptable Tm and free energy depend on the sequence of the oligonucleotide. Therefore, it is difficult to give preferred ranges for each of these parameters. An acceptable Tm may be ranged between 35 and 70° C. and an acceptable free energy may be ranged between 15 and 45 kcal/mol.

The skilled person may therefore first choose an oligonucleotide as a potential therapeutic compound as binding and/or being complementary to SEQ ID NO: 6, 7, or 8 or a part thereof as defined later herein. The skilled person may check that said oligonucleotide is able to bind to said sequences as earlier defined herein. Optionally in a second step, he may use the invention to further optimize said oligonucleotide by checking for the absence of CpG and/or by optimizing its Tm and/or free energy of the AON-target complex. He may try to design an oligonucleotide wherein preferably no CpG and/or wherein a more acceptable Tm and/or free energy are obtained by choosing a distinct sequence of CEP290 (including SEQ ID NO: 6, 7 or 8) to which the oligonucleotide is complementary. Alternatively, if an oligonucleotide complementary to a given stretch within SEQ ID NO: 6, 7 or 8, comprises a CpG, and/or does not have an acceptable Tm and/or free energy, the skilled person may improve any of these parameters by decreasing the length of the oligonucleotide, and/or by choosing a distinct stretch within any of SEQ ID NO: 6, 7 or 8 to which the oligonucleotide is complementary and/or by altering the chemistry of the oligonucleotide.

At any step of the method, an oligonucleotide of the invention is preferably an olignucleotide, which is still able to exhibit an acceptable level of functional activity. A functional activity of said oligonucleotide is preferably to induce the skipping of the aberrant 128 nucleotide CEP290 exon (SEQ ID NO: 4) to a certain extent, to provide an individual with a functional CEP290 protein and/or mRNA and/or at least in part decreasing the production of an aberrant CEP290 protein and/or mRNA. In a preferred embodiment, an oligonucleotide is said to induce skipping of the aberrant 128 nucleotide CEP290 exon (SEQ ID NO: 4), when the aberrant 128 nucleotide CEP290 exon (SEQ ID NO: 4) skipping percentage as measured by real-time quantitative RT-PCR analysis (is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%.

Preferably, a nucleic acid molecule according to the invention, preferably an oligonucleotide, which comprises a sequence that is complementary or substantially complementary to a nucleotide sequence as shown in SEQ ID NO: 6, preferably SEQ ID NO: 7, more preferably SEQ ID NO: 8, or part thereof of CEP290 is such that the (substantially) complementary part is at least 50% of the length of the oligonucleotide according to the invention, more preferably at least 60%, even more preferably at least 70%, even more preferably at least 80%, even more preferably at least 90% or even more preferably at least 95%, or even more preferably 98% or even more preferably at least 99%, or even more preferably 100%. Preferably, an oligonucleotide according to the invention comprises or consists of a sequence that is complementary to part of SEQ ID NO: 6, 7 or 8. As an example, an oligonucleotide may comprise a sequence that is complementary to part of SEQ ID NO: 6, 7 or 8 and additional flanking sequences. In a more preferred embodiment, the length of said complementary part of said oligonucleotide is of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides. Additional flanking sequences may be used to modify the binding of a protein to the oligonucleotide, or to modify a thermodynamic property of the oligonucleotide, more preferably to modify target RNA binding affinity.

It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may, to some extent, be allowed, if under the circumstances in the cell, the stretch of nucleotides is sufficiently capable of hybridizing to the complementary part. In this context, "sufficiently" preferably means that using a gel mobility shift assay as described in example 1 of EP1619249, binding of an oligonucleotide is detectable. Optionally, said oligonucleotide may further be tested by transfection into retina cells of patients. Skipping of a targeted exon may be assessed by RT-PCR (as described in EP1619249). The complementary regions are preferably designed such that, when combined, they are specific for the exon in the pre-mRNA. Such specificity may be created with various lengths of complementary regions as this depends on the actual sequences in other (pre-)mRNA molecules in the system. The risk that the oligonucleotide also will be able to hybridize to one or more other pre-mRNA molecules decreases with increasing size of the oligonucleotide. It is clear that oligonucleotides comprising mismatches in the region of complementarity but that retain the capacity to hybridize and/or bind to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought, that higher hybridization strengths, (i.e. increasing number of interactions with the opposing strand) are favorable in increasing the efficiency of the process of interfering with the splicing machinery of the system. Preferably, the complementarity is from 90% to 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc.

An exon skipping molecule of the invention is preferably an isolated molecule.

An exon skipping molecule of the invention is preferably a nucleic acid molecule or nucleotide-based molecule, preferably an (antisense) oligonucleotide, which is complementary to a sequence selected from SEQ ID NO: 6, 7 and 8.

A preferred exon skipping molecule, according to the invention is a nucleic acid molecule comprising an antisense oligonucleotide which antisense oligonucleotide has a length from about 8 to about 143 nucleotides, more preferred from about 8 to 60, more preferred 10 to about 40 nucleotides, more preferred from about 12 to about 30 nucleotides, more preferred from about 14 to about 28 nucleotides, nucleotides, most preferred about 20 nucleotides, such as 15 nucleotides, 16 nucleotides, 17 nucleotides, 18 nucleotides, 19 nucleotides, 20 nucleotides, 21 nucleotides, 22 nucleotides, 23 nucleotides, 24 nucleotides or 25 nucleotides.

A preferred exon skipping molecule of the invention is an antisense oligonucleotide comprising or consisting of from 8 to 143 nucleotides, more preferred from 10 to 40 nucleotides, more preferred from 12 to 30 nucleotides, more preferred from 14 to 20 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In certain embodiments, the invention provides an exon skipping molecule comprising or preferably consisting of an antisense oligonucleotide selected from the group consisting of: SEQ ID NO: 10, SEQ ID NO: 11, and SEQ ID NO: 12.

In a more preferred embodiment, the invention provides an exon skipping molecule comprising or preferably consisting of the antisense oligonucleotide SEQ ID NO: 10. It was found that this molecule is very efficient in modulating splicing of the aberrant 128 nucleotide CEP290 exon. This preferred exon skipping molecule of the invention comprising SEQ ID NO: 10 preferably comprises from 8 to 143 nucleotides, more preferred from 10 to 40 nucleotides, more preferred from 10 to 30 nucleotides, more preferred from 12 to 20 nucleotides, more preferably from 14 to 18 or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In another more preferred embodiment, the invention provides an exon skipping molecule comprising or preferably consisting of the antisense oligonucleotide SEQ ID NO: 11. It was found that this molecule is very efficient in modulating splicing of the aberrant 128 nucleotide CEP290 exon. This preferred exon skipping molecule of the invention comprising SEQ ID NO: 11 preferably comprises from 8 to 143 nucleotides, more preferred from 10 to 40 nucleotides, more preferred from 10 to 30 nucleotides, more preferred from 12 to 20 nucleotides, more preferably from 14 to 18, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In another more preferred embodiment, the invention provides an exon skipping molecule comprising or preferably consisting of the antisense oligonucleotide SEQ ID NO: 12. It was found that this molecule is very efficient in modulating splicing of the aberrant 128 nucleotide CEP290 exon. This preferred exon skipping molecule of the invention comprising SEQ ID NO: 12 preferably comprises from 8 to 143 nucleotides, more preferred from 10 to 40 nucleotides, more preferred from 10 to 30 nucleotides, more preferred from 12 to 20 nucleotides, more preferably from 14 to 18, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

An exon skipping molecule according to the invention may contain one of more RNA residues, or one or more DNA residues, and/or one or more nucleotide analogues or equivalents, as will be further detailed herein below.

It is preferred that an exon skipping molecule of the invention comprises one or more residues that are modified to increase nuclease resistance, and/or to increase the affinity of the antisense oligonucleotide for the target sequence. Therefore, in a preferred embodiment, the antisense nucleotide sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium.

It is further preferred that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; dimethylaminooxyethoxy; and -dimethylaminoethoxyethoxy. The sugar moiety can be a pyranose or derivative thereof, or a deoxypyranose or derivative thereof, preferably ribose or derivative thereof, or deoxyribose or derivative of. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-0,4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

A preferred exon skipping molecule according to the invention comprises a 2'-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives.

An effective antisense oligonucleotide according to the invention comprises a 2'-O-methyl ribose with a phosphorothioate backbone.

It will also be understood by a skilled person that different antisense oligonucleotides can be combined for efficiently skipping of the aberrant 128 nucleotide exon of CEP290. In a preferred embodiment, a combination of at least two antisense oligonucleotides are used in a method of the invention, such as two different antisense oligonucleotides, three different antisense oligonucleotides, four different antisense oligonucleotides, or five different antisense oligonucleotides.

An antisense oligonucleotide can be linked to a moiety that enhances uptake of the antisense oligonucleotide in cells, preferably retina cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

An exon skipping molecule according to the invention may be indirectly administrated using suitable means known in the art. When the exon skipping molecule is an oligonucleotide, it may for example be provided to an individual or a cell, tissue or organ of said individual in the form of an expression vector wherein the expression vector encodes a transcript comprising said oligonucleotide. The expression vector is preferably introduced into a cell, tissue, organ or individual via a gene delivery vehicle. In a preferred embodiment, there is provided a viral-based expression vector comprising an expression cassette or a transcription cassette that drives expression or transcription of an exon skipping molecule as identified herein. Accordingly, the present invention provides a viral vector expressing an exon skipping molecule according to the invention when placed under conditions conducive to expression of the exon skipping molecule. A cell can be provided with an exon skipping molecule capable of interfering with essential sequences that result in highly efficient skipping of the aberrant 128 nucleotide CEP290 exon by plasmid-derived antisense oligonucleotide expression or viral expression provided by adenovirus- or adeno-associated virus-based vectors. Expression may be driven by a polymerase III promoter, such as a U1, a U6, or a U7 RNA promoter. A preferred delivery vehicle is a viral vector such as an adeno-associated virus vector (AAV), or a retroviral vector such as a lentivirus vector and the like. Also, plasmids, artificial chromosomes, plasmids usable for targeted homologous recombination and integration in the human genome of cells may be suitably applied for delivery of an oligonucleotide as defined herein. Preferred for the current invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts. Preferably, in the form of a fusion transcript with an U1 or U7 transcript. Such fusions may be generated as described (Gorman L et al, 1998 or Suter D et al, 1999).

The exon skipping molecule according to the invention, preferably an antisense oligonucleotide, may be delivered as such. However, the exon skipping molecule may also be encoded by the viral vector. Typically, this is in the form of an RNA transcript that comprises the sequence of an oligonucleotide according to the invention in a part of the transcript.

One preferred antisense oligonucleotide expression system is an adenovirus associated virus (AAV)-based vector. Single chain and double chain AAV-based vectors have been developed that can be used for prolonged expression of small antisense nucleotide sequences for highly efficient skipping of the aberrant 128 nucleotide CEP290 exon.

A preferred AAV-based vector for instance comprises an expression cassette that is driven by a polymerase III-promoter (Pol III). A preferred Pol III promoter is, for example, a U1, a U6, or a U7 RNA promoter.

The invention therefore also provides a viral-based vector, comprising a Pol III-promoter driven expression cassette for expression of an antisense oligonucleotide of the invention for inducing skipping of aberrant 128 nucleotide CEP290 exon.

Improvements in means for providing an individual or a cell, tissue, organ of said individual with an exon skipping molecule according to the invention, are anticipated considering the progress that has already thus far been achieved. Such future improvements may of course be incorporated to achieve the mentioned effect on restructuring of mRNA using a method of the invention. An exon skipping molecule according to the invention can be delivered as is to an individual, a cell, tissue or organ of said individual. When administering an exon skipping molecule according to the invention, it is preferred that the molecule is dissolved in a solution that is compatible with the delivery method. Retina cells can be provided with a plasmid for antisense oligonucleotide expression by providing the plasmid in an aqueous solution. Alternatively, a plasmid can be provided by transfection using known transfection agentia. For intravenous, subcutaneous, intramuscular, intrathecal and/or intraventricular administration it is preferred that the solution is a physiological salt solution. Particularly preferred in the invention is the use of an excipient or transfection agentia that will aid in delivery of each of the constituents as defined herein to a cell and/or into a cell, preferably a retina cell. Preferred are excipients or transfection agentia capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection agentia comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self assembly into particles that can deliver each constituent as defined herein to a cell, preferably a retina cell. Such excipients have been shown to efficiently deliver an oligonucleotide such as antisense nucleic acids to a wide variety of cultured cells, including retina cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide, across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an exon skipping molecule for use in the current invention to deliver it for the prevention, treatment or delay of a CEP290 related disease or condition. "Prevention, treatment or delay of a CEP290 related disease or condition" is herein preferably defined as preventing, halting, ceasing the progression of, or reversing partial or complete visual impairment or blindness that is caused by a genetic defect in the CEP290 gene.

In addition, an exon skipping molecule according to the invention could be covalently or non-covalently linked to a targeting ligand specifically designed to facilitate the uptake into the cell, cytoplasm and/or its nucleus. Such ligand could comprise (i) a compound (including but not limited to peptide(-like) structures) recognising cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an exon skipping molecule according to the invention is formulated in a composition or a medicament or a composition, which is provided with at least an excipient and/or a targeting ligand for delivery and/or a delivery device thereof to a cell and/or enhancing its intracellular delivery.

It is to be understood that if a composition comprises an additional constituent such as an adjunct compound as later defined herein, each constituent of the composition may not be formulated in one single combination or composition or preparation. Depending on their identity, the skilled person will know which type of formulation is the most appropriate for each constituent as defined herein. In a preferred embodiment, the invention provides a composition or a preparation which is in the form of a kit of parts comprising an exon skipping molecule according to the invention and a further adjunct compound as later defined herein.

If required, an exon skipping molecule according to the invention or a vector, preferably a viral vector, expressing an exon skipping molecule according to the invention can be incorporated into a pharmaceutically active mixture by adding a pharmaceutically acceptable carrier.

Accordingly, the invention also provides a composition, preferably a pharmaceutical composition, comprising an exon skipping molecule according to the invention, or a viral vector according to the invention and a pharmaceutically acceptable excipient. Such composition may comprise a single exon skipping molecule according to the invention, but may also comprise multiple, distinct exon skipping molecules according to the invention. Such a pharmaceutical composition may comprise any pharmaceutically acceptable excipient, including a carrier, filler, preservative, adjuvant, solubilizer and/or diluent. Such pharmaceutically acceptable carrier, filler, preservative, adjuvant, solubilizer and/or diluent may for instance be found in Remington, 2000. Each feature of said composition has earlier been defined herein.

If multiple distinct exon skipping molecules according to the invention are used, concentration or dose defined herein may refer to the total concentration or dose of all oligonucleotides used or the concentration or dose of each exon skipping molecule used or added. Therefore in one embodiment, there is provided a composition wherein each or the total amount of exon skipping molecules according to the invention used is dosed in an amount ranged from 0.1 and 20 mg/kg, preferably from 0.5 and 20 mg/kg.

A preferred exon skipping molecule according to the invention, is for the treatment of a CEP290 related disease or condition of an individual. In all embodiments of the present invention, the term "treatment" is understood to include the prevention and/or delay of the CEP290 related disease or condition. An individual, which may be treated using an exon skipping molecule according to the invention may already have been diagnosed as having a CEP290 related disease or condition. Alternatively, an individual which may be treated using an exon skipping molecule according to the invention may not have yet been diagnosed as having a CEP290 related disease or condition but may be an individual having an increased risk of developing a CEP290 related disease or condition in the future given his or her genetic background. A preferred individual is a human being. In a preferred embodiment the CEP290 related disease or condition is Leber congenital amaurosis.

Accordingly, the present invention further provides an exon skipping molecule according to the invention, or a viral vector according to the invention, or a composition according to the invention for use as a medicament, for treating a CEP290 related disease or condition requiring modulating splicing of CEP290 and for use as a medicament for the prevention, treatment or delay of a CEP290 related disease or condition. A preferred CEP290 related disease or condition is Leber congenital amaurosis. Each feature of said use has earlier been defined herein.

The invention further provides the use of an exon skipping molecule according to the invention, or of a viral vector according to the invention, or a composition according to the invention for the treatment of a CEP290 related disease or condition requiring modulating splicing of CEP290. In a preferred embodiment the CEP290 related disease or condition is Leber congenital amaurosis.

The present invention further provides the use of an exon skipping molecule according to the invention, or of a viral vector according to the invention, or a composition according to the invention for the preparation of a medicament, for the preparation of a medicament for treating a CEP290 related disease or condition requiring modulating splicing of CEP290 and for the preparation of a medicament for the prevention, treatment or delay of a CEP290 related disease or condition. A preferred CEP290 related disease or condition is Leber congenital amaurosis. Therefore in a further aspect, there is provided the use of an exon skipping molecule, viral vector or composition as defined herein for the preparation of a medicament, for the preparation of a medicament for treating a condition requiring modulating splicing of CEP290 and for the preparation of a medicament for the prevention, treatment or delay of a CEP290 related disease or condition. A preferred CEP290 related disease or condition is Leber congenital amaurosis. Each feature of said use has earlier been defined herein.

A treatment in a use or in a method according to the invention is at least one week, at least one month, at least several months, at least one year, at least 2, 3, 4, 5, 6 years or more. Each exon skipping molecule or exon skipping oligonucleotide or equivalent thereof as defined herein for use according to the invention may be suitable for direct administration to a cell, tissue and/or an organ in vivo of individuals already affected or at risk of developing CEP290 related disease or condition, and may be administered directly in vivo, ex vivo or in vitro. The frequency of administration of an oligonucleotide, composition, compound or adjunct compound of the invention may depend on several parameters such as the age of the patient, the mutation of the patient, the number of exon skipping molecules (i.e. dose), the formulation of said molecule. The frequency may be ranged between at least once in two weeks, or three weeks or four weeks or five weeks or a longer time period.

Dose ranges of an exon skipping molecule, preferably an oligonucleotide according to the invention are preferably designed on the basis of rising dose studies in clinical trials (in vivo use) for which rigorous protocol requirements exist. An exon skipping molecule or an oligonucleotide as defined herein may be used at a dose which is ranged from 0.1 and 20 mg/kg, preferably from 0.5 and 20 mg/kg.

In a preferred embodiment, a concentration of an oligonucleotide as defined herein, which is ranged from 0.1 nM and 1 µM is used. Preferably, this range is for in vitro use in a cellular model such as retina cells or retinal tissue. More preferably, the concentration used is ranged from 1 to 400 nM, even more preferably from 10 to 200 nM, even more preferably from 50 to 100 nm. If several oligonucleotides are used, this concentration or dose may refer to the total concentration or dose of oligonucleotides or the concentration or dose of each oligonucleotide added.

In a preferred embodiment, a viral vector, preferably an AAV vector as described earlier herein, as delivery vehicle for a molecule according to the invention, is administered in a dose ranging from $1\times10^9$-$1\times10^{17}$ virusparticles per injection, more preferably from $1\times10^{10}$-$1\times10^{12}$ virusparticles per injection.

The ranges of concentration or dose of oligonucleotide(s) as given above are preferred concentrations or doses for in vitro or ex vivo uses. The skilled person will understand that depending on the oligonucleotide(s) used, the target cell to be treated, the gene target and its expression levels, the medium used and the transfection and incubation conditions, the concentration or dose of oligonucleotide(s) used may further vary and may need to be optimized any further.

An exon skipping molecule according to the invention, or a viral vector according to the invention, or a composition according to the invention for use according to the invention may be suitable for administration to a cell, tissue and/or an organ in vivo of individuals already affected or at risk of developing a CEP290 related disease or condition, and may be administered in vivo, ex vivo or in vitro. Said exon skipping molecule according to the invention, or a viral vector according to the invention, or a composition according to the invention may be directly or indirectly administrated to a cell, tissue and/or an organ in vivo of an individual already affected by or at risk of developing a CEP290 related disease or condition, and may be administered directly or indirectly in vivo, ex vivo or in vitro. As Leber congenital amaurosis has a pronounced phenotype in retina cells, it is preferred that said cells are retina cells, it is further preferred that said tissue is the retina and/or it is further preferred that said organ comprises or consists of the eye.

The invention further provides a method for modulating splicing of CEP290 in a cell comprising contacting the cell, preferably a retina cell, with an exon skipping molecule according to the invention, or a viral vector according to the invention, or a composition according to the invention. The features of this aspect are preferably those defined earlier herein. Contacting the cell with an exon skipping molecule according to the invention, or a viral vector according to the invention, or a composition according to the invention may be performed by any method known by the person skilled in the art. Use of the methods for delivery of exon skipping molecules, viral vectors and compositions described herein is included. Contacting may be directly or indirectly and may be in vivo, ex vivo or in vitro.

The invention further provides a method for the treatment of a CEP290 related disease or condition requiring modulating splicing of CEP290 of an individual in need thereof, said method comprising contacting a cell, preferably a retina cell, of said individual with an exon skipping molecule according to the invention, or a viral vector according to the invention, or a composition according to the invention. The features of this aspect are preferably those defined earlier herein. Contacting the cell, preferably a retina cell with an exon skipping molecule according to the invention, or a viral vector according to the invention, or a composition according to the invention may be performed by any method known by the person skilled in the art. Use of the methods for delivery of molecules, viral vectors and compositions described herein is included. Contacting may be directly or indirectly and may be in vivo, ex vivo or in vitro. A preferred CEP290 related disease or condition is Leber congenital amaurosis.

Unless otherwise indicated each embodiment as described herein may be combined with another embodiment as described herein.

As can be observed in the experimental section herein, at the RNA level, addition of various AONs targeting the aberrant CEP290 exon indeed resulted in a conversion of aberrantly spliced CEP290 mRNA to correctly spliced CEP290 mRNA. This conversion will coincide with an increased synthesis of the wild-type CEP290 protein.

In fibroblasts (that can be derived from skin cells), CEP290 is abundantly expressed. Therefore, it is to be expected that addition of AONs to cultured fibroblasts from LCA patients will result in an increased amount of wild-type CEP290 protein that is detectable on Western blot, and as such will demonstrate that AON-based therapy will not only redirect normal splicing of CEP290 mRNA but will also result in restoring CEP290 protein function. This experiment is presently ongoing.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 0.1% of the value.

The sequence information as provided herein should not be so narrowly construed as to require inclusion of erroneously identified bases. The skilled person is capable of identifying such erroneously identified bases and knows how to correct for such errors. In case of sequence errors, the sequence of the polypeptide obtainable by expression of the gene present in SEQ ID NO: 1 containing the nucleic acid sequence coding for the polypeptide should prevail.

All patent and literature references cited in the present specification are hereby incorporated by reference in their entirety.

FIGURE LEGENDS

FIG. 1 CEP290 splicing and AON function

A) Normal CEP290 mRNA splicing of exons 26 and 27, resulting in wild-type CEP290 protein (figure discloses SEQ ID NOS 17-18, respectively, in order of appearance).

B) The most frequent LCA-causing mutation is an A-to-G transition (underlined and indicated with an asterisk) in intron 26 of CEP290. This mutation creates a splice donor site, which results in the inclusion of an aberrant exon to ~50% of the CEP290 mRNA and subsequent premature termination of the CEP290 protein (figure discloses SEQ ID NOS 19-20, respectively, in order of appearance).

C) Upon binding of sequence-specific AONs, factors involved in splicing will not recognize the aberrant splice donor site in intron 26, resulting in redirection of normal CEP290 splicing and synthesis of a correct CEP290 protein (figure discloses SEQ ID NOS 19, 21, and 20, respectively, in order of appearance).

FIG. 2 AON-Based Rescue of Aberrant CEP290 Splicing

A) RT-PCR analysis of CEP290 mRNA isolated from lymphoblastoid cells of one control individuals and two individuals affected with LCA, that were cultured in the absence or presence of a selected AON (AON-3) direct against the aberrant CEP290 exonin a final concentration of 1.0 µM. The upper band represents the aberrant CEP290 splice product, whereas the lower band represents the wild-type CEP290 splice product. M: 100-bp marker. MQ: negative water control.

B) Specificity of AON-based rescue. Similar to A), cells were transfected with AON-3, or a sense oligonucleotide directed to the same target site (SON-3). Left panel: RT-PCR reaction using primers located in exon 26 and exon 27. Right panel: RT-PCR reaction using primers located in exon 26 and exon 31.

C) Dose-dependent rescue of CEP290 mRNA splicing. Similar to A), cells were transfected with different concentrations of the selected AON, ranging from 0.01 to 1.0

FIG. 3 Sequence Specificity in AON-Based Rescue of Aberrant CEP290 Splicing

A) Overview of the aberrant CEP290 exon, and the relative positions of the AONs that were selected. The 5'-end of the aberrant exon is part of an Alu repeat.

B) RT-PCR analysis of CEP290 mRNA isolated from lymphoblastoid cells of an LCA patient that were cultured in the absence or presence of different AONs direct against the aberrant CEP290 exon (AON-1 to -5), or one sense oligonucleotide (SON-3). The AONs and SON were transfected in a final concentration of 0.1 µM. The upper band represents the aberrant CEP290 splice product, whereas the lower band represents the wild-type CEP290 splice product. M: 100-bp marker.

SEQUENCES

All sequences herein are depicted from 5'→3'

TABLE 1

Sequences as set forth in the Sequence Listing

| SEQ ID NO: | SEQ type | Description |
|---|---|---|
| 1 | Genomic DNA | CEP290 |
| 2 | cDNA | CEP290 |
| 3 | PRT | CEP290 protein |
| 4 | DNA | 128 nucleotide aberrant CEP290 exon |
| 5 | PRT | CEP290 aberrant protein |
| 6 | Polynucleotide | 143 nucleotide motif |
| 7 | Polynucleotide | 42 nucleotide motif |
| 8 | Polynucleotide | 24 nucleotide motif |
| 9 | AON-1 | taatcccagcactttaggag |
| 10 | AON-2 | gggccaggtgcggtgg |
| 11 | AON-3 | aactggggccaggtgcg |
| 12 | AON-4 | tacaactggggccaggtg |
| 13 | AON-5 | actcacaattacaactgggg |
| 14 | SON-3 | cgcacctggcccagtt |
| 15 | PCR primer | tgctaagtacagggacatcttgc |
| 16 | PCR primer | agactccacttgttcttttaaggag |

The present invention is further described by the following examples which should not be construed as limiting the scope of the invention.

Unless stated otherwise, the practice of the invention will employ standard conventional methods of molecular biology, virology, microbiology or biochemistry. Such techniques are described in Sambrook et al. (1989) Molecular Cloning, A Laboratory Manual (2$^{nd}$ edition), Cold Spring Harbor Laboratory, Cold Spring Harbor Laboratory Press; in Sambrook and Russell (2001) *Molecular Cloning: A Laboratory Manual*, Third Edition, Cold Spring Harbor Laboratory Press, NY; in Volumes 1 and 2 of Ausubel et al. (1994) *Current Protocols in Molecular Biology, Current Protocols*, USA; and in Volumes I and II of Brown (1998) *Molecular Biology LabFax*, Second Edition, Academic Press (UK); *Oligonucleotide Synthesis* (N. Gait editor); *Nucleic Acid Hybridization* (Hames and Higgins, eds.).

EXAMPLES

Materials and Methods

Design Antisense Oligonucleotides

The 128-bp sequence of the aberrant CEP290 exon that is included into the mutant CEP290 mRNA was analyzed for the presence of exonic splice enhancer motifs using the ESE finder 3.0 program (http://rulai.cshl.edu/cgi-bin/tools/ESE3/esefinder.cgi?process=home). RNA antisense oligonucleotides were purchased from Eurogentec, and designed with a $T_m$ of 58° C., and modified with a 2'-O-methyl group at the sugar chain and a phosphothiorate backbone, and dissolved in phosphate buffered saline.

Cell Culture

Human B-lymphoblasts cells of LCA patients homozygously carrying the intronic mutation in CEP290 were immortalized by transformation with the Eppstein-Barr virus, as described previously. (Wall F E, 1995). Cells were cultured in RPMI1640 medium (Gibco) containing 10% (v/v) fetal calf serum (Sigma), 1% 10 U/µl penicillin and 10 µg/µl streptomycin (Gibco), and 1% GlutaMAX (Gibco), at a density of $0.5 \times 10^6$ cells/ml. Cells were passaged twice a week.

Transfection of AONs

A day before transfection, $1.0 \times 10^6$ cells were seeded in each well of a 6-wells plate, in a total volume of 2 ml complete medium. Transfection mixtures were prepared by combining 2.5 µl AON in a desired concentration, or distilled water, 5 µl transfection reagent (ExGen in vitro 500, Fermentas) and 92.5 µl 150 mM NaCl, and incubated at room temperature for 10 minutes, before addition to the cells. Six hours after transfection, 8 ml of low-serum medium (complete medium with only 1% fetal calf serum) was added. Forty-eight hours after transfection, cells were collected and washed with 1×PBS, before directly proceeding to RNA isolation.

RNA Isolation and RT-PCR

Total RNA was isolated from transfected lymphoblastoid cells using the Nucleospin RNA II isolation kit (Machery Nagel), according to manufacturer's protocol. Subsequently, 1 µg of total RNA was used for cDNA synthesis using the iScript cDNA synthesis kit (Bio-Rad). Five percent of the cDNA was used for each PCR reaction. Part of the CEP290 cDNA was amplified under standard PCR conditions supplemented with 5% Q-solution (Qiagen), and using forward primer tgctaagtacagggacatcttgc (SEQ ID NO: 15) and reverse primer agactccacttgttctttttaaggag (SEQ ID NO: 16) that are located in exon 26 and exon 27 of the human CEP290 gene, respectively. PCR products were resolved on a 1.5% agarose gel. Bands presumably representing correctly and aberrantly spliced CEP290 were excised from the gel, purified using Nucleospin Extract II isolation kit and sequenced from both strands with the ABI PRISM Big Dye Terminator Cycle Sequencing V2.0 Ready Reaction kit and the ABI PRISM 3730 DNA analyzer (Applied Biosystems).

Introduction

Here, we describe the use of AONs to redirect normal splicing of CEP290 in patient-derived lymphoblast cells, and show a sequence-specific and dose-dependent decrease in levels of aberrantly spliced CEP290, thereby revealing the potential of AON-based therapy to treat CEP290-associated LCA.

Results

The intronic CEP290 mutation (c.2991+1655A>G) creates a cryptic splice donor site that results in the inclusion of an aberrant exon into the CEP290 mRNA (FIGS. 1A and -B). Addition of AONs directed against the aberrant exon would prevent the insertion of this exon by preventing the binding of factors that are essential for splicing such as the U1- and U2snRNP complexes, and serine-arginine rich proteins, thereby restoring normal CEP290 splicing and protein synthesis (FIG. 1C). AONs can target splice sites as well as exonic sequences, although in the particular case of the Duchenne muscular dystrophy DMD gene, AONs targeting exonic regions tend to outperform those that target the splice sites (Aartsma-Rus et al, 2010). In addition, previous studies have suggested a positive correlation between the capability of AONs to induce exon skipping and the presence of predicted SC35 splice factor binding sites in the target sequence (Aartsma-Rus et al, 2008). To design an AON with high exon-skipping potential, the aberrant CEP290 exon (128 nucleotides exonic sequence plus 15 nucleotides of intronic sequence on each side) was scrutinized for exonic splice enhancer binding motifs, using the ESE finder 3.0 program (Smith et al, 2006). At the 3'-end of the aberrant exon, two SC35-binding motifs were predicted (data not shown). Hence, the first AON was designed such that it encompassed these two motifs (designated AON-3, SEQ ID NO: 11), and being complementary to the CEP290 mRNA.

Figure 2A:
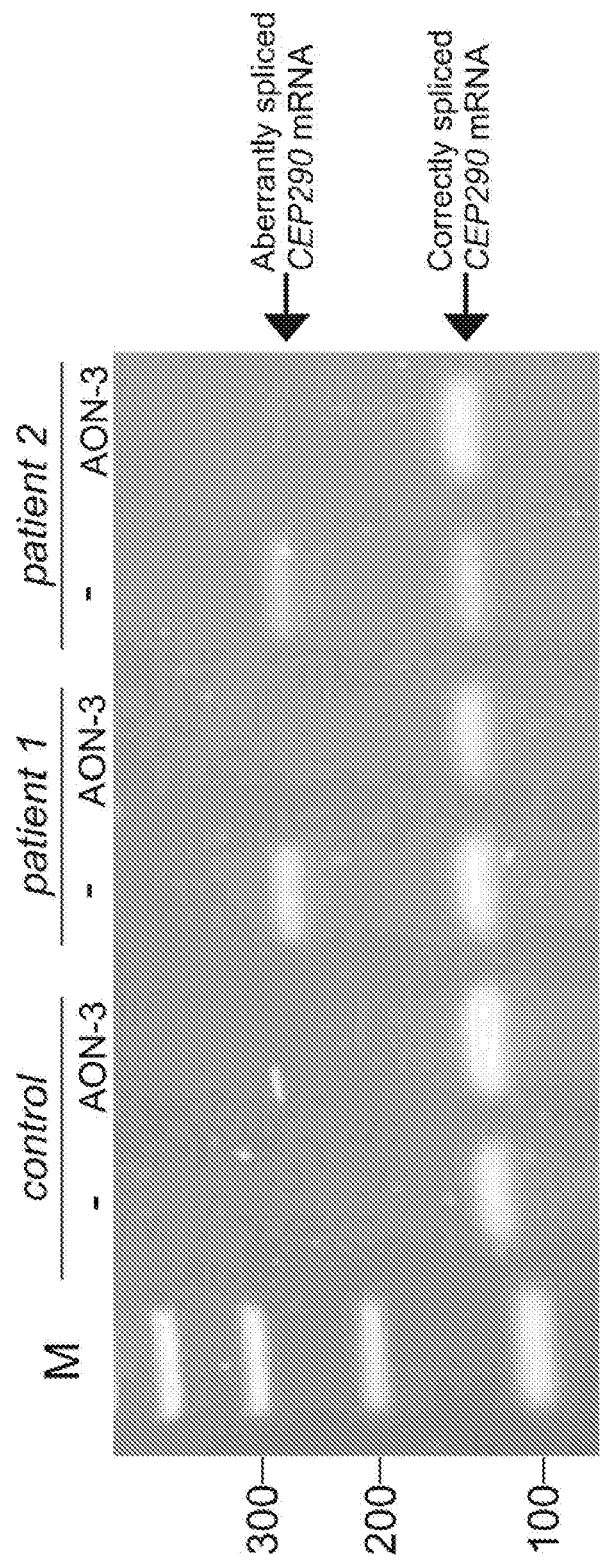
Figure 2B:
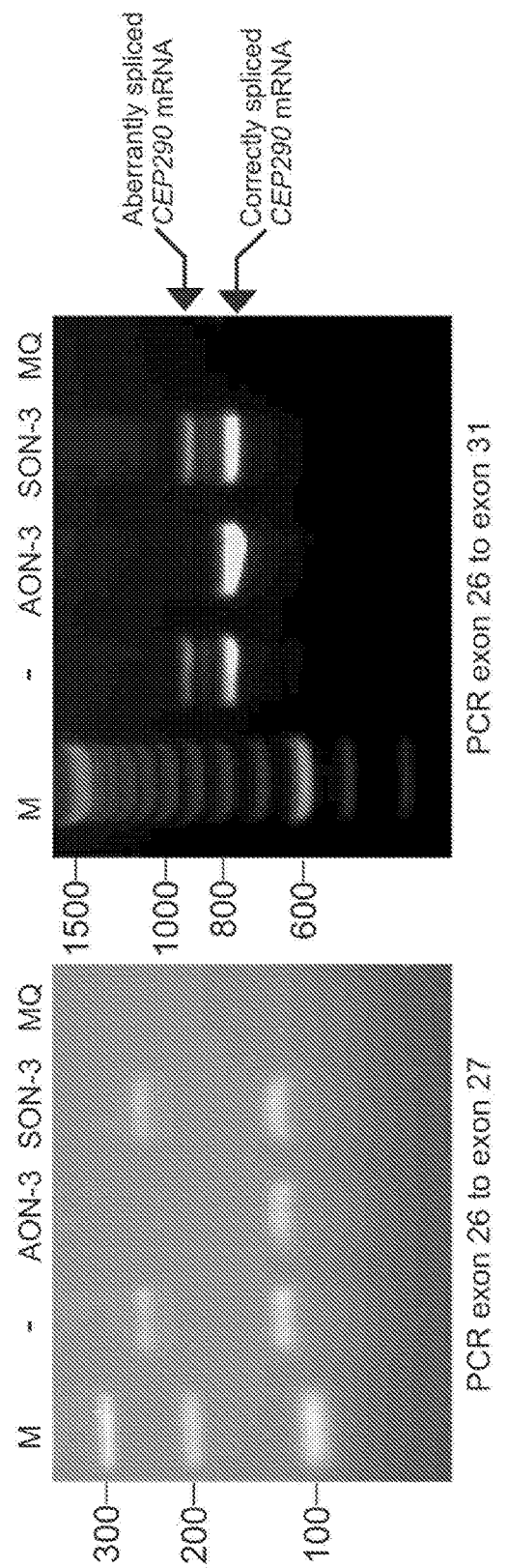
Figure 2C:
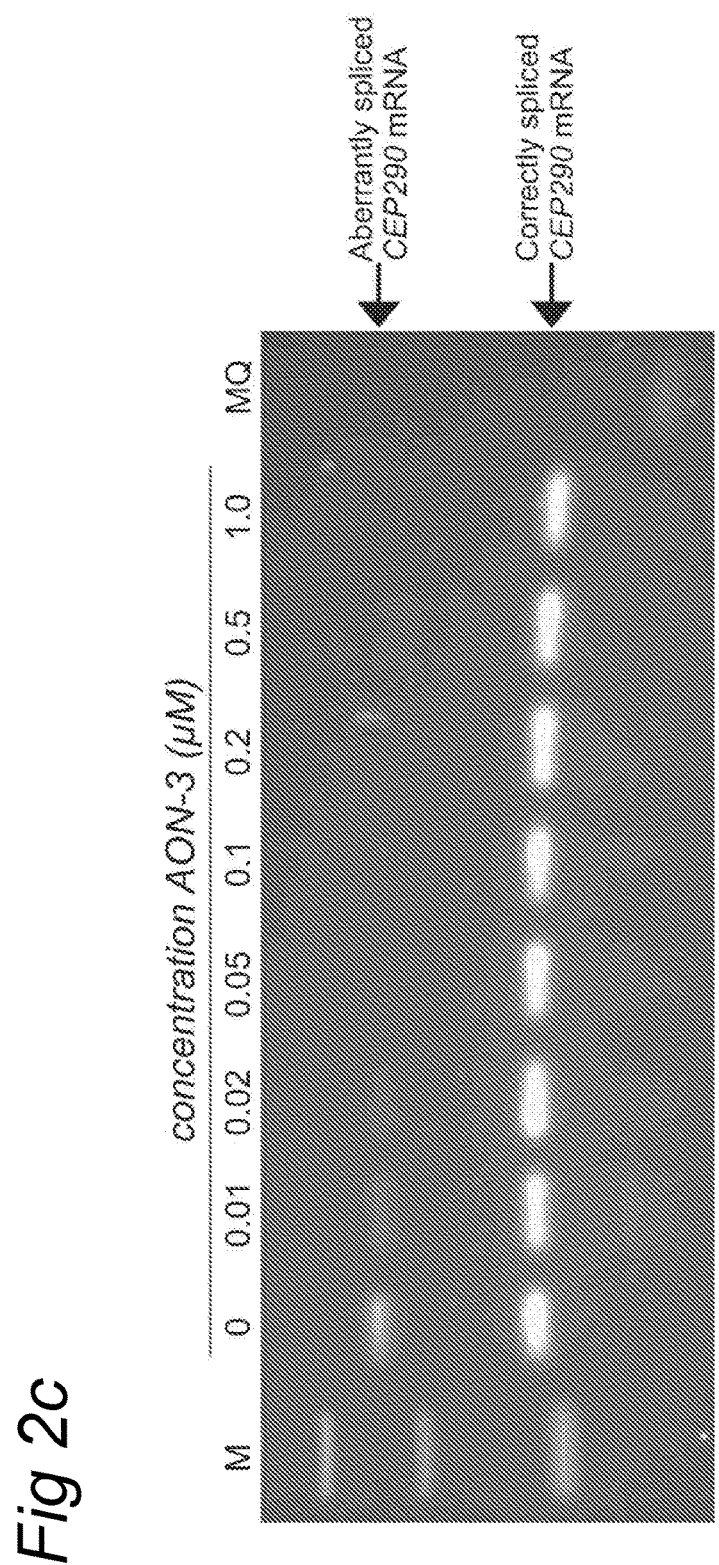

To determine whether AON-3 has exon-skipping potential in vitro, immortalized lympoblastoid cells of two unrelated individuals with LCA homozygously carrying the intronic CEP290 founder mutation c.2991+1655A>G, as well as one control individual were cultured in the absence or presence of 1 µM AON-3. As expected, in the control individual, only a band representing correctly spliced CEP290 was observed, whereas in both affected individuals two products were present, one representing correctly spliced, and one representing aberrantly spliced CEP290 mRNA. Upon addition of AON-3, a strong decrease in aberrantly spliced CEP290 was noted, in both individuals with LCA (FIG. 2A). Next, the specificity of AON-3 was assessed by transfecting a sense oligonucleotide directed to the same target site (SON-3, SEQ ID NO: 14). RT-PCR analysis showed that in the cells transfected with SON-3, both the aberrantly spliced and the correctly spliced CEP290 mRNA molecules are still present (FIG. 2B, left panel), demonstrating the specificity of the antisense sequence. Using an additional pair of primers that amplifies larger products, similar results were obtained (FIG. 2B, right panel). Interestingly, the decrease in aberrantly spliced CEP290 appears to coincide with an increased intensity of the product representing correctly spliced CEP290 mRNA. These data indicate that the aberrant product is not degraded, but that the AON transfection truly induces exon skipping, resulting in the synthesis of more correctly spliced wild-type CEP290 mRNA. To determine the effective dose of AON-3, cells were transfected with various concentrations of AON-3, ranging from 0.01 to 1.0 µM. Even at the lowest concentration of 0.01 µM, a marked reduction in aberrantly spliced CEP290 was observed. The maximum amount of exon skipping was observed at 0.05 or 0.1 µM of AON, indicating that these concentrations are sufficient to convert almost all aberrantly spliced CEP290 (FIG. 2C).

Figure 3A:
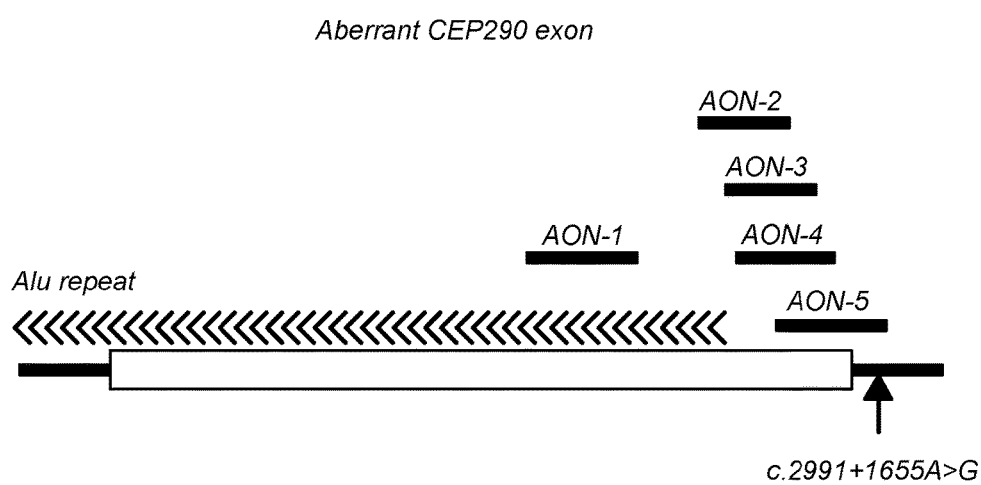
Figure 3B:
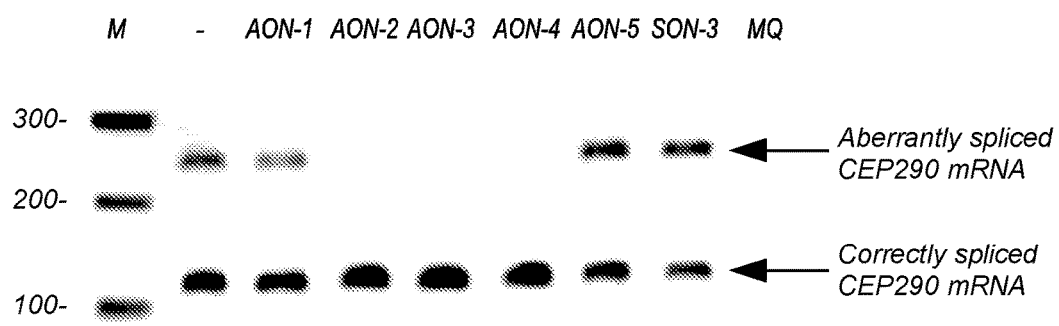

The effectiveness of AONs in splice modulation is thought to merely depend on the accessibility of the target mRNA molecule, and hence may differ tremendously between neighboring sequences. To determine whether this sequence specificity also applies for CEP290, several AONs were designed that target the aberrant CEP290 exon (Table 1). This exon consists of 128 base pairs, the majority of which are part of an Alu repeat, one of the most frequent repetitive elements in the human genome (Schmidt et al, 1982), covering the entire 5'-end of the aberrant exon (FIG. 3A). Hence, the majority of AONs were designed to be complementary to the 3'-end of the aberrant exon or the splice donor site (FIG. 3A). In total, five AONs were transfected at a final concentration of 0.1 µM, which was shown to be optimal for AON-3. Interestingly, besides AON-3, also AON-2 (SEQ ID NO: 10) and AON-4 (SEQ ID NO: 12) resulted in high levels of exon skipping. In contrast, AON-1 (SEQ ID NO: 9) that targets the Alu repeat region, and AON-5 (SEQ ID NO: 13) that is directed against the splice donor site, hardly showed any exon skipping potential (FIG. 3B). These data demonstrate the sequence specificity in AON-based exon skipping of CEP290 and highlight a small region of the aberrant CEP290 exon as a potential therapeutic target.

Discussion

In this study, we explored the therapeutic potential of AONs to correct a splice defect caused by an intronic mutation in CEP290. In immortalized lymphoblast cells of LCA patients homozygously carrying the intronic CEP290 mutation c.2991+1655A>G, transfection of some but not all AONs resulted in skipping of the aberrant exon, thereby almost fully restoring normal CEP290 splicing.

AONs have been the focus of therapeutic research for over a decade, for the treatment of a variety of genetic diseases (Hammond et al, 2011). These strategies include the use of AONs to block the recognition of aberrant splice sites, to alter the ratio between two naturally occurring splice isoforms, to induce skipping of exons that contain protein-truncating mutations, or to induce the skipping of exons in order to restore the reading-frame of a gene that is disrupted by a genomic deletion, allowing the synthesis of a (partially) functional protein (Hammond et al, 2011). The latter approach is already being applied in phase I/II clinical trials for the treatment of patients with Duchenne muscular dystrophy, with promising results (Kinali et al, 2009; van Deutekom et al, 2007).

The intronic CEP290 mutation is an ideal target for AON-based therapy, since this mutation results in the inclusion of an aberrant exon in the CEP290 mRNA which is normally not transcribed. Inducing skipping of this aberrant exon by AONs fully restores the normal CEP290 mRNA, allowing normal levels of CEP290 protein to be synthesized. A second major advantage is that although this AON-approach is a mutation-specific therapeutic strategy, the intronic CEP290 mutation is by far the most frequent LCA-causing mutation.[4] Based on the estimated prevalence of LCA (1:50,000), and the observed frequency of the intronic CEP290 mutation in Northern-Europe (26%) (Coppieters et al, 2010) and the U.S. (10%) (Stone, 2007), at least one thousand and, depending on the frequency of the mutation in other populations, perhaps many more individuals worldwide have LCA due to this mutation. Finally, although the LCA phenotype associated with CEP290 mutations is severe, it appears that the photoreceptor integrity, especially in the macula, as well as the anatomical structure of the visual connections to the brain, are relatively intact in LCA patients with CEP290 mutations, which would allow a window of opportunity for therapeutic intervention (Cideciyan et al, 2007).

The study described here provides a proof-of-principle of AON-based therapy for CEP290-associated LCA in vitro, using immortalized patient lymphoblast cells. In order to determine the true therapeutic potential of this method for treating LCA, additional studies are needed that include the development of therapeutic vectors, and assessment of efficacy and safety in animal models. Although naked AONs, or conjugated to cell-penetrating peptides, can be delivered to the retina by intraocular injections, the limited stability of the AONs would require multiple injections in each individual. In contrast, by using viral vectors, a single subretinal injection would suffice to allow a long-term expression of the therapeutic construct. Previously, others have used recombinant adeno-associated viral (rAAV) vectors carrying U1- or modified U7snRNA constructs to efficiently deliver AON sequences, in the mdx mouse model for DMD, or in DMD patient myoblasts, respectively (Geib et al, 2009; Goyenhalle et al, 2004). In line with this, AONs targeting the aberrant exon of CEP290 could be cloned within such constructs, and delivered to the retina by subretinal injections of rAAV-5 or -8 serotypes that efficiently transduce photoreceptor cells where the endogenous CEP290 gene is expressed (Alloca et al, 2007; Lebherz et al, 2008). Using rAAV-2 vectors, no long-lasting immune response was evoked upon subretinal injections of these vectors in patients with RPE65 mutations (Simonella et al, 2009), and also for rAAV-5 and rAAV-8, immune responses appear to be absent or limited, at least in animal models (Li et al, 2009; Vandenberghe et al, 2011). One final safety aspect concerns the specificity of the sequence that is used to block the splicing of the aberrant CEP290 exon. As stated before, the majority of this exon is part of an Alu repeat, and AONs directed against this repeat will likely bind at multiple sites in the human genome, increasing the chance to induce off-target effects. The AONs that were shown to be effective in this study do not fully target the Alu repeat sequence, but are also not completely unique in the human genome. However, when blasting against the EST database, no exact hits are found, indicating that at the level of expressed genes, these sequences are unlikely to induce off-target effects and deregulate normal splicing of other genes. To further study the efficacy and safety of AON-based therapy for CEP290-associated LCA in vivo, we are currently generating a transgenic knock-in mouse model that carries part of the human CEP290 gene (exon 26 to exon 27, with and without the intronic mutation) which is exchanged with its mouse counterpart. Compared to gene augmentation therapy, AON-based therapy has a number of advantages. First, in gene augmentation therapy, a ubiquitous or tissue-specific promoter is used to drive expression of the wild-type cDNA encoding the protein that is mutated in a certain patient. For instance in one clinical trial for RPE65 gene therapy, the chicken beta-actin promoter was used (Maguire et al, 2008). Using these but also fragments of the endogenous promoters, it is difficult to control the levels of expression of the therapeutic gene. In some cases, like for the RPE65 protein that has an enzymatic function, expression levels beyond those of the endogenous gene might not be harmful to the retina. For other genes however, including those that encode structural proteins like CEP290, tightly-regulated expression levels might be crucial for cell survival, and overexpression of the therapeutic protein might exert toxic effects. Using AONs, the therapeutic intervention occurs at the pre-mRNA level, and hence does not interfere with the endogenous expression levels of the target gene. A second issue is the use of the viral vector. Of a variety of different recombinant viral vectors, rAAVs are considered to be most suitable for treating retinal dystrophies, because of their relatively high transduction efficiency of retinal cells, and their limited immunogenicity. The major drawback of rAAVs however is their limited cargo size of 4.8 kb. Again, for some genes like RPE65, this is not a problem. For many other retinal genes however, like CEP290 (with an open reading frame of 7.4 kb), but also ABCA4 and USH2A, the size of their full-length cDNAs exceeds the cargo size of the currently available pool of rAAVs. One way to overcome this problem is to express cDNAs that express only partial proteins with residual activity, as has been suggested for CEP290 by expressing the N-terminal region of CEP290 in a zebrafish model (Baye et al, 2011). Other viral vectors, like lentivirus or adenoviruses have a higher cargo capacity that rAAVs (~8 kb), but are less efficient in transducing retinal cells, and adenoviruses have a higher immunogenic potential (den Hollander et al, 2010). For AON-based therapy, the size limitations of AAV are not a problem, since the small size of the AONs and the accompanying constructs easily fit within the available AAVs.

In conclusion, this study shows that administration of AONs to cultured patient cells almost fully corrects a splice defect that is caused by a frequent intronic mutation in CEP290 that causes LCA. These data warrant further research to determine the therapeutic potential of AON-based therapy for CEP290-associated LCA, in order to delay or cease the progression of this devastating blinding disease.

REFERENCE LIST

1. Leber, T. (1869). Uber Retinitis Pigmentosa and angeborene Amaurose. von Graefe's Archives Ophthalmology 15, 1-25.
2. Koenekoop, R. K., Lopez, I., den Hollander, A. I., Allikmets, R., and Cremers, F. P. (2007). Genetic testing for retinal dystrophies and dysfunctions: benefits, dilemmas and solutions. Clin Experiment Ophthalmol 35, 473-485.
3. Stone, E. M. (2007). Leber congenital amaurosis—a model for efficient genetic testing of heterogeneous disorders: LXIV Edward Jackson Memorial Lecture. Am J Ophthalmol 144, 791-811.
4. den Hollander, A. I., Roepman, R., Koenekoop, R. K., and Cremers, F. P. M. (2008). Leber congenital amaurosis: genes, proteins and disease mechanisms. Prog Retin Eye Res 27, 391-419.
5. Estrada-Cuzcano, A., Koenekoop, R. K., Coppieters, F., Kohl, S., Lopez, I., Collin, R. W. J., De Baere, E. B., Roeleveld, D., Marek, J., Bernd, A. et al (2011). IQCB1 mutations in patients with leber congenital amaurosis. Invest Ophthalmol V is Sci 52, 834-839.
6. den Hollander, A. I., Koenekoop, R. K., Yzer, S., Lopez, I., Arends, M. L., Voesenek, K. E., Zonneveld, M. N., Strom, T. M., Meitinger, T., Brunner, H. G. et al (2006). Mutations in the CEP290 (NPHP6) gene are a frequent cause of Leber congenital amaurosis. Am J Hum Genet. 79, 556-561.
7. Perrault, I., Delphin, N., Hanein, S., Gerber, S., Dufier, J. L., Roche, O., foort-Dhellemmes, S., Dollfus, H., Fazzi, E., Munnich, A. et al (2007). Spectrum of NPHP6/CEP290 mutations in Leber congenital amaurosis and delineation of the associated phenotype. Hum Mutat 28, 416.
8. Baala, L., Audollent, S., Martinovic, J., Ozilou, C., Babron, M. C., Sivanandamoorthy, S., Saunier, S., Salomon, R., Gonzales, M., Rattenberry, E. et al (2007). Pleiotropic effects of CEP290 (NPHP6) mutations extend to Meckel syndrome. Am J Hum Genet. 81, 170-179.
9. Frank, V., den Hollander, A. I., Bruchle, N. O., Zonneveld, M. N., Nurnberg, G., Becker, C., Du, B. G., Kendziorra, H., Roosing, S., Senderek, J. et al (2008). Mutations of the CEP290 gene encoding a centrosomal protein cause Meckel-Gruber syndrome. Hum Mutat 29, 45-52.
10. Helou, J., Otto, E. A., Attanasio, M., Allen, S. J., Parisi, M. A., Glass, I., Utsch, B., Hashmi, S., Fazzi, E., Omran, H. et al (2007). Mutation analysis of NPHP6/CEP290 in patients with Joubert syndrome and Senior-Loken syndrome. J Med Genet. 44, 657-663.
11. Valente, E. M., Silhavy, J. L., Brancati, F., Barrano, G., Krishnaswami, S. R., Castori, M., Lancaster, M. A., Boltshauser, E., Boccone, L., Al-Gazali, L. et al (2006). Mutations in CEP290, which encodes a centrosomal protein, cause pleiotropic forms of Joubert syndrome. Nat Genet. 38, 623-625.
12. Coppieters, F., Casteels, I., Meire, F., De Jaegere S., Hooghe, S., van Regemorter N., Van Esch H., Matuleviciene, A., Nunes, L., Meersschaut, V. et al (2010). Genetic screening of LCA in Belgium: predominance of CEP290 and identification of potential modifier alleles in AHI1 of CEP290-related phenotypes. Hum Mutat 31, E1709-E1766.
13. Littink, K. W., Pott, J. W., Collin, R. W. J., Kroes, H. Y., Verheij, J. B., Blokland, E. A., de Castro Miro M., Hoyng, C. B., Klayer, C. C., Koenekoop, R. K. et al (2010). A novel nonsense mutation in CEP290 induces exon skipping and leads to a relatively mild retinal phenotype. Invest Ophthalmol V is Sci 51, 3646-3652.
14. Bainbridge, J. W., Smith, A. J., Barker, S. S., Robbie, S., Henderson, R., Balaggan, K., Viswanathan, A., Holder, G. E., Stockman, A., Tyler, N. et al (2008). Effect of gene therapy on visual function in Leber's congenital amaurosis. N Engl J Med 358, 2231-2239.
15. Cideciyan, A. V., Aleman, T. S., Boye, S. L., Schwartz, S. B., Kaushal, S., Roman, A. J., Pang, J. J., Sumaroka, A., Windsor, E. A., Wilson, J. M. et al (2008). Human gene therapy for RPE65 isomerase deficiency activates the retinoid cycle of vision but with slow rod kinetics. Proc Natl Acad Sci USA 105, 15112-15117.
16. Hauswirth, W., Aleman, T. S., Kaushal, S., Cideciyan, A. V., Schwartz, S. B., Wang, L., Conlon, T., Boye, S. L., Flotte, T. R., Byrne, B. et al (2008). Phase I Trial of Leber Congenital Amaurosis due to Estrada-Mutations by Ocular Subretinal Injection of Adeno-Associated Virus Gene Vector: Short-Term Results. Hum Gene Ther
17. Maguire, A. M., Simonelli, F., Pierce, E. A., Pugh, E. N., Jr., Mingozzi, F., Bennicelli, J., Banfi, S., Marshall, K. A., Testa, F., Surace, E. M. et al (2008). Safety and efficacy of gene transfer for Leber's congenital amaurosis. N Engl J Med 358, 2240-2248.
18. Maguire, A. M., High, K. A., Auricchio, A., Wright, J. F., Pierce, E. A., Testa, F., Mingozzi, F., Bennicelli, J. L., Ying, G. S., Rossi, S. et al (2009). Age-dependent effects of RPE65 gene therapy for Leber's congenital amaurosis: a phase 1 dose-escalation trial. Lancet 374, 1597-1605.
19. den Hollander, A. I., Black, A., Bennett, J., and Cremers, F. P. M. (2010). Lighting a candle in the dark: advances in genetics and gene therapy of recessive retinal dystrophies. J Clin Invest 120, 3042-3053.
20. Aartsma-Rus, A., Houlleberghs, H., van Deutekom, J. C., van Ommen, G. J., and 't Hoen, P. A. (2010). Exonic sequences provide better targets for antisense oligonucleotides than splice site sequences in the modulation of Duchenne muscular dystrophy splicing. Oligonucleotides 20, 69-77.
21. Aartsma-Rus, A., van, V. L., Hirschi, M., Janson, A. A., Heemskerk, H., de Winter, C. L., de, K. S., van Deutekom, J. C., 't Hoen, P. A., and van Ommen, G. J. (2008). Guidelines for Antisense Oligonucleotide Design and Insight Into Splice-modulating Mechanisms. Mol Ther
22. Smith, P. J., Zhang, C., Wang, J., Chew, S. L., Zhang, M. Q., and Krainer, A. R. (2006). An increased specificity score matrix for the prediction of SF2/ASF-specific exonic splicing enhancers. Hum Mol Genet. 15, 2490-2508.
23. Schmid, C. W. and Jelinek, W. R. (1982). The Alu family of dispersed repetitive sequences. Science 216, 1065-1070.

24. Hammond, S. M. and Wood, M. J. (2011). Genetic therapies for RNA mis-splicing diseases. Trends Genet. 27, 196-205.
25. Kinali, M., rechavala-Gomeza, V., Feng, L., Cirak, S., Hunt, D., Adkin, C., Guglieri, M., Ashton, E., Abbs, S., Nihoyannopoulos, P. et al (2009). Local restoration of dystrophin expression with the morpholino oligomer AVI-4658 in Duchenne muscular dystrophy: a single-blind, placebo-controlled, dose-escalation, proof-of-concept study. Lancet Neurol 8, 918-928.
26. van Deutekom, J. C., Janson, A. A., Ginjaar, I. B., Frankhuizen, W. S., Aartsma-Rus, A., Bremmer-Bout, M., Den Dunnen, J. T., Koop, K., van der Kooi, A. J., Goemans, N. M. et al (2007). Local dystrophin restoration with antisense oligonucleotide PRO051. N Engl J Med 357, 2677-2686.
27. Coppieters, F., Lefever, S., Leroy, B. P., and De, B. E. (2010). CEP290, a gene with many faces: mutation overview and presentation of CEP290base. Hum Mutat 31, 1097-1108.
28. Cideciyan, A. V., Aleman, T. S., Jacobson, S. G., Khanna, H., Sumaroka, A., Aguirre, G. K., Schwartz, S. B., Windsor, E. A., He, S., Chang, B. et al (2007). Centrosomal-ciliary gene CEP290/NPHP6 mutations result in blindness with unexpected sparing of photoreceptors and visual brain: implications for therapy of Leber congenital amaurosis. Hum Mutat 28, 1074-1083.
29. Geib, T. and Hertel, K. J. (2009). Restoration of full-length SMN promoted by adenoviral vectors expressing RNA antisense oligonucleotides embedded in U7 snRNAs. PLoS One 4, e8204.
30. Goyenvalle, A., Vulin, A., Fougerousse, F., Leturcq, F., Kaplan, J. C., Garcia, L., and Danos, O. (2004). Rescue of dystrophic muscle through U7 snRNA-mediated exon skipping. Science 306, 1796-1799.
31. Allocca, M., Mussolino, C., Garcia-Hoyos, M., Sanges, D., Iodice, C., Petrillo, M., Vandenberghe, L. H., Wilson, J. M., Marigo, V., Surace, E. M. et al (2007). Novel adeno-associated virus serotypes efficiently transduce murine photoreceptors. J Virol 81, 11372-11380.
32. Lebherz, C., Maguire, A., Tang, W., Bennett, J., and Wilson, J. M. (2008). Novel AAV serotypes for improved ocular gene transfer. J Gene Med 10, 375-382.
33. Simonelli, F., Maguire, A. M., Testa, F., Pierce, E. A., Mingozzi, F., Bennicelli, J. L., Rossi, S., Marshall, K., Banfi, S., Surace, E. M. et al (2009). Gene Therapy for Leber's Congenital Amaurosis is Safe and Effective Through 1.5 Years After Vector Administration. Mol Ther
34. Li, W., Kong, F., Li, X., Dai, X., Liu, X., Zheng, Q., Wu, R., Zhou, X., Lu, F., Chang, B. et al (2009). Gene therapy following subretinal AAV5 vector delivery is not affected by a previous intravitreal AAV5 vector administration in the partner eye. Mol V is 15, 267-275.
35. Vandenberghe, L. H., Bell, P., Maguire, A. M., Cearley, C. N., Xiao, R., Calcedo, R., Wang, L., Castle, M. J., Maguire, A. C., Grant, R. et al (2011). Dosage Thresholds for AAV2 and AAV8 Photoreceptor Gene Therapy in Monkey. Sci Transl Med 3, 88ra54.
36. Baye, L. M., Patrinostro, X., Swaminathan, S., Beck, J. S., Zhang, Y., Stone, E. M., Sheffield, V. C., and Slusarski, D. C. (2011). The N-terminal region of centrosomal protein 290 (CEP290) restores vision in a zebrafish model of human blindness. Hum Mol Genet. 20, 1467-1477.
37. Dorn and Kippenberger, Curr Opin Mol Ther 2008 10(1) 10-20
38. Nielsen, et al. (1991) Science 254, 1497-1500
39. Govindaraju and Kumar (2005) Chem. Commun, 495-497
40. Egholm et al (1993) Nature 365, 566-568
41. Morita et al. 2001. Nucleic Acid Res Supplement No. 1: 241-242
42. Gorman L, et al, Stable alteration of pre-mRNA splicing patterns by modified U7 small nuclear RNAs. Proc Natl Acad Sci USA 1998; 95(9):4929-34
43. Suter D, et al, Double-target antisense U7 snRNAs promote efficient skipping of an aberrant exon in three human beta-thalassemic mutations. Hum Mol Genet. 1999; 8(13):2415-23
44. Remington: The Science and Practice of Pharmacy, 20th Edition. Baltimore, Md.: Lippincott Williams & Wilkins, 2000

What is claimed is:

1. An antisense oligonucleotide that is capable of inducing skipping of an aberrant 128 nucleotide exon from human CEP290 pre-mRNA, wherein said antisense oligonucleotide is complementary to at least twelve consecutive nucleotides of SEQ ID NO: 7, wherein said antisense oligonucleotide comprises at least one phosphorothioate internucleoside linkage and wherein each nucleotide within said antisense oligonucleotide comprises a 2'-O alkyl modification.

2. The antisense oligonucleotide according to claim 1, wherein said antisense oligonucleotide has a length from 12 to 60 nucleotides.

3. The antisense oligonucleotide according to claim 2, wherein said antisense oligonucleotide comprises a sequence selected from the group consisting of SEQ ID NO: 10, SEQ ID NO: 11, and SEQ ID NO: 12.

4. The antisense oligonucleotide according to claim 1, wherein the 2'-O alkyl modification is selected from the group consisting of 2'-O-methyl modified ribose (RNA), 2'-O-ethyl modified ribose, and 2'-O-propyl modified ribose.

5. A viral vector expressing an antisense oligonucleotide that is capable of inducing the skipping of an aberrant 128 nucleotide exon from human CEP290 pre-mRNA, wherein said antisense oligonucleotide is complementary to at least twelve consecutive nucleotides of SEQ ID NO:7.

6. A pharmaceutical composition comprising an antisense oligonucleotide according to claim 1 and a pharmaceutically acceptable excipient.

* * * * *